(12) United States Patent
Reynolds et al.

(10) Patent No.: US 7,361,660 B2
(45) Date of Patent: Apr. 22, 2008

(54) CHEMICAL COMPOUNDS

(75) Inventors: Rachel Heulwen Reynolds, Loughborough (GB); Anthony Howard Ingall, Loughborough (GB)

(73) Assignee: AstraZeneca AB (SE)

( * ) Notice: Subject to any disclaimer, the term of this patent is extended or adjusted under 35 U.S.C. 154(b) by 445 days.

(21) Appl. No.: 10/483,161

(22) PCT Filed: Jul. 16, 2002

(86) PCT No.: PCT/GB02/03250

§ 371 (c)(1),
(2), (4) Date: Jan. 8, 2004

(87) PCT Pub. No.: WO03/008422

PCT Pub. Date: Jan. 30, 2003

(65) Prior Publication Data

US 2004/0171623 A1    Sep. 2, 2004

(30) Foreign Application Priority Data

Jul. 19, 2001  (GB) ................................ 0117583.5

(51) Int. Cl.
C07D 495/04 (2006.01)
A61K 31/519 (2006.01)
A61P 37/06 (2006.01)

(52) U.S. Cl. ..................................... 514/258; 544/278
(58) Field of Classification Search ................ 514/258; 544/278

See application file for complete search history.

(56) References Cited

U.S. PATENT DOCUMENTS

| | | | |
|---|---|---|---|
| 6,180,635 B1 * | 1/2001 | Cheshire et al. | 514/260.1 |
| 6,232,320 B1 | 5/2001 | Stewart et al. | |
| 6,300,334 B1 * | 10/2001 | Bantick et al. | 514/260.1 |
| 6,342,502 B1 | 1/2002 | Cheshire et al. | |
| 7,064,126 B2 | 6/2006 | Cooper et al. | |
| 2004/0254198 A1 | 12/2004 | Reynolds et al. | |
| 2006/0052400 A1 | 3/2006 | Guile | |
| 2006/0135539 A1 | 6/2006 | Guile et al. | |

FOREIGN PATENT DOCUMENTS

| | | |
|---|---|---|
| WO | WO 98/54190 | 12/1998 |
| WO | WO 99/29695 | 6/1999 |
| WO | WO 00/12514 | 3/2000 |
| WO | WO 03/011868 | 2/2003 |
| WO | WO 2004/065393 | 8/2004 |
| WO | WO 2004/065394 | 8/2004 |
| WO | WO 2004/065395 | 8/2004 |

OTHER PUBLICATIONS

AllRefer.com Health entry for Chronic Obstructive Pulmonary Disease <<http://health.allrefer.com/health/chronic-obstructive-pulmonary-disease-prevention.html>> downloaded from the Internet Aug. 23, 2004.

BestHealth entry for ARDS (adult respiratory distress syndrome) <http://www.wfabme.edu/besthealth/ency/article/000103prv.htm>.
Gupta et al., "Tacrolimus: a review of its use for the management of dermatoses", *J. Eur. Acad. Dermatol. Venereal.* 16:100-114 (2002).
MDAdvice.com entry for Asthma http://www.mdadvice.com/topics/asthma/info/1.htm downloaded from the internet Mar. 5, 2003.
Meagher et al., "Atopic dematitis: Review of immunopathogenesis and advances in immunosuppressive therapy", *Australas. J. Derm.* 43:247-254 (2002).
"New Drugs for Asthma, Allergy and COPD", *Prog Respir Res. Basel*, Karger, 31:212-216 (2001).
Perrett et al., "Cyclosporin in childhood psoriasis", *Journal of Dermatological Treatment* 14:113-118 (2003).
Tan et al., "Psoriasis", *Drugs of Today* 34(7):641-647 (1998).
Thestrup-Pedersen, "Tacrolimus treatment of atopic eczema/dermatitis syndrome", *Curr Opin Allergy Clin Immunol* 3:359-362 (2003).
Wolff et al., "Pimecrolimus for the treatment of inflammatory skin disease", *Expert Opin. Pharmacother.* 5:643-655 (2004).
Yamaguchi et al., "Novel Antiasthmatic Agents with Dual Activities of Thromboxane $A_2$ Synthetase Inhibition and Bronchodilation. V. Thienopyridazinone Derivatives", *Chem. Pharm. Bull.* 43(2):236-240 (1995).
Yamamoto et al., "Topical tacrolimus: an effective therapy for facial psoriasis", *Eur J Dermatol* 13:471-473 (2003).
Yu et al., "Refractory atopic dermatitis treated with low dose cyclosporin", *Annals of Allergy, Asthma & Immunology* 89:127-131.

* cited by examiner

*Primary Examiner*—James O. Wilson
*Assistant Examiner*—Paul V. Ward
(74) *Attorney, Agent, or Firm*—Fish & Richardson P.C.

(57) ABSTRACT

The invention relates to a compound of formula (1)(A chemical formula should be inserted here—please see paper copy enclosed) wherein Q is —CO— or —C($R^4$)($R^5$)— (wherein $R^4$ is a hydrogen atom or $C_{1-4}$alkyl and $R^5$ is a hydrogen atom or hydroxy group) and Ar is a 5- to 10-membered aromatic ring system wherein up to 4 ring atoms may be heteroatoms independently selected from nitrogen, oxygen and sulphur, the ring system being optionally substituted by one or more substituents as defined in the specification. It also relates to methods of preparing, pharmaceutical compositions containing and methods of using the compound of the formula (1), particularly in the modulation of autoimmune disease.

(1)

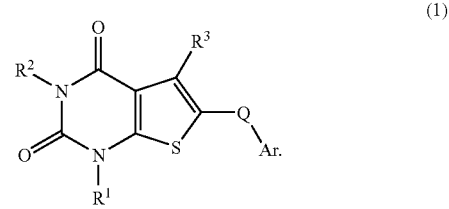

15 Claims, No Drawings

CHEMICAL COMPOUNDS

CROSS-REFERENCE TO RELATED APPLICATIONS

This application is the national phase application under 35 U.S.C. § 371 of PCT International Application No. PCT/GB02/03250, which has an International filing date of Jul. 16, 2002, and which designated United Kingdom Application Serial No. 0117583.5, filed Jul. 19, 2001, as priority. The contents of these applications are incorporated by reference in their entirety.

The present invention relates to thieno[2,3-d]pyrimidinediones, processes for their preparation, pharmaceutical compositions containing them and their use in therapy. In particular, in their use in the modulation of autoimmune disease.

T-cells play an important role in the immune response, however in auto-immune disease T-cells are inappropriately activated against particular tissues and proliferate, eg causing the inflammation associated with rheumatoid arthritis. Inhibition of the proliferation of T-cells is beneficial in the modulation of autoimmune disease. The present invention relates to compounds which are beneficial in the modulation of autoimmune disease.

The compounds of WO 2000/12514 and WO2001/038489 are known to be useful in modulating the immune response. These applications encompass compounds having an amidic C—N— at the 5-position of the thienopyrimidine ring system. These compounds exist as slowly-interconverting rotamers, because of the combination of slow rotations around the is amidic C—N link and around the bond from the amidic carbonyl to the thienopyrimidine core; the rate of interconversion is such that the isomers may be separated by HPLC. Such hindered rotation presents significant problems for the development of a pharmaceutical compound: long equilibration times imply that different initial rotameric mixtures may be expected to arise if the conditions of the final step of the synthesis is varied, leading to problems in assaying purity and reproducing the solid form of the raw drug. Moreover rotameric forms having lifetimes comparable to biological half lives may be expected to be handled by metabolic processes in different ways, potentially giving rise to structurally dissimilar metabolites, the biological activity and safety of all of which must be fully studied and documented. We have now found a class of compounds which have an amidic —C—N— group or sulphonamidic —S—N— group at the 5-position of the thienopyrimidine ring system, have interesting potency and yet do not have the problems associated with the compounds existing as separate rotamers under ambient conditions.

In accordance with the present invention, there is provided a compound of formula (1)

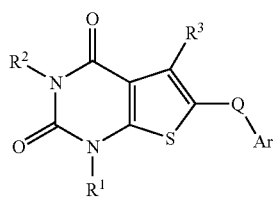

(1)

wherein:
R$^1$ and R$^2$ each independently represent a C$_{1-6}$alkyl, C$_{3-4}$alkenyl, C$_{3-6}$cycloalkylC$_{1-3}$alkyl or C$_{3-6}$cycloalkyl; each of which may be optionally substituted by 1 to 3 halogen atoms;

R$^3$ is a group —CON(R$^{10}$)YR$^{11}$ or —SO$_2$N(R$^{10}$)YR$^{11}$; [wherein Y is O, S or NR$_{12}$ (wherein R$^{12}$ is hydrogen or C$_{1-6}$alkyl);

and R$^{10}$ and R$^{11}$ are independently C$_{1-6}$alkyl optionally substituted by halo, hydroxy, amino, C$_{1-6}$alkylamino or di-(C$_{1-6}$alkyl)amino];
Q is —CO— or —C(R$^4$)(R$^5$)— (wherein R$^4$ is a hydrogen atom or C$_{1-4}$alkyl and R$^5$ is a hydrogen atom or hydroxy group);
Ar is a 5- to 10-membered aromatic ring system wherein up to 4 ring atoms may be heteroatoms independently selected from nitrogen, oxygen and sulphur, the ring system being is optionally substituted by one or more substituents independently selected from C$_{1-4}$alkyl (optionally substituted by 1, 2 or 3 hydroxy groups), C$_{1-4}$alkoxy, halogen, haloalkyl, dihaloalkyl, trihaloalkyl, C$_{1-4}$alkoxyC$_{1-4}$alkyl, C$_{1-4}$alkylthio, C$_{1-4}$alkoxycarbonyl, C$_{2-4}$alkanoyl, oxo, thioxo, nitro, cyano, —N(R$^6$)R$^7$ and —CH$_2$)pN(R$^8$)R$^9$, hydroxy, C$_{1-4}$alkylsulphonyl, C$_{1-4}$alkylsulphinyl, carbamoyl, C$_{1-4}$alkylcarbamoyl, di-(C$_{1-4}$alkyl)carbamoyl, carboxy, or a 5 or 6 membered aromatic ring containing up to 4 heteroatoms independently selected from nitrogen, oxygen and sulphur;
p is 1 to 4
R$^6$ and R$^7$ each independently represent a hydrogen atom, C$_{1-4}$alkanoyl or C$_{1-4}$alkyl, or together with the nitrogen atom to which they are attached form a 5- to 7-membered saturated heterocyclic ring;
R$^8$ and R$^9$ each independently represent a hydrogen atom, C$_{1-4}$alkanoyl or C$_{1-4}$ alkyl, or together with the nitrogen atom to which they are attached form a 5- to 7-membered saturated heterocyclic ring;

or a pharmaceutically acceptable salt or prodrug thereof.

In another aspect the invention relates to a compound of the formula (1) as hereinabove defined or to a pharmaceutically-acceptable salt thereof.

Within the present invention it is to be understood that a compound of the formula 1 or a salt thereof may exhibit the phenomenon of tautomerism and that the formulae drawings within this specification can represent only one of the possible tautomeric forms. It is to be understood that the invention encompasses any tautomeric form and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

The present invention relates to the compounds of formula 1 as hereinbefore defined as well as to the salts thereof. Salts for use in pharmaceutical compositions will be pharmaceutically acceptable salts, but other salts may be useful in the production of the compounds of formula 1 and their pharmaceutically acceptable salts. Pharmaceutically acceptable salts of the invention may, for example, include acid addition salts of the compounds of formula 1 as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula 1 are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Preferred salts include an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, *Advanced Drug Delivery Reviews,* 8, 1-38 (1992);
d) H. Bundgaard, et al., *Journal of Pharmaceutical Sciences,* 77, 285 (1988); and
e) N. Kakeya, et al., *Chem. Pharm. Bull.,* 32, 692 (1984).

Examples of such pro-drugs may be used to form in-vivo-cleavable esters of a compound of the Formula 1. An in vivo hydrolysable ester of a compound of the formula (I) containing a hydroxy group is, for example, a pharmaceutically acceptable ester which is hydrolysed in the human or animal body to produce the parent alcohol. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

It is also to be understood that certain compounds of the formula (1) can exist in solvated forms as well as unsolvated forms, for example, hydrated forms. It is to be understood that the invention encompasses all such solvated forms, which are useful in therapy, in particular for the particular therapeutic purposes mentioned hereinafter.

In the present specification, unless otherwise indicated, an alkyl, alkenyl or alkynyl group or an alkyl, alkenyl or alkynyl moiety in a substituent group may be linear or branched.

Ar may be bonded to the —C($R^4$)($R^5$)— group by a ring carbon atom or a ring nitrogen providing this does not lead to quaternisation.

It will be appreciated that in a group —C($R^4$)($R^5$)Ar, $R^5$ may represent a hydroxy group only when Ar is bonded to —C($R^4$)($R^5$) through a carbon atom and not a heteroatom. Furthermore, it should be understood that in —C(O)Ar, Ar is bonded through a carbon atom and not a heteroatom to the moiety —C(O). A hydroxyalkyl may contain more than one hydroxy group but a single hydroxy group is preferred.

For the avoidance of doubt, when Ar is substituted by an oxo or thioxo group, it is intended that Ar includes the dihydro-versions of aromatic ring systems. For example, it encompasses thiazolyl and 2,3-dihydrothiazolyl (when the latter is substituted by an oxo or thioxo group). Similarly Ar encompasses, for example, 2,3-dihydrobenzoxazolyl, 2,3-dihydrobenzothiazolyl, 2,3-dihydropyrazinyl and 2,3-dihydrobenzimidazolyl (when these are substituted by an oxo or thioxo group).

Ar is a 5- to 10-membered aromatic ring system wherein up to 4 ring atoms may be heteroatoms independently selected from nitrogen, oxygen and sulphur, the ring system being optionally substituted by one, two, three or four substituents independently selected from $C_{1-4}$alkyl (optionally substituted by 1, 2 or 3 hydroxy groups) (e.g. methyl, ethyl, n-propyl, n-butyl, hydroxymethyl, 2-hydroxyethyl, 1-hydroxyethyl or 3-hydroxypropyl), $C_{1-4}$alkoxy (e.g. methoxy, ethoxy, n-propoxy or n-butoxy), halogen (e.g. fluorine, chlorine, bromine or iodine), haloalkyl, (e.g. fluoromethyl, chloromethyl, bromomethyl, 2-fluoroethyl, 2-fluoropropyl or 3-fluoropropyl), dihaloalkyl, (e.g. difluoromethyl, dichloromethyl, chlorofluoromethyl, dibromomethyl, 2,2-difluoroethyl, 2,2-difluoropropyl or 2,3-difluoropropyl), trihaloalkyl, (e.g. trifluoromethyl, trichloromethyl, 2,2,2-trifluoroethyl, 2,2,2-trifluoropropyl or 2,2,3-trifluoropropyl), $C_{1-4}$alkoxy$C_{1-4}$alkyl, (e.g. methoxymethyl, ethoxymethyl, 2-methoxyethyl, 2-methoxypropyl or 3-methoxypropyl), $C_{1-4}$alkylthio (e.g. methylthio, ethylthio, n-propylthio or n-butylthio), $C_{1-4}$alkoxycarbonyl (e.g. methoxycarbonyl, ethoxycarbonyl, n-propoxycarbonyl, isopropoxycarbonyl or n-butoxycarbonyl), $C_{2-4}$alkanoyl (e.g. acetyl or propionyl), oxo, thioxo, nitro, cyano, —N($R^6$)$R^7$ (e.g. amino, N-methylamino, N-ethylamino, di-N,N-methylamino or N-ethyl-N-methylamino), —(CH$_2$)$_p$N($R^8$)$R^9$ [e.g.—CH$_2$N($R^8$)$R^9$, —CH$_2$CH$_2$N($R^8$)$R^9$ or CH$_2$CH$_2$CH$_2$N($R^8$)$R^9$], hydroxy, $C_{1-4}$alkylsulphonyl (e.g. methylsulphonyl, ethylsulphonyl or propylsulphonyl), $C_{1-4}$alkylsulphinyl (methylsulphinyl, ethylsulphinyl or propylsulphinyl), carbamoyl, $C_{1-4}$alkylcarbamoyl (e.g. methylcarbamoyl, ethylcarbamoyl and propylcarbamoyl) di-$C_{1-4}$alkylcarbamoyl (e.g. di-N,N-methylcarbamoyl, N-ethyl-N-methylcarbamoyl or di-N,N-ethylcarbamoyl), carboxy and or a 5 or 6 membered aromatic ring containing up to 4 heteroatoms independently selected from nitrogen, oxygen and sulphur (e.g. phenyl, pyrimidyl, thienyl and furanyl).

The aromatic ring system may be monocyclic or polycyclic (e.g. bicyclic), examples of which include phenyl, naphthyl, quinolyl, pyrazolyl, thienyl, oxazolyl, imidazolyl, pyridinyl, pyrrolo[2,3-b]pyridyl, benzimidazolyl, indazolyl, benzothiazolyl, 2,3-dihydrobenzothiazolyl, benzoxazolyl, thiazolyl, 2,3-dihydrothiazolyl, 2,3-dihydrobenzimidazolyl, 2,3-dihydrobenzoxazolyl, thiazolo[5,4-b]pyridyl and benzotriazolyl.

Further values of $R^1$, $R^2$, $R^3$, $R^4$, $R^5$, $R^6$, $R^7$, $R^8$, $R^9$, $R^{10}$, $R^{11}$, $R^{12}$, p, Q and Ar and substituents on Ar are further defined hereinafter. Such values may be used where appropriate with any of the definitions, claims or embodiments defined hereinafter or hereinbefore.

In one aspect Ar is a 5 or 6 membered monocyclic ring.
In another aspect Ar is a 8, 9 or 10 bicyclic ring.
In yet another aspect Ar is a 9 or 10 bicyclic ring.
In one aspect the invention relates to compounds of the formula 1 wherein Ar is a 5- to 10-membered aromatic ring system containing up to 4 ring heteroatoms selected from nitrogen, oxygen and sulphur providing that there is at least 1 ring nitrogen, the ring being optionally substituted as defined above. These compound have been found to be advantageous.

In another aspect Ar is a 5- to 10-membered aromatic ring system containing 1 or 2 ring nitrogen atoms and optionally one ring sulphur or oxygen atom or containing 3 ring nitrogen atoms, the ring being optionally substituted as defined above.

In another aspect Ar is a 5- to 10-membered aromatic ring system containing 1 or 2 ring nitrogen atoms and optionally one ring sulphur atom, the ring being optionally substituted as defined above.

In another aspect Ar is a 5- to 10-membered aromatic ring system containing 2 ring nitrogen, the ring being optionally substituted as defined above.

In yet another aspect Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo[2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl.

In yet another aspect Ar is selected from imidazolyl, pyrazolyl, pyrrolyl, isoxazolyl, quinolyl, indolyl, benzimidazolyl, indazolyl, benztriazolyl, 2,3-dihydrothiazolyl, 2,3-dihydrobenzoxazolyl, pyrrolo [2,3-bipyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl.

In yet another aspect Ar is selected from imidazolyl, pyrazolyl, benzimidazolyl, indazolyl, benztriazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydropyrazinyl and 2,3-dihydrobenzimidazolyl.

In yet another aspect Ar is selected from imidazolyl, pyrazolyl, pyrrolyl, isoxazolyl, phenyl and 2,3-dihydropyrazinyl.

In yet another aspect Ar is selected from quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo[1,2-a]pyridyl, imidazo[4,5-b]pyridyl, 2,3-dihydrothiazolo[5,4-b]pyridyl, 2,3-dihydrobenzothiazolyl and 2,3-dihydrobenzimidazolyl.

In yet another aspect, Ar is selected from imidazolyl, quinolyl, indolyl, benzimidazolyl, indazolyl, pyridopyrrolyl, 2,3-dihydrobenzothiazolyl, or 2,3-dihydrobenzimidazolyl.

$R^1$ and $R^2$ each independently represent $C_{1-6}$-alkyl, particularly $C_{1-5}$alkyl (e.g. methyl, ethyl, n-propyl, 1-methylethyl, n-butyl, 2-methylpropyl, 2,2-dimethylpropyl, n-pentyl or n-hexyl), $C_{3-6}$alkenyl, particularly $C_{3-4}$alkenyl (e.g. 1-propenyl, 1-butenyl, 1-pentenyl or 1-hexenyl), $C_{3-5}$cycloalkyl$C_{1-3}$alkyl (cyclopropylmethyl, cyclobutylmethyl, cyclopentylmethyl, 2-(cyclopropyl)ethyl, 2-(cyclobutyl)ethyl or 2-(cyclopentyl)ethyl) or $C_{3-6}$cycloalkyl, particularly $C_{5-6}$cycloalkyl (cyclopropyl, cyclobutyl, cyclopentyl or cyclohexyl) each of which may be optionally substituted by 1 to 3 halogen atoms (e.g. trifluoromethyl 2,2,2-trifluoroethyl, 2-chloroethyl, 2-chloropropyl or 3,3,3-trifluoropropyl).

In another aspect, $R^1$ and $R^2$ each independently represent $C_{1-5}$alkyl or $C_{3-6}$cycloalkylmethyl, each optionally substituted by 1 to 3 halogen atoms.

In yet another aspect, $R^1$ is ethyl, n-propyl, 1-methylethyl, 2-methylpropyl, 2,2-dimethylpropyl, cyclopropylmethyl, trifluoromethyl 2,2,2-trifluoroethyl, 2-chloroethyl, 2-chloropropyl or 3,3,3-trifluoropropyl.

In yet another aspect $R^1$ is ethyl, n-propyl, 1-methylethyl, 2-methylpropyl, 2,2-dimethylpropyl or cyclopropylmethyl.

In yet another aspect, $R^1$ is 2-methylpropyl.

In one aspect $R^2$ is methyl or trifluoromethyl.

In yet another aspect, $R^2$ is methyl.

In yet another aspect, $R^{10}$ and $R^{11}$ are $C_{1-4}$alkyl, which is either unsubstituted or substituted by 1 or 2 substituents.

In yet another aspect, $R^{10}$ is $C_{1-4}$alkyl optionally substituted by hydroxy.

In yet another aspect, $R^{10}$ is methyl, ethyl, hydroxymethyl or 2-hydroxyethyl.

In yet another aspect, $R^{10}$ is methyl, ethyl or 2-hydroxyethyl.

In yet another aspect, $R^{10}$ is methyl or 2-hydroxyethyl.

In yet another aspect, $R^{10}$ is methyl.

In yet another aspect, $R^{11}$ is $C_{1-4}$alkyl optionally substituted by hydroxy.

In yet another aspect, $R^{11}$ is methyl, ethyl, hydroxymethyl or 2-hydroxyethyl;

In yet another aspect, $R^{11}$ is methyl or 2-hydroxyethyl.

In yet another aspect, $R^{11}$ is $C_{1-4}$alkyl. In yet another aspect, $R^{11}$ is methyl.

In another aspect $R^{12}$ is methyl or ethyl.

In yet another aspect $R^{12}$ is methyl.

In yet another aspect, $R^3$ is of the formula —CON($R^{10}$)Y$R^{11}$.

In yet another aspect, $R^3$ is of the formula —SO$_2$N($R^{10}$)Y$R^{11}$.

In another aspect, Y is O.

In another aspect, $R^3$ is —CON(Me)OMe, —CON(Et)OMe, —CON(OEt)Me, —CON(Et)OEt, —CON(CH$_2$CH$_2$OH)OEt, —CON(CH$_2$CH$_2$OH)Me, —CON(OCH$_2$CH$_2$OH)Me or —CON(OCH$_2$CH$_2$OH)Et.

In yet another aspect, $R^3$ is —CON(Me)OMe, —CON(CH$_2$CH$_2$OH)OMe, —CON(OCH$_2$CH$_2$OH)Me or —CON(Et)OMe.

In another aspect, $R^3$ is —SO$_2$N(Me)OMe, —SO$_2$N(Et)OMe, —SO$_2$N(OEt)Me, —SO$_2$N(Et)OEt, —SO$_2$N(CH$_2$CH$_2$OH)OEt, —SO$_2$N(CH$_2$CH$_2$OH)Me, —SO$_2$N(OCH$_2$CH$_2$OH)Me or —SO$_2$N(OCH$_2$CH$_2$OH)Et.

In yet another aspect, $R^3$ is —SO$_2$N(Me)OMe, —SO$_2$N(CH$_2$CH$_2$OH)OMe, —SO$_2$N(OCH$_2$CH$_2$OH)Me or —SO$_2$N(Et)OMe.

In yet another aspect, $R^3$ is —CON(Me)OMe or —CON(CH$_2$CH$_2$OH)OMe.

In yet another aspect, $R^3$ is —CON(Me)OMe.

In another aspect, $R^4$ and $R^5$ are independently hydrogen or methyl.

In yet another aspect, Q is —CO— or —CH$_2$—.

In one aspect Q is —CO—.

In another aspect Q is —CH$_2$—.

In another aspect, Ar is unsubstituted or substituted by 1, 2 or 3 substituents.

In another aspect, Ar is unsubstituted or substituted by 1 or 2 substituents.

In another aspect, when the substituent on Ar is a 5 or 6 membered aromatic ring, this substituent on Ar contains up to 2 heteroatoms independently selected from nitrogen, oxygen and sulphur. In one aspect it is selected from furanyl, thienyl, phenyl and pyrimidinyl. In another aspect, it is selected from pyrimidyl and phenyl. In yet another aspect, it is phenyl.

Examples of the type of ring formed by $R^6$ and $R^7$ together with the nitrogen atom to which they attached include pyrrolidino, piperidino, morpholino, pierazino, azepano, 1,4-oxepano and 1,4 diazepano. In another aspect, the ring is selected from pyrrolidino, piperidino or morpholino.

Examples of the type of ring formed by $R^8$ and $R^9$ together with the nitrogen atom to which they attached include pyrrolidino, piperidino, morpholino, pierazino, azepano, 1,4-oxepano and 1,4 diazepano. In another aspect, the ring is selected from pyrrolidino, piperidino or morpholino.

$R^6$ and $R^7$ each independently represent a hydrogen atom, $C_{1-4}$alkanoyl (e.g. formyl, acetyl or propionyl) or $C_{1-4}$ alkyl (e.g. methyl, ethyl, n-propyl or n-butyl), or together with the nitrogen atom to which they are attached form a 5- to 7-membered saturated heterocyclic ring.

In yet another aspect, $R^6$ and $R^7$ each independently represent a hydrogen atom or $C_{1-4}$ alkyl.

$R^8$ and $R^9$ each independently represent a hydrogen atom, $C_{1-4}$alkanoyl (e.g. formyl, acetyl or propionyl) or $C_{1-4}$ alkyl (e.g. methyl, ethyl, n-propyl or n-butyl), or together with the nitrogen atom to which they are attached form a 5- to 7-membered saturated heterocyclic ring.

In yet another aspect, $R^8$ and $R^9$ each independently represent a hydrogen atom or $C_{1-4}$ alkyl In yet another aspect, substituents for Ar include $C_{1-4}$alkyl (optionally substituted by 1 or 2 hydroxy groups), $C_{1-4}$alkoxy, halogen, trihaloalkyl, $C_{1-4}$alkylthio, $C_{1-4}$alkoxycarbonyl, $C_{2-4}$alkanoyl, oxo, thioxo, cyano, —$NHR^7$ and —$(CH_2)pN(R^8)R^9$ (wherein p is 1 or 2), hydroxy, $C_{1-4}$alkylsulphonyl, carbamoyl, $C_{1-4}$alkylcarbamoyl, di-($C_{1-4}$alkyl) carbamoyl, carboxy, or a 5 or 6 membered aromatic ring containing up to 4 heteroatoms independently selected from nitrogen, oxygen and sulphur.

In yet another aspect, substituents for Ar include methyl, ethyl, n-propyl, iso-propyl, tert-butyl, hydroxymethyl, trifluoromethyl, chloro, fluoro, bromo, hydroxymethyl, acetyl, methylthio, methoxycarbonyl, amino, methylamino, furanyl, thienyl, pyrimidyl, phenyl, cyano, thioxo and oxo.

In yet another aspect, substituents for Ar include methyl, ethyl, propyl, isopropyl, tert-butyl, hydroxymethyl, trifluoromethyl, chloro, fluoro, bromo, acetyl, methylthio, methoxycarbonyl, amino, methylamino, phenyl, pyrimidyl, cyano, thioxo and oxo.

In one aspect, substituents are $C_{1-4}$alkyl, halogen and, especially, trifluoromethyl, oxo and alkylthio.

In another aspect, substituents include methyl, ethyl, propyl, 1-methylethyl, chloro, fluoro, bromo, acetyl, methylthio, amino, methylamino and oxo.

In yet another aspect, substituents include methyl, propyl, 1-methylethyl, chloro, acetyl, methylthio, methylamino and oxo.

In yet another aspect, substituents are methyl, chloro, oxo and methylthio.

Particular values for Ar include 2,4,5-trichloroimidazol-]-yl, 2-(1-methylethyl)imidazol-1-yl, 2-chloroimidazol-1-yl, 4,5-dichloro-2-methylimidazol-1-yl, 4,5-dichloro-2-hydroxymethylimidazol-1-yl, 2,4,5-trichloro-2-methylimidazol-1-yl, 4,5-dichloroimidazol-2-yl, 2-bromo-4,5-dichloroimidazol-2-yl, 2-methylthio-imidazoly-1-yl, 3,5-dimethylpyrazol-4-yl, 1,3,5-trimethylpyrazol-4-yl, 3,5-dimethylpyrazol-4-yl, 3-tert-butyl-5-methylpyrazol-4-yl, 3,5-dimethylpyrazol-1-yl, 5-methyl-3-phenylpyrazol-4-yl, 5-methyl-3-(trifluoromethyl)pyrazol-4-yl, 5-methyl-3-(prop-2-yl)pyrazol-4-yl, 3,5-methyl-1-phenylpyrazol-4-yl, 5-dichloro-2,3-dihydro-2-oxothiazol-3-yl, 4-chloro-2,3-dihydro-2-oxothiazol-3-yl, 3,5-dimethyl isoxazol-4-yl, 2,4-dimethyl-1-(prop-2-yl)pyrrol-3-yl, 2-methoxycarbonyl-4-methylpyrrol-3-yl, 3-methoxycarbonyl-2,5-dimethylpyrrol-3-yl, phenyl, 2-(trifluoromethyl)phenyl, 2,3-dihydro-6-methyl-3-oxopyrazinyl, quinol-4-yl, quinol-5-yl, 6-fluoroquinol-4-yl, 8-fluoroquinol-4-yl, 2-methylquinol-4-yl, 3-chloroquinol-4-yl, 2-methylindol-3-yl, 7-methylindol-3-yl, 5-cyanoindol-1-yl, 1-acetylindol-3-yl, indazol-3-yl, 2-methylbenzimidazol-1-yl, 2-ethylbenzimidazol-1-yl, 2-propylbenzimidazol-1-yl, 2-methylthiobenzimidazol-1-yl, 2-hydroxymethylbenzimidazol-1-yl, 2-methylaminobenzimidazol-1-yl, 2-aminobenzimidazol-1-yl, 2-oxo-2,3-dihydrobenzoxazol-3-yl, pyrrolo[2,3-b]pyridin-3-yl, 2-methylpyrrolo[2,3-b]pyridin-1-yl, 2-methylpyrrolo[2,3-b]pyridin-3-yl, imidazo[1,2-a]pyrid-3-yl, 2-(methylthio)imidazo[4,5-b]pyrid-1-yl, 2-(methylthio)imidazo[4,5-b]pyrid-3-yl, 1H-1,2,3-benzotriazol-1-yl, 1-methyl-2-oxo-2,3-dihydrobenzimidazol-1-yl, 2-oxo-2,3-dihydrobenzothiazol-3-yl, 2-thioxo-2,3-dihydrobenzothiazol-3-yl, 2-oxo-2,3-dihydrobenzoxazol-1-yl, 2-oxo-2,3-dihydrobenzimidazol-3-yl, 2-oxo-2,3-dihydrobenzimidazol-1-yl, 5,6-difluoro-2-oxo-2,3-dihydrobenzimidazol-1-yl and 2-oxo-1,3-thiazolo[5,4-b]pyridin-3-yl.

Particular values for Ar include quinol-4-yl, 2-(1-methylethyl)imidazol-1-yl, 2-chloroimidazol-1-yl, 2-(methylthio)imidazol-1-yl, 3-chloroquinol-4-yl, 1-acetylindol-3-yl, 2-methylthiobenzimidazol-1-yl, 2-methylaminobenzimidazol-1-yl, 2-propylbenzimidazol-1-yl, indazol-3-yl, 2-methylpyrrolo[2,3-b]pyridin-3-yl, 2-oxo-2,3-dihydrobenzothiazol-3-yl and 1-methyl-2-oxo-2,3-dihydrobenzimidazol-1-yl.

A particular class of compound is of the formula (I) wherein:
$R^1$ is $C_{1-5}$alkyl or $C_{3-6}$cycloalkylmethyl;
$R^2$ is $C_{1-5}$alkyl;
$R^3$ is a group —$CON(R^{10})YR^{11}$ [wherein Y is O, S or $NR_{12}$ (wherein $R^{12}$ is hydrogen or $C_{1-6}$alkyl) and $R^{10}$ and $R^{11}$ are independently $C_{1-6}$-alkyl optionally substituted by halo, hydroxy, amino, $C_{1-6}$alkylamino or di-($C_{1-6}$alkyl)amino];
Q is —CO— or —$CH_2$—;
Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —$N(R^6)R^7$ and —$(CH_2)pN(R^8)R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;
$R^6$ and $R^7$ each independently represent a hydrogen atom or $C_{1-4}$alkyl, or together with the nitrogen atom to which they are attached form a 5- to 7-membered saturated heterocyclic ring;
$R^8$ and $R^9$ each independently represent a hydrogen atom or $C_{1-4}$ alkyl, or together with the nitrogen atom to which they are attached form a 5- to 7-membered saturated heterocyclic ring;
or a pharmaceutically-acceptable salt thereof.

Another class of compound is of the formula (1) wherein:
$R^1$ is $C_{1-5}$alkyl or $C_{3-6}$cycloalkylmethyl;
$R^2$ is $C_{1-5}$alkyl;
$R^3$ is a group —$SO_2N(R^{10})YR^{11}$ [wherein Y is O, S or $NR_{12}$ (wherein $R^{12}$ is hydrogen or $C_{1-6}$alkyl) and $R^{10}$ and $R^{11}$ are independently $C_{1-6}$alkyl optionally substituted by halo, hydroxy, amino, $C_{1-6}$alkylamino or di-($C_{1-6}$alkyl)amino];
Q is —CO— or —$CH_2$—;

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is $C_{1-5}$alkyl or $C_{3-6}$cycloalkylmethyl;

$R^2$ is methyl;

$R^3$ is a group —CON($R^{10}$)YR$^{11}$ [wherein Y is O, S or NR$_{12}$ (wherein $R^{12}$ is hydrogen or $C_{1-6}$alkyl) and $R^{10}$ and $R^{11}$ are independently $C_{1-6}$alkyl optionally substituted by halo, hydroxy, amino, $C_{1-4}$alkylamino or di-($C_{1-6}$alkyl)amino];

Q is —CO— or CH$_2$—;

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or cyclopropylmethyl;

$R^2$ is methyl;

$R^3$ is a group —CON($R^{10}$)OR$^{11}$ [wherein $R^{10}$ and $R^{11}$ are independently $C_{1-6}$-alkyl optionally substituted by halo, hydroxy, amino, $C_{1-6}$-alkylamino or di-($C_{1-6}$alkyl)amino];

Q is —CO— or CH$_2$—;

Ar is a 5- to 10-membered aromatic ring system containing up to 4 ring heteroatoms selected from nitrogen, oxygen and sulphur providing that there is at least 1 ring nitrogen, the ring being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or to cyclopropylmethyl;

$R^2$ is methyl;

$R^3$ is a group —CON($R^{10}$)OR$^{11}$ [wherein $R^{10}$ and $R^{11}$ are independently $C_{1-4}$alkyl optionally substituted by hydroxy);

Q is —CO— or —CH$_2$—;

Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo[2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl, the ring being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from nitrogen, oxygen and sulphur;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:
$R^1$ is ethyl, n-propyl, 1-methylethyl, 2-methylpropyl, 2,2-dimethylpropyl or cyclopropylmethyl;
$R^2$ is methyl;
$R^3$ is a group —CON($R^{10}$)O$R^{11}$ [wherein $R^{10}$ and $R^{11}$ are independently $C_{1-4}$alkyl optionally substituted by hydroxy];
Q is —CO— or —CH$_2$—;
Ar is selected from imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo[2,3-b]pyridyl, imidazo[1,2-a]pyridyl, imidazo[4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl, the ring being optionally substituted by one or more substituents independently selected from methyl, ethyl, n-propyl, iso-propyl, tert-butyl, hydroxymethyl, trifluoromethyl, chloro, fluoro, bromo, hydroxymethyl, acetyl, methylthio, methoxycarbonyl, amino, methylamino, furanyl, thienyl, pyrimidyl, phenyl, cyano, thioxo and oxo;
or a pharmaceutically-acceptable salt thereof.

Another particular class of compound is of the formula (1) wherein:
$R^1$ is ethyl, n-propyl, 1-methylethyl, 2-methylpropyl, 2,2-dimethylpropyl or cyclopropylmethyl;
$R^2$ is methyl;
$R^3$ is a group —CON($R^{10}$)O$R^{11}$ [wherein $R^{10}$ and $R^{11}$ are independently $C_{1-4}$alkyl optionally substituted by hydroxy];
Q is —CO— or —CH$_2$—;
Ar is 2,4,5-trichloroimidazol-1-yl, 2-(1-methylethyl) imidazol-1-yl, 2-chloroimidazol-1-yl, 4,5-dichloro-2-methylimidazol-1-yl, 4,5-dichloro-2-hydroxymethylimidazol-1-yl, 2,4,5-trichloro-2-methylimidazol-1-yl, 4,5-dichloroimidazol-2-yl, 2-bromo-4,5-dichloroimidazol-2-yl, 2-methylthioimidazoly-1-yl, 3,5-dimethylpyrazol-4-yl, 1,3,5-trimethylpyrazol-4-yl, 3,5-dimethylpyrazol-4-yl, 3-tert-butyl-5-methylpyrazol-4-yl, 3,5-dimethylpyrazol-1-yl, 5-methyl-3-phenylpyrazol-4-yl, 5-methyl-3-(trifluoromethyl)pyrazol-4-yl, 5-methyl-3-(prop-2-yl)pyrazol-4-yl, 3,5-methyl-1-phenylpyrazol-4-yl, 5-dichloro-2,3-dihydro-2-oxothiazol-3-yl, 4-chloro-2,3-dihydro-2-oxothiazol-3-yl, 3,5-dimethylisoxazol-4-yl, 2,4-dimethyl-1-(prop-2-yl)pyrrol-3-yl, 2-methoxycarbonyl-4-methylpyrrol-3-yl, 3-methoxycarbonyl-2,5-dimethylpyrrol-3-yl, phenyl, 2-(trifluoromethyl)phenyl, 2,3-dihydro-6-methyl-3-oxopyrazinyl, quinol-4-yl, quinol-5-yl, 6-fluoroquinol-4-yl, 8-fluoroquinol-4-yl, 2-methylquinol-4-yl, 3-chloroquinol-4-yl, 2-methylindol-3-yl, 7-methylindol-3-yl, 5-cyanoindol-1-yl, 1-acetylindol-3-yl, indazol-3-yl, 2-methylbenzimidazol-1-yl, 2-ethylbenzimidazol-1-yl, 2-propylbenzimidazol-1-yl, 2-methylthiobenzimidazol-1-yl, 2-hydroxymethylbenzimidazol-1-yl, 2-methylaminobenzimidazol-1-yl, 2-aminobenzimidazol-1-yl, 2-oxo-2,3-dihydrobenzoxazol-3-yl, pyrrolo[2,3-b]pyridin-3-yl, 2-methylpyrrolo[2,3-b]pyridin-1-yl, 2-methylpyrrolo[2,3-b]pyridin-3-yl, imidazo[1,2-a]pyrid-3-yl, 2-(methylthio)imidazo[4,5-b]pyrid-1-yl, 2-(methylthio)imidazo[4,5-b]pyrid-3-yl, 1H-1,2,3-benzotriazol-1-yl, 1-methyl-2-oxo-2,3-dihydrobenzimidazol-1-yl, 2-oxo-2,3-dihydrobenzothiazol-3-yl, 2-thioxo-2,3-dihydrobenzothiazol-3-yl, 2-oxo-2,3-dihydrobenzoxazol-1-yl, 2-oxo-2,3-dihydrobenzimidazol-3-yl, 2-oxo-2,3-dihydrobenzimidazol-1-yl, 5,6-difluoro-2-oxo-2,3-dihydrobenzimidazol-1-yl or 2-oxo-1,3-thiazolo[5,4-b]pyridin-3-yl;
or a pharmaceutically-acceptable salt thereof.

In another aspect of the invention, there is provided a compound of formula (1) wherein:
$R^1$ and $R^2$ each independently represent a $C_{1-6}$alkyl, $C_{3-6}$alkenyl, $C_{3-5}$cycloalkyl($C_{1-3}$)methyl or $C_{3-6}$cycloalkyl; each of which may be optionally substituted by 1 to 3 halogen atoms;
$R^3$ is a group —CON($R^{10}$)Y$R^{11}$ or —SO$_2$N($R^{10}$)Y$R^{11}$;
[wherein Y is O, S or NR$_{12}$ (wherein $R^{12}$ is hydrogen or $C_{1-4}$alkyl);
and $R^{10}$ and $R^{11}$ are independently $C_{1-6}$alkyl optionally substituted by halo, hydroxy, amino, $C_{1-6}$alkylamino or di-($C_{1-6}$alkyl)amino];
Q is —CO— or —C($R^4$)($R^5$)— (wherein $R^4$ is a hydrogen atom or $C_{1-4}$alkyl and $R^5$ is a hydrogen atom or hydroxy group);
Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, —N($R^6$)$R^7$ and —CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy;
p is 1 to 4
$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring;
$R^8$ and $R^9$ each independently represent a hydrogen atom, $C_{1-4}$alkanoyl or $C_{1-4}$ alkyl, or together with the nitrogen atom to which they are attached form a 5- to 7-membered saturated heterocyclic ring;

or a pharmaceutically acceptable salt or prodrug thereof.

A particular class of compound is of the formula (1) wherein:
$R^1$ is $C_{1-5}$alkyl or $C_{3-6}$cycloalkylmethyl;
$R^2$ is $C_{1-5}$alkyl;
$R^3$ is a group —CON($R^{10}$)Y$R^{11}$ [wherein Y is O, S or NR$_{12}$ (wherein $R^{12}$ is hydrogen or $C_{1-6}$alkyl) and $R^{10}$ and $R^{11}$ are independently $C_{1-6}$alkyl optionally substituted by halo, hydroxy, amino, $C_{1-6}$alkylamino or di-($C_{1-6}$alkyl)amino];
Q is —CO— or —CH$_2$—;
Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, NR$^6$R$^7$ and —CH$_2$NR$^8$R$^9$;
$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another class of compound is of the formula (1) wherein:

$R^1$ is $C_{1-5}$alkyl or $C_{3-4}$cycloalkylmethyl;

$R^2$ is $C_{1-5}$alkyl;

$R^3$ is a group —$SO_2N(R^{10})YR^{11}$ [wherein Y is O, S or $NR_{12}$ (wherein $R^{12}$ is hydrogen or $C_{1-6}$alkyl) and $R^{10}$ and $R^{11}$ are independently $C_{1-4}$alkyl optionally substituted by halo, hydroxy, amino, $C_{1-6}$alkylamino or di-($C_{1-4}$alkyl)amino];

Q is —CO— or —$CH_2$—;

Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{14}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is $C_{1-5}$alkyl or $C_{3-6}$-cycloalkylmethyl;

$R^2$ is methyl;

$R^3$ is a group —$CON(R^{10})YR^{11}$ [wherein Y is O, S or $NR_{12}$ (wherein $R^{12}$ is hydrogen or $C_{1-6}$alkyl) and $R^{10}$ and $R^{11}$ are independently $C_{1-6}$alkyl optionally substituted by halo, hydroxy, amino, $C_{1-6}$alkylamino or di-($C_{1-6}$alkyl)amino];

Q is —CO— or —$CH_2$—;

Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^1R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated-heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or cyclopropylmethyl;

$R^2$ is methyl;

$R^3$ is a group —$CON(R^{10})OR^{11}$ [wherein $R^{10}$ and $R^{11}$ are independently $C_{1-6}$alkyl optionally substituted by halo, hydroxy, amino, $C_{1-6}$-alkylamino or di-($C_{1-6}$alkyl)amino);

Q is —CO— or —$CH_2$—;

Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or cyclopropylmethyl;

$R^2$ is methyl;

$R^3$ is a group —$CON(R^{10})OR^{11}$ [wherein $R^{10}$ is $C_{1-4}$alkyl optionally substituted by hydroxy and $R^{11}$ is methyl];

Q is —CO— or —$CH_2$—;

Ar is a 5- to 10-membered aromatic ring system wherein up to 4 ring atoms may be heteroatoms independently selected from nitrogen, oxygen and sulphur, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or cyclopropylmethyl;

$R^2$ is methyl;

$R^3$ is a group —$CON(R^{10})OR^{11}$ [wherein $R^{10}$ is $C_{1-4}$alkyl optionally substituted by hydroxy and $R^{11}$ is methyl];

Q is —CO— or —$CH_2$—;

Ar is selected from imidazolyl, quinolyl, indolyl, benzimidazolyl, indazolyl, pyridopyrrolyl, 2,3-dihydrobenzothiazolyl and 2,3-dihydrobenzimidazolyl, the ring system being optionally substituted by 1, 2 or 3 substituents independently selected from $C_{1-4}$alkyl, $C_{1-4}$alkoxy, halogen, haloalkyl, dihaloalkyl, trihaloalkyl, hydroxy$C_{1-4}$alkyl, $C_{1-4}$alkoxy$C_{1-4}$alkyl, $C_{1-4}$alkylthio, $C_{1-4}$alkoxycarbonyl, $C_{2-4}$alkanoyl, oxo, nitro, cyano, $NR^6R^7$ and —$CH_2NR^8R^9$;

$R^6$ and $R^7$ each independently represent a hydrogen atom or $C_{1-4}$alkyl, or together with the nitrogen atom to which they are attached form a 5- to 7-membered saturated heterocyclic ring;

$R^8$ and $R^9$ each independently represent a hydrogen atom or $C_{1-4}$ alkyl, or together with the nitrogen atom to which they are attached form a 5- to 7-membered saturated heterocyclic ring;

or a pharmaceutically-acceptable salt thereof.

Another particular class of compound is of the formula (1) wherein:

$R^1$ is ethyl, n-propyl, 1-methylethyl, 2-methylpropyl, 2,2-dimethylpropyl or cyclopropylmethyl;

$R^2$ is methyl;

$R^3$ is a group —$CON(R^{10})OR^{11}$ [wherein $R^{10}$ is $C_{1-4}$alkyl optionally substituted by hydroxy and $R^{11}$ is methyl];

Q is —CO— or —$CH_2$—;

Ar is selected from imidazolyl, quinolyl, indolyl, benzimidazolyl, indazolyl, pyridopyrrolyl, 2,3-dihydrobenzothiazolyl and 2,3-dihydrobenzimidazolyl, the ring system being optionally substituted by 1, 2 or 3 substituents independently selected from methyl, ethyl, propyl, 1-methylethyl, chloro, fluoro, bromo, acetyl, methylthio, amino, methylamino and oxo;

or a pharmaceutically-acceptable salt thereof.

Particular compounds of the present invention include:

6-[(4,5-dichloro-2-methyl-1H-imidazol-1-yl)methyl]-1,2,3,4-tetrahydro-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-2,4-dioxo-6-(4-quinolinylmethyl)thieno[2,3-d]pyrimidine-5-carboxamide;

1,2,3,4-tetrahydro-N-methoxy-N,3-dimethyl-]-(2-methylpropyl)-2,4-dioxo-6-(1H-pyrrolo[2,3-b]pyridin-3-ylmethyl)-thieno[2,3-d]pyrimidine-5-carboxamide;

1,2,3,4-tetrahydro-6-(1H-indol-3-ylmethyl)-N-methoxy-N,3-dimethyl-1-(2-methylpropyl)-2,4-dioxo-thieno[2,3-d]pyrimidine-5-carboxamide;

1,2,3,4-tetrahydro-6-(1H-indol-3-ylcarbonyl)-N-methoxy-N,3-dimethyl-1-(2-methylpropyl)-2,4-dioxo-thieno[2,3-d]pyrimidine-5-carboxamide;

6-[(4,5-dichloro-2-methyl-1H-imidazol-1-yl)methyl]-1,2,3,4-tetrahydro-N-methoxy-N,3-dimethyl-1-(1-methylethyl)-2,4-dioxo-thieno[2,3-d]pyrimidine-5-carboxamide;

1,2,3,4-tetrahydro-6-(1H-indazol-3-ylmethyl)-N-methoxy-N,3-dimethyl-1-(2-methylpropyl)-2,4-dioxo-thieno[2,3-d]pyrimidine-5-carboxamide;

6-[(4,5-dichloro-2-methyl-1H-imidazol-1-yl)methyl]-1,2,3,4-tetrahydro-N-methoxy-N,3-dimethyl-2,4-dioxo-1-propyl-thieno[2,3-d]pyrimidine-5-carboxamide;

1-(2,2-dimethylpropyl)-1,2,3,4-tetrahydro-N-methoxy-N,3-dimethyl-2,4-dioxo-6-(quinolin-4-ylmethyl)-thieno[2,3-d]pyrimidine-5-carboxamide;

1,2,3,4-tetrahydro-N-methoxy-N,3-dimethyl-6-[[2-(1-methylethyl)-1H-imidazol-1-yl]methyl]-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-6-[[2-(methylthio)-1H-imidazol-1-yl]methyl]-2,4-dioxo-thieno[2,3-d]pyrimidine-5-carboxamide;

6-[(2-chloro-1H-imidazol-1-yl)methyl]-1,2,3,4-tetrahydro-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-6-[2-(methylthio)-1H-benzimidazol-1-yl]-2,4-dioxo-thieno[2,3-d]pyrimidine-5-carboxamide;

1,2,3,4-tetrahydro-N-(2-hydroxyethyl)-N-methoxy-3-methyl-1-(2-methylpropyl)-6-[[2-(methylthio)-1H-imidazol-1-yl]methyl]-2,4-dioxodthieno[2,3-d]pyrimidine-5-carboxamide;

1,2,3,4-tetrahydro-6-[[2-(methylamino)-1H-benzimidazol-1-yl]methyl]-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-2,4-dioxo-6-[(2-propyl-1H-benzimidazol-1-yl)methyl]-thieno[2,3-d]pyrimidine-5-carboxamide;

1,2,3,4-tetrahydro-N-methoxy-N,3-dimethyl-1-(2-methylpropyl)-2,4-dioxo-6-[(2,3-dihydro-3-methyl-2-oxo-1H-benzimidazol-1-yl]methyl)-thieno[2,3-d]pyrimidine-5-carboxamide;

6-[(2,3-dihydro-2-oxo-benzothiazol-3-yl)methyl]-1,2,3,4-tetrahydro-N-methoxy-N,3-dimethyl-1-(2-methylpropyl)-2,4-dioxo-thieno[2,3-d]pyrimidine-5-carboxamide;

6-[(1-acetyl-1H-indol-3-yl)methyl]-1,2,3,4-tetrahydro-N-methoxy-N,3-dimethyl-1-(2-methylpropyl)-2,4-dioxothieno[2,3-d]pyrimidine-5-carboxamide;

1,2,3,4-tetrahydro-N-methoxy-N,3-dimethyl-1-(2-methylpropyl)-6-[(2-methyl-1H-pyrrolo[2,3-b]pyridin-3-yl)methyl]-2,4-dioxo-thieno[2,3-d]pyrimidine-5-carboxamide;

6-[(3-chloroquinolin-4-yl)methyl]-1,2,3,4-tetrahydro-N-methoxy-N,3-dimethyl-1-(2-methylpropyl)-2,4-dioxo-thieno[2,3-d]pyrimidine-5-carboxamide;

N-methoxy-N,3-dimethyl-2,4-dioxo-1-propyl-6-(quinolin-4-ylmethyl)-1,2,3,4-tetrahydrothieno[2,3-d]pyrimidine-5-carboxamide;

1-ethyl-N-methoxy-N,3-dimethyl-2,4-dioxo-6-(quinolin-4-ylmethyl)-1,2,3,4-tetrahydrothieno[2,3-d]pyrimidine-5-carboxamide;

1-(cyclopropylmethyl)-N-methoxy-N,3-dimethyl-2,4-dioxo-6-(quinolin-4-ylmethyl)-1,2,3,4-tetrahydrothieno[2,3-d]pyrimidine-5-carboxamide;

1,2,3,4-tetrahydro-N-methoxy-N,3-dimethyl-6-[(2-methyl-1H-indol-3-yl)methyl]-1-(2-methylpropyl)-2,4-dioxothieno[2,3-d]pyrimidine-5-carboxamide;

1,2,3,4-tetrahydro-N-methoxy-N,3-dimethyl-6-[2-methyl-1H-indol-3-ylmethyl]-1-(2-methylpropyl)-2,4-dioxothieno[2,3-d]pyrimidine-5-carboxamide;

N-methoxy-N,3-dimethyl-2,4-dioxo-1-propyl-6-(quinolin-4-ylmethyl)-1,2,3,4-tetrahydrothieno[2,3-d]pyrimidine-5-carboxamide;

1-ethyl-N-methoxy-N,3-dimethyl-2,4-dioxo-6-(quinolin-4-ylmethyl)-1,2,3,4-tetrahydrothieno[2,3-d]pyrimidine-5-carboxamide;

1-(cyclopropylmethyl)-N-methoxy-N,3-dimethyl-2,4-dioxo-6-(quinolin-4-ylmethyl)-1,2,3,4-tetrahydrothieno[2,3-d]pyrimidine-5-carboxamide;

6-[4,5-dichloro-2-(hydroxymethyl)-1H-imidazol-1-ylmethyl]-1,2,3,4-tetrahydro-N-methoxy-N,3-dimethyl-1-(2-methyl propyl)-2,4-dioxo-thieno[2,3-d pyrimidine-5-carboxamide;

1,2,3,4-tetrahydro-N-methoxy-N,3-dimethyl-6-[2-methyl-1H-pyrrolo[2,3-b]pyridin-3-ylmethyl]-2,4-dioxo-1-propyl-thieno[2,3-d]pyrimidine-5-carboxamide;

1,2,3,4-tetrahydro-N-methoxy-N,3-dimethyl-1-(1-methyl-ethyl)-6-[2-methyl-1H-pyrrolo[2,3-b]pyridin-3-ylmethyl]-2,4-dioxo-thieno[2,3-d]pryimidine-5-carboxamide;

1,2,3,4-tetrahydro-N-methoxy-N,3-dimethyl-1-(2-methylpropyl)-2,4-dioxo-6-[2-(trifluoromethyl)phenylmethyl]thieno[2,3-d]pyrimidine-5-carboxamide;

1,2,3,4-tetrahydro-N-methoxy-N,3-dimethyl-1-(2-methylpropyl)-2,4-dioxo-6-(benzyl)thieno[2,3-d]pyrimidine-5-carboxamide;

methyl 4-[1,2,3,4-tetrahydro-5-[(N-methoxy-N-methylamino)carbonyl]-3-methyl-1-(2-methylpropyl)-2,4-dioxothieno[2,3-d]pyrimidin-6-yl](hydroxy)methyl]-1-methyl-1H-pyrrole-2-carboxylate;

methyl 1-methyl-4-[1,2,3,4-tetrahydro-5-[(methoxymethylamino)carbonyl]-3-methyl-1-(2-methylpropyl)-2,4-dioxothieno[2,3-d]pyrimidin-6-ylmethyl]-1H-pyrrole-2-carboxylate;

methyl 2,5-dimethyl-4-[1,2,3,4-tetrahydro-5-[(N-methoxy-N-methyl amino)carbonyl]-3-methyl-1-(2-methylpropyl)-2,4-dioxothieno[2,3-d]pyrimidin-6-ylmethyl]-1H-pyrrole-3-carboxylate;

1,2,3,4-tetrahydro-N-methoxy-N,3-dimethyl-1-(2-methylpropyl)-2,4-dioxo-6-[2-oxo-3(2H)-benzoxazolylmethyl]-thieno[2,3-d]pyrimidine-5-carboxamide;

1,2,3,4-tetrahydro-N-methoxy-N,3-dimethyl-1-(2-methylpropyl)-2,4-dioxo-6-[(2,4,5-trichloro-1H-imidazol-1-yl)methyl]-thieno[2,3-d]pyrimidine-5-carboxamide;

6-[4,5-dichloro-2-methyl-1H-imidazol-1-ylmethyl]-N-(2-hydroxyethyl)-1-isobutyl-N-methoxy-3-methyl-2,4-dioxo-1,2,3,4-tetrahydrothieno[2,3-d]pyrimidine-5-carboxamide;

6-[4,5-dichloro-2-methyl-1H-imidazol-1-ylmethyl]-N-(2-hydroxyethoxy)-1-isobutyl-N,3-dimethyl-2,4-dioxo-1,2,3,4-tetrahydrothieno[2,3-d]pyrimidine-5-carboxamide; and 6-[4,5-dichloro-2-methyl-1H-imidazol-1-ylmethyl]-N-ethyl-1,2,3,4-tetrahydro-N-methoxy-3-methyl-1-(2-methylpropyl)-2,4-dioxo-thieno[2,3-d]pyrimidine-5-carboxamide;

and pharmaceutically-acceptable salts thereof.

Synthesis of Compounds of the Formula 1

Compounds of formula 1 may be prepared by a number of processes as generally described hereinbelow and more specifically in the Examples hereinafter. Processes for the preparation of novel compounds of formula 1, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus according to another aspect of the invention, a compound of the formula (1) may be formed by deprotecting a compound of the formula (1) wherein at least 1 functional group is protected. For example, amino or hydroxy groups may be protected during the reaction sequence used to prepare a compound of the formula (1).

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a tri-(1-4C)alkylsilyl group (especially trimethylsilyl or tert-butyldimethylsilyl), an aryldi-(1-4C)alkylsilyl group (especially dimethylphenylsilyl), a diaryl-(1-4C)alkylsilyl group (especially tert-butyldiphenylsilyl), a (1-4C)alkyl group (especially methyl), a (2-4C)alkenyl group (especially allyl), a (1-4C)alkoxymethyl group (especially methoxymethyl) or a tetrahydropyranyl group (especially tetrahydroyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryldialkylsilyl group such as a tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, in particular, tetrabutylammonium fluoride. Alternatively an alkyl group may be removed, for example, by treatment with an alkali metal (1-4C)alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a (2-4C)alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

The protection and deprotection of functional groups is fully described in 'Protective Groups in Organic Chemistry', edited by J. W. F. McOmie, Plenum Press (1973) and 'Protective Groups in Organic Synthesis', $2^{nd}$ edition; T. W. Greene and P. G. M. Wuts, Wiley-Interscience (1991).

A compound of the formula (1), or a compound of the formula (1) wherein at least 1 functional group is protected, may be prepared using one of the following processes:

a) when $R^3$ is of the formula $CON(R^{10})Y(R^{11})$, reacting a compound of the formula (10):

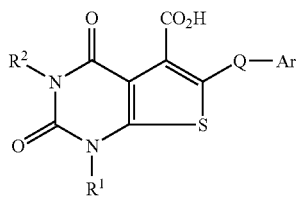
(10)

with a compound of the formula $HN(R^{10})Y(R^{11})$;

b) when $R^3$ is of the formula $-SO_2N(R^{10})Y(R^{11})$, reacting a compound of the formula (11):

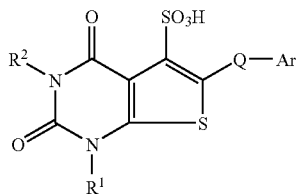
(11)

with a compound of the formula $HN(R^{10})Y(R^{11})$;

c) when Q is methylene, reacting a compound of the formula (12):

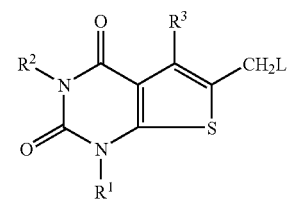
(12)

with a compound of the formula Ar;

d) when Q is methylene, reducing a compound of the formula (13):

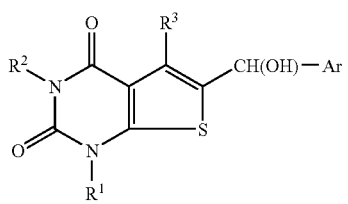
(13)

e) reacting a compound of the formula (14):

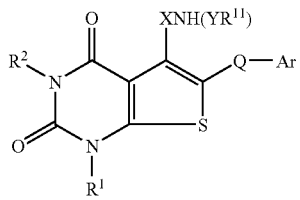
(14)

with a compound of the formula $L'-R^{10}$; or f) converting one compound of the formula (1) into another compound of the formula (1); wherein L and L' are leaving groups, X is —CO— or —SO$_2$— and $R^1$, $R^2$, $R^3$, $R^{10}$, Q and Ar are as hereinabove defined and any functional groups are optionally protected;

and optionally after a), b), c), d), e) or f), converting the compound of the formula (1) into a further compound of formula (1) and/or forming a pharmaceutically-acceptable salt, solvate and/or prodrug thereof.

The reaction between a compound of the formula (10) and $HN(R^{10})Y(R^{11})$ is conveniently carried out under amide bond forming reaction conditions. For example, in the presence of a coupling agent such as dicyclohexylcarbodiimide or 1-ethyl-3-(3-dimethylaminopropyl)ethylcarbodiimide. Optionally a base may be used, preferably an organic base such as triethylamine. Suitable solvents are usually aprotic solvents, for example dimethylformamide or chlorinated solvents, for example dichloromethane or trichloromethane. Additionally, a compound which catalyses this type of amide bond formation reaction, such as 1-hydroxybenzotriazole, may be present. The temperature is usually in the range of about −30° C. to about 60° C., preferably at or near ambient temperature.

The reaction between a compound of the formula (11) and $HN(R^{10})Y(R^{11})$ is conveniently carried out by converting the compound of formula (11) into the corresponding sulphonyl halide, preferably sulphonyl chloride. This may be achieved by using a halogenating agent, for example phosphorous trichloride or phosphorous pentachloride, in a halocarbon solvent, in a temperature range of −10° C. to 50° C. The resulting sulphonyl chloride may be reacted with the amine in a halocarbon solvent in the presence of an organic base, such as a tertiary amine, in the temperature range of 0° C. to 60° C., most conveniently at ambient temperature.

The reaction between a compound of the formula (12) and Ar is normally carried out in the presence of a strong base such as sodium hydride. Suitable leaving groups include halo, in particular bromo. The reaction is conveniently carried out in an inert solvent such as tetrahydrofuran, preferably at or around ambient temperature. In some circumstances, for example when Ar contains ring nitrogen atoms which do not need to be deprotonated, a milder base, such as sodium bicarbonate can be used. This reaction is conveniently used to prepare compounds in which Ar is linked through a ring nitrogen atom. However, it is possible to use this process to prepare a compound in which Ar is linked via a ring carbon atom. This can be achieved by using a strong base and a zinc salt such as zinc chloride and optionally sodium iodide as a catalyst.

A compound of formula (13) can be reduced to the corresponding methylene compound using standard reduction conditions for hydroxy groups known in the art. For example, it can be protonated with an acid such as trifluoroacetic acid and reduced with a trialkylsilane. Alternatively the hydroxy group could be converted to a stronger leaving group, such as mesylate or tosylate and the resulting compound hydrogenated in a non-hydroxylic solvent, preferably tetrahydrofuran, with a catalyst such as palladium on charcoal, in a temperature range of 0° C. to 50° C., preferably at ambient temperature and a pressure of 1 to 5 bar.

The reaction between a compound of formula (14) and a compound of formula $L'-R^{10}$ is conveniently carried out in an organic solvent such as acetone or THF in the presence of a mild base, for example an inorganic base such as potassium carbonate. The reaction may be carried out in the temperature range of 0° C. to reflux. In particular the leaving group, L', is halo, for example iodo.

A compound of the formula (1) may be prepared from another compound of formula (1) by chemical modification. For example a compound of the formula (1) wherein Q is methylene can be oxidised to a compound of the formula (1) wherein Q is carbonyl. A preferred oxidising agent is 2,3-dichloro-5,6-dicyano-1,4-benzoquinone (DDQ) in an inert organic solvent such as tetrahydrofuran. In some circumstances oxidation can be effected by exposure of the methylene compound to air.

Intermediates of the formulae (10), (11) and (12) may be formed from a compound of the formula (15):

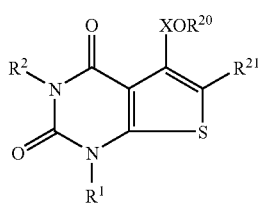

(15)

wherein $R^{20}$ is $C_{1-6}$alkyl, for example methyl or ethyl, and $R^{21}$ is either —$CH_2L$ (wherein L is as hereinabove defined) or —CH(OH)Ar.

A compound of formula (15) wherein $R^{21}$ is —$H_2L$ may be reacted with Ar under similar conditions to those described for process c) above.

When Ar is linked via a ring carbon atom in a compound of the formula (10), (11) or (12), a compound of formula (15) wherein $R^{21}$ is —CH(OH)Ar may be reduced using similar conditions to those described for process d) above. To form a compound of the formula (12), —$XOR^{20}$ is then converted to $R^3$ by removing $R^{20}$ and using process a) or b) described above as appropriate.

A compound of the formula (13) or (15) wherein $R^{21}$ is —CH(OH)Ar may be formed by reacting a compound of the formula (16):

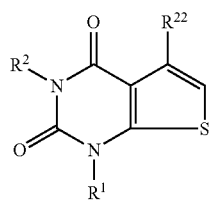

(16)

(wherein $R^{22}$ is $R^3$ or —$CO_2R^{20}$, as appropriate) with a compound of formula Ar—CHO in the presence of a strong base such as a lithium dialkylamide, for example, lithium diisopropylamide, in an inert organic solvent such as tetrahydrofuran and initially at a low temperature, such as −78° C. and subsequently allowing it to warm to ambient temperature.

A compound of formula (14) may be formed by reacting a compound of formula (10) or (12) with a compound of formula $H_2N(YR^{11})$ under the reaction conditions described in a) or b) as appropriate.

The intermediates (15) are in general prepared from a compound of the formula (17):

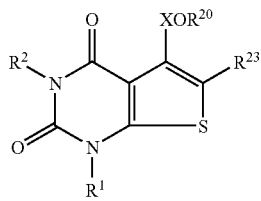

(17)

wherein $R^{23}$ is hydrogen or methyl.

A compound of the formula (15), wherein $R^{21}$ is —CH (OH)Ar, may be prepared by reacting a compound of formula (17), wherein $R^{23}$ is hydrogen, with Ar—CHO using the conditions described above for the reaction of a compound of formula (16) with a compound of formula Ar—CHO.

A compound of the formula (15), wherein $R^{21}$ is —$CH_2L$, may be prepared from a compound of formula (17), wherein $R^{23}$ is methyl, by, for example, halogenation. When L is bromo, the methyl group may be brominated using a standard brominating agent such as N-bromosuccinimide under standard conditions known in the art.

A compound of formula (17), wherein X is —CO— and $R^{23}$ is hydrogen, may be formed by firstly reacting a compound of formula (18):

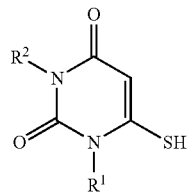

(18)

with an alkylbromopyruvate, such as ethylbromopyruvate, in the presence of a mild base such as an alkali carbonate, for example potassium carbonate in a polar solvent e.g. DMF at a temperature between 5° C. and 50° C. and then secondly treating the resulting adduct with a Lewis acid preferably titanium tetrachloride, in an inert solvent e.g. dichloromethane at a temperature between −20° C. and 50° C., preferably between 0° C. and 25° C.

A compound of formula (17), wherein X is —CO— and $R^{23}$ is methyl, may be formed by firstly reacting a compound of formula (18) with an alkyl 3-bromo-2-oxobutanoate such as methyl 3-bromo-2-oxobutanoate in the presence of a mild base such as an alkali carboxylate, for example sodium acetate in a polar solvent such as DMF, or preferably water, at a temperature between 5° C. and 50° C. and then secondly treating the resulting adduct with a Lewis acid, preferably titanium tetrachloride, in an inert solvent e.g. dichloromethane at a temperature between −20° C. and 50° C., preferably between 0° C. and 25° C.

A compound of formula (17), wherein X is —CO—, may also be formed by reacting a compound of formula (19):

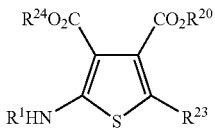

(19)

(wherein $R^{24}$ is $C_{1-4}$alkyl, for example ethyl)

with acetyl cyanate in an inert solvent, for example toluene, at a temperature of from 0° C. to 50° C., and then treating the product of that conversion with a solution of a metal alkoxide in the alkanol (eg sodium methoxide in methanol) at a temperature of from 0° C. to 30° C., in the presence of a compound of formula $R^2-L^1$ (wherein $L^1$ is a leaving group, eg iodide).

A compound of formula (19) may be prepared by the reaction of a compound of formula (20):
$R^1-N=S$ with a Wittig compound, for example a compound of the formula (21):

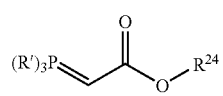
(21)

(wherein R' is phenyl or substituted phenyl such as tolyl) in an inert solvent, for example THF, at a temperature of from 20° C. to 80° C., and treatment of the resulting adduct in situ with a compound of formula (22):

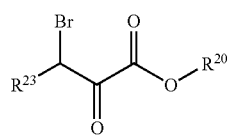
(22)

at a temperature of from −78° C. to 60° C.

Compounds of the formula (11) and (12) and (13) wherein $R^3$ is of the formula $-SO_2N(R^{10})Y(R^{11})$ may be prepared using related methods known in the art.

The compounds of formula (1) above may be converted to a pharmaceutically-acceptable salt, solvate or prodrug thereof.

The skilled person will appreciate that it may sometimes be necessary to protect functional groups in the intermediates during reaction to prevent side-reactions. The texts referred to previously in the discussion on protecting group give guidance on suitable protecting groups and their introduction and removal.

Certain compounds of formula (1) are capable of existing in stereoisomeric forms. It will be understood that the invention encompasses all geometric and optical isomers of the compounds of formula (1) and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease; and (7) cancer.

Accordingly, the present invention provides a compound of formula (1) or a pharmaceutically-acceptable salt thereof as hereinbefore defined for use in therapy.

In another aspect, the present invention provides a compound of formula (1) or a pharmaceutically-acceptable salt thereof as hereinbefore defined for use in inhibiting the proliferation of T cells.

In another aspect, the invention provides the use of a compound of formula (1) or a pharmaceutically-acceptable salt thereof as hereinbefore defined in the manufacture of a medicament for use in inhibiting the proliferation of T cells.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (1) or a pharmaceutically-acceptable salt thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (1) or a pharmaceutically-acceptable salt thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (1) will be in the range from 0.1 mg/kg, particularly from 0.3 mg/kg, more particularly from 0.5 mg/kg and still more particularly from 1 mg/kg up to and including 30 mg/kg. For the treatment of airways diseases, the daily dosage of the compound of formula (1) will typically be in the range from 0.001 mg/kg to 30 mg/kg.

The compounds of formula (1) and pharmaceutically-acceptable salts thereof may be used on their own but will generally be administered in the form of a pharmaceutical is composition in which the formula (1) compound/salt/solvate (active ingredient) is in association with a pharmaceutically-acceptable adjuvant, diluent or carrier. Depending on the mode of administration, the pharmaceutical composition will particularly comprise from 0.05 to 99% w (percent by weight), more particularly less than 80% w, e.g. from 0.10 to 70% w, and even more particularly less than 50% w, of active ingredient, all percentages by weight being based on total composition.

Thus, the present invention also provides a pharmaceutical composition comprising a compound of formula (1) or a pharmaceutically-acceptable salt thereof as hereinbefore defined, in association with a pharmaceutically-acceptable adjuvant, diluent or carrier.

The invention further provides a process for the preparation of a pharmaceutical composition of the invention which comprises mixing a compound of formula (1) or a pharmaceutically-acceptable salt thereof as hereinbefore defined, with a pharmaceutically-acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The ability of compounds which can inhibit PMA/ionomycin-stimulated peripheral blood mononuclear cell proliferation can be assessed, for example using the procedure set out below:

Inhibition of PMA/Ionomycin-Stimulated Peripheral Blood Mononuclear Cell Proliferation The assay for Phorbol 12-myristate 13-Acetate (PMA)/ionomycin-stimulated peripheral blood mononuclear cell (PBMC) proliferation was performed in 96-well flat bottomed microtitre plates. Compounds were prepared as 10 mM stock solutions in dimethyl sulfoxide. A 50-fold dilution of this was prepared in RPMI culture medium and serial diutions were prepared from this solution. 10 µl of the 50-fold diluted stock, or dilutions of it, were added to the well to give concentrations in the assay starting at 9.5 µM and going down. Into each well was placed $1 \times 10^5$ PBMC, prepared from human peripheral blood from a single donor, in RPMI1640 medium supplemented with 10% human serum, 2 mM glutamine and penicillin/streptomycin. PMA (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 µCi) was added for the final 6 hours of the incubation. The level of radioactivity incorporated by the cells was then determined and this is a measure of proliferation.

The compounds of the Examples were found to exhibit an $IA_{50}$ value of less than $1 \times 10^{-6}$ M in the above test. In the following specific examples, Example 2 had an $IA_{50}$ of $5.88 \times 10^{-9}$ M and Example 7 had an $IA_{50}$ of $3.46 \times 10^{-8}$ M in the above test.

The invention will now be illustrated in the following Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon or nitrogen;

(iii) yields are given for illustration only and are not necessarily the maximum attainable;

(iv) the structures of the end-products of the formula (1) were confirmed by nuclear (generally proton) magnetic resonance (NMR) and mass spectral techniques; proton magnetic resonance chemical shift values were measured on the delta scale and peak multiplicities are shown as follows: S, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), mass spectrometry (MS), infra-red (IR) or NMR analysis;

| Abbreviations | |
|---|---|
| 2,3-Dichloro-5,6-dicyano-1,4-benzoquinone | DDQ |
| Dimethylformamide | DMF |
| m-Chloroperoxybenzoic acid | mCPBA |
| Tetrahydrofuran | THF |

EXAMPLE 1

6-[4,5-Dichloro-2-methyl-1H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide a) Methyl 1,2,3,4-tetrahydro-3,6-dimethyl-1-(2-methylpropyl)-2,4-dioxo-thieno-[2,3-d]pyrimidine-5-carboxylate 6-Mercapto-3-methyl-1-(2-methylpropyl)-pyrimidine-2,4 (1H,3H)-dione (50 g) was dissolved in a solution of sodium acetate (95.6 g) in water (1.5 L), and methyl 3-bromo-2-oxo-butanoate (44.6 g) was added dropwise with stirring.

After stirring 1 h at room temperature the mixture was thoroughly extracted into ethyl acetate. The organic solution was washed with brine, dried (MgSO$_4$) and evaporated to leave an oil.

The oil (75.1 g) was dissolved in methylene chloride (800 ml) and cooled in an ice-bath under an atmosphere of nitrogen. With efficient stirring titanium tetrachloride (43.3 ml) was slowly added dropwise. The reaction mixture was stirred 1 hr in the ice-bath and then 3 hr at room temperature. The reaction mixture was poured slowly into vigorously stirred ice-water (2 L), and then the resulting suspension was extracted into methylene chloride. After drying, the organic solvent was removed in vacuo, and the residue was chromatographed (SiO$_2$/1:1 ethyl acetate-isohexane) to afford the sub-title compound (42 g). Trituration with isohexane gave a white powder.

δ $^1$H$_{CDCl3}$ 0.98(6H,d), 2.23-2.41(1H,m), 2.46(3H,s), 3.4 (3H,s), 3.75(2H,d), 3.96(3H,s).

b) Methyl 6-(bromomethyl)-1,2,3,4-tetrahydro-3-methyl-1-(2-methylpropyl)-2,4-dioxo-thieno[2,3-d]pyrimidine-5-carboxylate A solution of the product of step a) (10 g) and N-bromosuccinimide (5.74 g) in chloroform (350 ml) was refluxed under illumination from a tungsten lamp for 4 h. The solution was washed with water, saturated sodium bicarbonate solution and then brine. The organic layer was dried over magnesium sulfate, filtered and concentrated concentrated in vacuo. The residue was purified by flash silica chromatography eluting with isohexane:ether (1:1) to give the sub-title compound as a white powder (8.29 g).

MS (APCI) 390/391 [M+H]$^+$ δ $^1$H$_{CDCl3}$ 1.00(6H,d), 2.31 (1H,septet), 3.39(3H,s), 3.76(2H,dd), 3.99(3H,s), 4.66(2H, s).

c) Methyl 6-[4,5-dichloro-2-methyl-1H-imidazol-1-ylmethyl]-1,2,3,4-tetrahydro-3-methyl-1-(2-methylpropyl)-2,4-dioxo-thieno[2,3-d]pyrimidine-5-carboxylate 4,5-Dichloro-2-methylimidazole (1.3 g) in dry tetrahydrofuran (20 ml) was added dropwise to a suspension of sodium hydride (0.34 g, 60%) in dry tetrahydrofuran (20 ml) at room temperature under nitrogen. After 15 min, a solution of the product of step b) (3.35 g) in dry tetrahydrofuran (20 ml) was added dropwise and the reaction was stirred for 3 h at room temperature. The solution was poured into water and extracted with ethyl acetate. The combined extracts were dried over magnesium sulfate, filtered and concentrated in vacuo. The residue was purified by flash silica chromatography eluting with a gradient 50-100% ethyl acetate in isohexane to give the sub-title compound as a white solid (2.28 g).

MS (APCI) 459/460 [M+H]$^+$ δ $^1$H$_{CDCl3}$ 0.97(6H,d), 2.26 (1H, septet), 2.38(3H,s), 3.39(3H,s), 3.73(2H,d), 3.99(3H,s), 5.26(2H,s).

d) 6-[4,5-Dichloro-2-methyl-]1H-imidazol-1-ylmethyl]-1,2,3,4-tetrahydro-3-methyl-1-(2-methylpropyl)-2,4-dioxo-thieno[2,3-d]pyrimidine-5-carboxylic acid Sodium hydroxide (7.3 ml of 1M aqueous solution) followed by methanol (4 ml) were added to a solution of the product of step c) (2.28 g) in tetrahydrofuran (50 ml) and stirred at room temperature for 3 hours. The solution was concentrated under reduced pressure. The residue was diluted with water and extracted with ethyl acetate. The combined extracts were dried over magnesium sulfate, filtered and concentrated concentrated in vacuo. The residue was purified by flash silica chromatography eluting with a gradient of 2-5% ethanol in dichloromethane to give the sub-title compound as a white solid (1.68 g).

MS (APCI) 445/447 [M+H]$^+$ δ $^1$H$_{CDCl3}$ 0.96(6H,d), 2.22 (1H, septet), 2.37(3(2H,d), 5.78(2H,s), 15.51 (1H,br.s).

e) 6-[4,5-Dichloro-2-methyl-1H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide 1-Hydroxybenzotriazole (0.077 g) was added to a solution of the product of step d) (0.128 g) in dichloromethane (20 ml). After stirring for 10 min, 1-ethyl-3-(3'-dimethylaminopropyl)-carbodiimide hydrochloride (0.11 g) was added. After stirring for 30 minutes N,O-dimethylhydroxylamine hydrochloride (0.056 g) and triethylamine (0.08 ml) were added and stirring was continued for 20 h. The solution was concentrated in vacuo. The residue was purified by flash silica chromatography eluting with a gradient of 0-10% ethanol in dichloromethane to give the title compound as a white foam (0.095 g).

MS(ESI) 488.09 [M+H]$^+$ δ $^1$H$_{CDCl3}$ 0.97-0.99(6H,m), 2.26(1H, septet), 2.40+2.43(2×s ratio 3:1, 3H), 3.39(3H,s), 3.11+3.43(2×s ratio 1:3, 3H), 3.49+3.97(2×s, ratio3:1, 3H), 3.65(1H,dd), 3.84(1H,d), 5.10-5.23(2H,m).

EXAMPLE 2

1,2,3,4-Tetrahydro-N-methoxy-N,3-dimethyl-1-(2-methylpropyl)-2,4-dioxo-6-(4-quinolinylmethyl) thieno[2,3-d]pyrimidine-5-carboxamide a) Ethyl 1,2,3,4-tetrahydro-3-methyl-1-(2-methylpropyl)-2,4-dioxo-thieno[2,3-d]pyrimidine-5-carboxylate 6-Mercapto-3-methyl-1-(2-methylpropyl)-pyrimidine-2,4 (1H,3H)-dione (49.5 g) was dissolved in dry DMF (900 ml) and ethyl bromopyruvate (30 ml) was added, and then with stirring anhydrous potassium carbonate (15.954 g) was also added. The mixture was stirred at room temperature for 5 h, and then poured into water (5 L). The aqueous solution was acidified with dil hydrochloric acid, and then extracted thoroughly with ethyl acetate. The organic extract was dried (MgSO$_4$) and evaporated at high vacuum to leave a semisolid mass. A portion of this semisolid mass (24 g) was dissolved in methylene chloride (500 ml) and cooled in an ice-bath under an atmosphere of nitrogen. With efficient stirring titanium tetrachloride (13.5 ml) was slowly added. The reaction mixture was stirred 1 h in the ice-bath and then 3 h at room temperature. The reaction mixture was poured slowly into vigorously stirred ice-water (1.5 L), and then the resulting suspension was extracted into methylene chloride. After drying the organic solvent was concentrated in vacuo, and the residue was chromatographed (SiO$_2$/1:1 ethyl acetate-isohexane) to afford the sub-title compound as a pale yellow solid (15 g).

δ $^1$H$_{CDCl3}$ 1.0(6H, d), 1.4(3H, t), 2.31-2.45(1H,m), 3.4 (3H,s), 3.8(2H,d), 4.4(2H,q), 7.28(1H,s).

b) Ethyl 1,2,3,4-tetrahydro-6-(hydroxy 4-quinolinylmethyl)-3-methyl-1-(2-methylpropyl)-2,4-dioxo-thieno[2,3-d]pyrimidine-5-carboxylate A solution of lithium diisopropylamide (5.52 g) in anhydrous THF (80 ml) was added dropwise over 1 h to a stirred solution of the product of step a) (8.02 g) and 4-quinolinecarboxaldehyde (8.12 g) in anhydrous THF (80 ml) at −78°

C. under nitrogen. The mixture was stirred for a further 1 h at −78° C. then quenched with glacial acetic acid (10 ml), allowed to warm to room temperature, diluted with saturated sodium bicarbonate solution (100 ml) and extracted into ethyl acetate (2×100 ml). The combined extracts were dried over magnesium sulfate, filtered and concentrated in vacuo. The residue was purified by column chromatography, eluting with 3:2 ethyl acetate/i-hexane, to give the sub-title compound as a white solid (7.35 g).

MS (ESI) 468 {M+H}+ δ $^1H_{CDCl_3}$ 0.85 (3H,d), 0.88 (3H,d), 1.43 (3H,t), 2.10-2.16 (1H,m), 3.38 (3H,s), 3.49 (1H,dd), 3.61 (1H,s,br), 3.71 (1H,dd), 4.48 (2H,quartet), 6.78 (1H,s), 7.52 (1H,t), 7.72 (1H,t), 7.83 (1H,d), 7.90 (1H,d), 8.17 (1H,d), 9.02 (1H,d)

c) Ethyl 1,2,3,4-tetrahydro-3-methyl-1-(2-methylpropyl)-2,4-dioxo-6-(4-quinolinylmethyl)-thieno[2,3-d]pyrimidine-5-carboxylate Trifluoroacetic anhydride (3.33 ml) was added to a solution of the product of step b) (7.34 g) and triethylamine (6.56 ml) in anhydrous THF (150 ml) at room temperature under nitrogen and the mixture stirred for 15 min. 10% palladium on charcoal (500 mg) was added and the mixture hydrogenated at 1 bar for 20 h. It was filtered through Celite, washing with saturated sodium bicarbonate solution (150 ml) then ethyl acetate (300 ml). The organic material was extracted into ethyl acetate (150 ml), the combined extracts were dried over magnesium sulfate, filtered and concentrated in vacuo. The residue was purified by column chromatography, eluting with 1:1 ethyl acetate/i-hexane, to give the sub-title compound as a solid (5.90 g).

MS (ESI) 452{M+H}+ δ $^1H_{CDCl_3}$ 0.90 (6H,d), 1.37 (3H,t), 2.10-2.16 (1H,m), 3.39 (3H,s), 3.64 (2H,d), 4.45 (2H,q), 4.61 (2H,s), 7.29 (1H,d), 7.60 (1H,t), 7.75 (1H,t), 8.11 (1H,d), 8.16 (1H,d), 8.89 (1H,d)

d) Sodium 1,2,3,4-tetrahydro-3-methyl-1-(2-methylpronyl)-2,4-dioxo-6-(4-quinolinylmethyl)-thieno[2,3-d]pyrimidine-5-carboxylate A solution of the product of step c) (5.89 g) in THF (150 ml) and methanol (23 ml) under nitrogen was degassed by repeated evacuation and flushing with nitrogen. 1M sodium hydroxide (18 ml) was added and the mixture stirred for 18 h. The resulting precipitated solid was collected by filtration, washed with THF and concentrated in vacuo to give the sub-title compound as a solid (5.06 g).

MS (ESI) 424{M+H}+ δ $^1H_{DMSO}$ 0.81 (6H,d), 2.10-2.15 (1H,m), 3.20 (3H,s), 3.56 (2H,d), 4.56 (2H,s), 7.52 (1H,dd), 7.57 (1H,td), 7.74 (1H,td), 8.00 (1H,dd), 8.83 (1H,d)

e) 1,2,3,4-Tetrahydro-N-methoxy-N,3-dimethyl-1-(2-methylpropyl)-2,4-dioxo-6-(4-quinolinylmethyl)-thien[2,3-d]pyrimidine-5-carboxamide To a suspension of the product of step d) (157 mg) in dichloromethane (5 ml) was added 1-hydroxybenzotriazole hydrate (108 mg) and the mixture stirred for 15 minutes. 1-Ethyl-3-(3'-dimethylaminopropyl)carbodiimide hydrochloride (135 mg) was added and stirring continued for 1 h. N,O-Dimethylhydroxylamine hydrochloride (69 mg) and triethylamine (147 μl) were added and the reaction mixture stirred for 18 h then concentrated in vacuo. The residue was purified by column chromatography, eluting with i-hexane/ethyl acetate (10-100% gradient) to give the title compound as a solid (136 mg).

MS (APCI) 467{M+H}+ δ $^1H_{DMSO}$ 0.83 (6H,m), 2.04-2.08(1H,m), 2.98 (1H,s), 3.21 (3H,s), 3.22-3.27 (2H,m), 3.43 (2H,s), 3.61 (2H,d), 3.72 (1H,s), 4.60 (2H,s), 7.43-7.48 (1H,m), 7.61-7.68 (1H,m), 7.78 (1H,t), 8.04 (1H,d), 8.22-8.31 (1H,m), 8.67 (1H,d)

EXAMPLE 3

1,2,3,4-Tetrahydro-N-methoxy-N,3-dimethyl-1-(2-methylpropyl)-2,4-dioxo-6-(1H-pyrrolo[2,3-b]pyridin-3-ylmethyl)-thieno[2,3-d]pyrimidine-5-carboxamide a) Methyl 1,2,3,4-tetrahydro-3-methyl-1-(2-methylpropyl)-2,4-dioxo-6-(1H-pyrrolo[2,3b]pyridin-3-ylmethyl)-thieno[2,3,d]pyrimidine-5-carboxylate To a solution of 7-azaindole (0.78 g) in dry THF (30 ml) was added 2.5M n-butyl lithium (2.6 ml) dropwise at 10° C. under nitrogen and the resulting mixture was stirred for 15 min. 1.0M ethereal zinc chloride (6.61 ml) was added, the mixture allowed to warm to room temperature and stirred for 2 hours. The solvent was removed under reduced pressure and the residue diluted with dry toluene (20 ml). A solution of the product of example 1 part a) (3.14 g) in dry toluene (10 ml) was added followed by a catalytic amount of sodium iodide and the mixture stirred under nitrogen for 72 h. The solvent was decanted and the solid residue partitioned between 2N hydrochloric acid and ethyl acetate; the aqueous phase was basified with sodium bicarbonate and extracted into ethyl acetate (2×10 ml). The combined extracts were dried over magnesium sulfate, filtered and concentrated in vacuo. The residue was purified by chromatography, eluting with i-hexane/ethyl acetate (20-75% gradient), to give the sub-title compound as a yellow solid (1.37 g).

MS (APCI) 427[M+H]+ δ $^1H_{DMSO}$ 0.83 (6H,d), 2.09 (1H, heptet), 3.20 (3H,s), 3.61 (2H,d), 3.86 (3H,s), 4.22 (2H,s), 7.02-7.05 (1H,m), 7.43 (1H,m), 7.88 (1H,d), 8.20 (1H,d), 11.56 (1H,s,br)

b) 1,2,3,4-Tetrahydro-3-methyl-1-(2-methylpropyl)-2,4-dioxo-6-(1H-pyrrolo[2,3b]pyridin-3-ylmethyl)-thieno[2,3d]pyrimidine-5-carboxylic acid The sub-title compound (1.22 g) was prepared from the product of part a, (1.37 g) by the method of example 1, step c.

MS (ESI) 413[M+H]+ c) 1,2,3,4-Tetrahydro-N-methoxy-N,3-dimethyl-1-(2-methylpropyl)-2,4-dioxo-6-(1H-pyrrolo[2,3-b]pyridin-3-ylmethyl)-thieno[2,3-d]pyrimidine-5-carboxamide The title compound (100 mg) was prepared from the product of part b), (145 mg) by the method of example 1, step d.

MS (APCI) 456[M+H]+ δ $^1H_{DMSO}$ 0.82-0.84 (6H,m), 2.07-2.10 (1H,m), 3.02 (1H,s), 3.20-3.22 (3H,m), 3.30-3.32 (2H,m), 3.44 (2H,s), 3.57-3.68 (2H,m), 3.78 (1H,s), 4.14-4.16 (2H,m), 7.01-7.04 (1H,m), 7.43 (1H,d), 7.95-7.97 (1H,m), 8.20 (1H,dd), 11.55 (1H,s,br)

EXAMPLE 4

1,2,3,4-Tetrahydro-6-(1H-indol-3-ylmethyl)-N-methoxy-N,3-dimethyl-1-(2-methylpropyl)-2,4-dioxo-thieno[2,3d]pyrimidine-5-carboxamide a) Methyl 1,2,3,4-tetrahydro-6-(1H-indol-3-ylmethyl)-3-methyl-1-(2-methylpropyl)-2,4-dioxo-thieno[2,3-d]pyrimidine-5-carboxylate The product from example 1 part b) (2.5 g) was dissolved in chloroform (20 ml), then indole (1.08 g), sodium hydrogen carbonate (1.4 g) and water (20 ml) were added and the reaction mixture was stirred at room temperature for 3 days. The two layers were separated and the aqueous phase was extracted with dichloromethane. The combined organic extracts were dried over magnesium sulfate, filtered and concentrated in vacuo. The residue was purified by flash silica chromatography eluting with 50% ethyl acetate in isohexane to give the sub-title compound as a white solid (1.8 g).

MS(APCI) 426 [M+H]$^+$ b) 1,2,3,4-Tetrahydro-6-(1H-indol-3-ylmethyl)-3-methyl-1-(2-methylpropyl)-2,4-dioxo-thieno[2,3-d]pyrimidine-5-carboxylic acid Prepared using the procedure described in example 1 part d) from the product of part a) to give the sub-title compound as a pale pink solid.

MS(APCI) 412 [M+H]$^+$ c) 1,2,3,4-Tetrahydro-6-(1H-indol-3-ylmethyl)-N-methoxy-N,3-dimethyl-1-(2-methylpropyl)-2,4-dioxo-thieno[2,3-d]pyrimidine-5-carboxamide Prepared using the procedure described in example 1 part e) from the product of part b) to give the title compound as a pale pink solid.

MS(APCI) 454 [M+H]$^+$

EXAMPLE 5

1,2,3,4-Tetrahydro-6-(1H-indol-3-ylcarbonyl)-N-methoxy-N,3-dimethyl-1-(2-methylpropyl)-2,4-dioxo-thieno[2,3-d]pyrimidine-5-carboxamide DDQ (0.25 g) was added to a stirred solution of the product of example 4 (0.25 g) in THF (9 ml) and water (1 ml). The solution was stirred for a further 2 h and the concentrated in vacuo. The residue was purified by flash silica chromatography eluting with ethyl acetate:isohexane (7:3) to give the title compound as a pale pink solid (0.1 g).

MS(APCI) 469 [M+H]$^+$ δ $^1$H$_{DMSO}$ 0.95-1.07(6H,m), 2.21-2.38(1H,m), 3.2(3H,s), 3.29(3H,s), 3.46(3H,s), 3.75-3.93(2H,m), 7.21-7.32(2H,m), 7.55(1H,d), 8.13(1H,d), 8.27-8.31(1H,m), 12.17(1H,s).

EXAMPLE 6

6-[4,5-Dichloro-2-methyl-1H-imidazol-1-ylmethyl]-1,2,3,4-tetrahydro-N-methoxy-N,3-dimethyl-1-(1-methylethyl)-2,4-dioxo-thieno[2,3-d]pyrimidine-5-carboxamide a) Ethyl methyl 2-methyl-5-((1-methylethyl)amino)-thiophene-3,4-dicarboxylate Ethoxycarbonylmethylene triphenyl phosphorane (33.8 g) in dry THF (200 ml) was treated with isopropyl isothiocyanate (10.1 g) at 65° C. for 16 h under nitrogen. The mixture was cooled to −78° C. and methyl 3-bromo-2-oxo-butanoate (19.5 g) was added. The reaction was allowed to warm slowly to room temperature. After 24 h at room temperature more methyl 3-bromo-2-oxo-butanoate (2.8 g) was added and the mixture was warmed to 60° C. for 16 h. The cooled reaction was poured into water (1.5 L) and extracted into ether. Drying and evaporation gave an oil which was chromatographed (SiO2/10:1 isohexane-ethyl acetate then 5:1 isohexane-ethyl acetate) to afford the subtitle compound (23.5 g).

δ $^1$H$_{CDCl3}$ 1.23-1.35(9H, m), 2.26(3H,s), 3.46(1H, m),3.82(3H, s),4.2(2H, q),7.42(1H, br.s)

b) Methyl 1,2,3,4-tetrahydro-3,6-dimethyl-1-(1-methylethyl)-2,4-dioxo-thieno[2,3-d]pyrimidine-5-carboxylate Silver cyanate (13.5 g) suspended in anhydrous toluene (90 ml) under nitrogen was treated dropwise with acetyl chloride (5.34 ml) and stirred vigorously for 30 min. The product of step a) (23 g) dissolved in anhydrous toluene (15 ml) was added and the mixture was stirred for 72 h. Ether (360 ml) was added and the insoluble material was filtered off and washed with a small volume of ether. The combined organic solutions were washed with saturated sodium bicarbonate solution, dried and evaporated. The residue was treated with a solution of sodium methoxide in methanol (25 wt %, 64 ml) at room temperature for 72 h. The reaction was cooled in ice and treated with trimethylsilyl chloride (50.8 ml) and stirred at room temperature overnight. All volatiles were removed in vacuo and the residue partitioned between water and ethyl acetate. Drying and evaporation of the organic solution left a residue, which was chromatographed (SiO$_2$/2:1 isohexane-ethyl acetate then 3:2 isohexane-ethyl acetate) to isolate the major component (12.2 g). This was taken in dry DMF (150 ml) with potassium carbonate (6.95 g) and methyl iodide (7.1 g) for 72 h at room temperature. The mixture was poured into water (2 L), acidified and extracted into ether. Washing with brine, drying and evaporation gave a solid which was boiled in isohexane (200 ml) containing ethyl acetate (3 ml). On cooling the precipitated pale yellow solid was collected and dried, to afford the sub-title compound (10.5 g).

δ $^1$H$_{CDCl3}$ 1.6(6H, d), 2.44(3H,s), 3.37(3H, s), 3.95(3H, s), 4.66(1H, br)

MS (APCI) (M$^+$+H)

c) 6-(Bromomethyl)-1,2,3,4-tetrahydro-3-methyl-1-(1-methylethyl)-2,4-dioxothieno[2,3-d]pyrimidine-5-carboxylic acid methyl ester Prepared using the procedure described in example 1 part b) from the product of example 6 part b) to give the subtitle compound.

δ $^1$H$_{CDCl3}$ 1.62-1.64(6H,m), 3.37(3H,s), 3.99(3H,s), 4.60.4.70(3H,m)

d) Methyl 6-[4,5-Dichloro-2-methyl-1H-imidazol-1-ylmethyl]-1,2,3,4-tetrahydro-3-methyl-1-(1-methylethyl)-2,4-dioxo-thieno[2,3-d]pyrimidine-5-carboxylate Prepared using the procedure described in example 1 part c) from the product of example 6 part c) to give the subtitle compound.

MS (APCI) 445/446 [M+H]$^+$ δ $^1$H CDCl3 1.56-1.61(6H, m), 2.37-2.38(3H,m), 3.37(3H,s), 3.98(3H,s), 4.40-4.50(1H, br.s), 5.25(2H,s).

e) Sodium 6-[4,5-Dichloro-2-methyl-1H-imidazol-1-yl)methyl]-1,2,3,4-tetrahydro-3-methyl-1-(1-methylethyl)-2,4-dioxo-thieno[2,3-d]pyrimidine-5-carboxylate Prepared using the procedure described in example 2 part d) from the product of example 6 part d) to give the sub-title compound.

MS (APCI) 431/433 [M+H]+ δ $^1H_{D_2O}$ 1.53(6H,d), 2.39 (3H,s), 3.31(3H,s), 3.54-3.69(1H,m), 5.32(2H,s).

f) 6-[4,5-Dichloro-2-methyl-1H-imidazol-1-ylmethyl]-1,2,3,4-tetrahydro-N-methoxy-N,3-dimethyl-1-(1-methylethyl)-2,4-dioxo-thieno[2,3-d]pyrimidine-5-carboxamide Prepared using the procedure described in example 1 part e) from the product of example 6 part e) to give the title compound.

MS (APCI) 474/475 [M+H]+ δ $^1H_{CDCl_3}$ 1.54-1.61(6H,m), 2.40-2.44(3H,m), 3.36(3H,s), 3.11 and 3.43(3H,2×s ratio 1:5), 3.49+3.97(3H,2×s ratio 5:1), 4.47(1H,br.s), 5.15-5.24 (2H,m).

EXAMPLE 7

6-[4,5-Dichloro-2-methyl-1H-imidazol-1-ylmethyl]-1,2,3,4-tetrahydro-N-methoxy-N,3-dimethyl-2,4-dioxo-1-propyl-thieno[2,3-d]pyrimidine-5-carboxamide

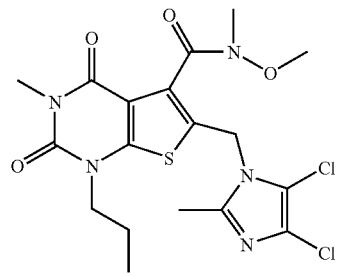

a) 6-Mercapto-3-methyl-1-propyl-pyrimidine-2,4 (1H,3H)-dione

A mixture of 6-chloro-3-methyl-1-propyl-pyrimidine-2,4 (1H,3H)-dione (3.76 g), sodium hydrosulphide hydrate (6.0 g) and ethanol (100 ml) was stirred at room temperature for 48 h then concentrated under reduced pressure. The residue was dissolved in water (500 ml) and washed with ethyl acetate (2×100 ml). The aqueous phase was acidified with dilute hydrochloric acid, then extracted with ethyl acetate (3×100 ml). The combined organic phase was dried (MgSO$_4$) and concentrated in vacuo to give a pale yellow solid which was used directly in the next step.

b) Methyl 1,2,3,4-tetrahydro-3,6-dimethyl-2,4-dioxo-1-propyl-thieno[2,3-d]pyrimidine-5-carboxylate Prepared from the product of step a) following the procedure of example 1, step a).

δ $^1H_{CDCl_3}$ 1.00(3H,t), 1.81(2H, sextet), 2.46(3H,s), 3.39 (3H,s), 3.87-3.90(2H,m), 3.96(3H,s).

c) Methyl 6-(Bromomethyl)-1,2,3,4-tetrahydro-3-methyl-2,4-dioxo-1-propylthieno[2,3-d]pyrimidine-5-carboxylate Prepared using the procedure described in example 1, part b) from the product of part b) to give the subtitle compound.

δ $^1H_{CDCl_3}$ 1.02(3H,t), 1.82(2H,sextet), 3.39(3H,s), 3.91 (2H,t), 4.00(3H,s), 4.68(2H,s)

d) Methyl 6-[4,5-Dichloro-2-methyl-1H-imidazol-1-ylmethyl]-1,2,3,4-tetrahydro-3-methyl-2,4-dioxo-1-propyl-thieno[2,3-d]pyrimidine-5-carboxylate Prepared using the procedure described in example 1, part c) from the product of part c) to give the subtitle compound.

MS (APCI) 445/447 [M+H]+ δ $^1H_{CDCl_3}$ 0.99(3H,t), 1.76 (2H,sextet), 2.38(3H,s), 3.39(3H,s), 3.85(2H,td), 3.99(3H, s), 5.26(2H,s). Mpt. 155-156° C.

e) Sodium 6-[(4,5-Dichloro-2-methyl-1H-imidazol-1-yl)methyl]-1,2,3,4-tetrahydro-3-methyl-2,4-dioxo-1-propyl-thieno[2,3-d]pyrimidine-5-carboxylate Prepared using the procedure described in example 1, part d) from the product of part d) to give the sub-title compound.

MS (APCI) 431/433[M+H]+ δ $^1H_{DMSO}$ 0.87(3H,t), 1.67 (2H,sextet), 2.38(3H,s), 3.19(3H,s), 3.78(2H,t), 5.23(2H,s).

f) 6-[4,5-Dichloro-2-methyl-1H-imidazol-1-ylmethyl]-1,2,3,4-tetrahydro-N-methoxy-N,3-dimethyl-2,4-dioxo-1-propyl-thieno[2,3-d]pyrimidine-5-carboxamide Prepared using the procedure described in example 1, part e) from the product of part e) to give the title compound.

MS (APCI) 474/475/476[M+H]+ δ $^1H_{CDCl_3}$ 1.00(3H,t), 1.80(2H,sextet), 2.40(3H,s), 3.11+3.43(3H,2×s ratio 1:3), 3.38(3H,s), 3.49+3.99(3H,2×s ratio 3:1), 3.75-3.82(1H,m), 3.86-3.99(1H,m), 5.09-5.24(2H,m).

EXAMPLE 8

1,2,3,4-Tetrahydro-6-(1H-indazol-3-ylmethyl)-N-methoxy-N,3-dimethyl-1-(2-methylpropyl)-2,4-dioxo-thieno[2,3-d]pyrimidine-5-carboxamide a) 1,2,3,4-Tetrahydro-N-methoxy-N,3-di methyl-1-(2-methylpropyl)-2,4-dioxo-thieno[2,3-d]pyrimidine-5-carboxamide Trimethylaluminium (2M solution in toluene, 7.5 ml) was added dropwise to methoxylamin hydrochloride (1.5 g) in dry toluene (10 ml) and anhydrous THF (5 ml) at 0° C. under a nitrogen atmosphere. The solution was stirred for 1 h at 0° C. and then allowed to reach room temperature. The product of example 2 part a) (3 g, 9.7 mmol) was added portionwise and stirred for 1 h. The resulting solution was poured into ice/dilute HCl and then extracted with ethyl acetate (×3). The combined organic extracts were washed with brine and concentrated in vacuo, to afford the sub-title compound as a gum (3 g), which was used in the next step without further purification.

b) 3-[1,2,3,4-Tetrahydro-5-[(N-methoxy-N-methylamino)carbonyl]-3-methyl-1-(2-methylpropyl)-2,4-dioxothieno[2,3-d]pyrimidin-6-yl](hydroxy)methyl]-1H-indazole-1-carboxylic acid, phenylmethyl ester Prepared by the method of example 2 part a) using the product of part a) and 3-formyl-1H-indazole-1-carboxylic acid phenylmethyl ester.

LCMS (ESI) 606 (M++H)

c) 3-[1,2,3,4-Tetrahydro-5-[(N-methoxy-N-methylamino)carbonyl 1-3-methyl-1-(2-methylpropyl)-2,4-dioxothieno[2,3-d]pyrimidin-6-ylmethyl]-1H-indazole-1-carboxylic acid, phenylmethyl ester Trifluoroacetic acid (2 ml) was added to the crude product of part b) (1.7 g) in dichloromethane (5 ml) and triethylsilane (2 ml). The reaction mixture was stirred for 2 h and then poured into sodium bicarbonate solution and extracted with dichloromethane. The organic phase was washed with water and then dried over magnesium sulfate and concentrated in vacuo. The residue was purified by chromatography ($SiO_2$) eluting with ethyl acetate:iso-hexane (2:3), to give the sub-title compound as a colourless foam.
LCMS (EST) 460 ($M^+$+H)

d) 1,2,3,4-Tetrahydro-6-(1H-indazol-3-ylmethyl)-N-methoxy-N,3-dimethyl-1-(2-methyl propyl)-2,4-dioxo-thieno[2,3-d]pyrimidine-5-carboxamide The product of part c) (0.5 g) was dissolved in ethanol, treated with 10% palladium on charcoal (0.1 g) and stirred under an atmosphere of hydrogen (4 bar) for 1.5 h. The reaction mixture was filtered (celite) and concentrated in vacuo. The reaction mixture was purified by chromatography ($SiO_2$) eluting with ethyl acetate:hexane (3:1) to give the title compound as a clear gum (0.3 g).
LCMS (ESI) 456 (MS+H) δ $^1H_{CDCl3}$ 0.92(6H,d), 2.23 (1H,m), 3.08-3.43(3H,m), 3.46 and 3.99 (3H,m,rotamrers), 4.49 (2H,s), 7.17(1H,t), 7.4(1H,t), 7.46(1H,d), 7.81(1H,d).

EXAMPLE 9

1-(2,2-Dimethylpropyl)-1,2,3,4-tetrahydro-N-methoxy-N,3-dimethyl-2,4-dioxo-6-(quinolin-4-ylmethyl)-thieno[2,3-d]pyrimidine-5-carboxamide a) 6-Chloro-1-(2,2-dimethylpropyl)-3-methyl-pyrimidine-2.4(1H,3H)-dione

6-Chloro-3-methyl uracil (10.0 g) and potassium carbonate (10.34 g) in DMF (70 ml) under nitrogen were treated with neopentyl iodide (9.9 ml) and stirred for 48 h. Neopentyl iodide (7.4 ml) was added and the reaction was stirred under reflux for a further 37 h. The reaction was poured into water (700 ml) and extracted with ethyl acetate. The combined organics were dried and concentrated in vacuo to afford the subtitle compound an orange oil, 8.1 g.
δ $^1H_{CDCl3}$ 1.00 (9H, s), 3.34 (3H, s), 4.01 (2H, d), 8.02 (1H, s).

b) 1-(2,2-Dimethylpropyl)-6-mercapto-3-methyl-pyrimidine-2,4(1H,3H)-dione

The product of step a) (8.1 g) in ethanol (300 ml) was treated with NaSH (3.9 g) under nitrogen. After 48 h at room temperature the solvent was evaporated and the residue diluted with water. The aqueous phase was washed with ethyl acetate then acidified with 2M HCl. This was then extracted with ethyl acetate and the combined organics dried and concentrated in vacuo to afford the subtitle compound as an orange oil, 6.5 g.
δ $^1H_{CDCl3}$ 1.09 (9H, s), 3.27 (3H, s), 3.78 (0.5H, s), 4.18 (2H, s), 4.49 (1H, s), 5.79 (0.5H, s).

c) Ethyl 1-(2,2-dimethylpropyl)-3-methyl-2,4-dioxo-1,2,3,4-tetrahydrothieno[2,3-d]pyrimidine-5-carboxylate To the product of step b) (6.3 g) in dry dimethylformamide (100 ml) was added potassium carbonate (1.9 g) and stirred for 10 min. Ethyl bromopyruvate (4 ml) was added and was stirred under nitrogen at room temperature for 2 h. The reaction was poured into water (1 L) and acidified (2M HCl) and extracted with ethyl acetate. The combined organics were washed with brine (100 ml). Drying and evaporation afforded an oil. The oil was dissolved in dichloromethane (100 ml) and cooled in ice whilst stirring. Titanium tetrachloride (6 ml) was added and stirring continued under nitrogen for 2 hours. The reaction was poured into water (1 L) and extracted with dichloromethane (×2). The combined organics were dried and concentrated in vacuo. The residue was purified by chromatography ($SiO_2$/ethyl acetate-dichloromethane 0-8%) to afford the subtitle compound as an orange oil, 6.2 g
δ $^1H_{CDCl3}$ 1.05 (9H, s), 1.40 (3H, t), 3.42 (3H, s), 3.85 (2H, s), 4.42 (2H, q), 7.25 (1H, s). MS (APCI) 325.1 ($M^+$+H)

d) Ethyl 1-(2,2-dimethylpropyl)-6-[hydroxy(quinolin-4-yl)methyl]-3-methyl-2,4-dioxo-1,2,3,4-tetrahydrothieno[2,3-d]pyrimidine-5-carboxylate The subtitle compound was prepared by the method of example 2, part b) using the product of part c) and 4-quinolinecarboxaldehyde.
δ $^1H_{CDCl3}$ 0.91 (9H, s),1.40 (3H, t),3.38 (3H, s), 3.53 (1H, s),3.70 (1H, s), 4.47 (2H, q), 6.76 (1H, s), 7.51 (1H, m), 7.71 (1H, m), 7.81 (1H, m) 7.88 (1H, m), 8.16 (1H, m), 9.01 (1H, d).

e) Ethyl 1-(2,2-dimethylpropyl)-3-methyl-2,4-dioxo-6-(quinolin-4-ylmethyl)-1,2,3,4-tetrahydrothieno[2,3-d]pyrimidine-5-carboxylate The sub-title compound was prepared using the method of example 2, part c) using the product of part-d).
MS (ESI) 466 ($M^+$+H)

f) Sodium 1-(2,2-dimethylpropyl)-3-methyl-2,4-dioxo-6-(quinolin-4-ylmethyl)-1,2,3,4-tetrahydrothieno[2,3-d]pyrimidine-5-carboxylate The sub-title compound was prepared by the method of example 2, part d) using the product of part e)
MS (ESI) 438.0 ($M^+$+H)

g) 1-(2,2-Dimethylpropyl)-N-methoxy-N,3-dimethyl-2,4-dioxo-6-(quinolin-4-ylmethyl)-1,2,3,4-tetrahydrothieno[2,3-d]pyrimidine-5-carboxamide Prepared following the method of example 2 part e) to afford the title compound as a white solid (61 mg).
MS (APCI) 481.1 ($M^+$+H) δ $^1H_{DMSO}$ 0.91 (9H, d), 2.97 (1H, s), 3.21 (3H, d), 3.29 (2H, d), 3.42 (2H, s), 3.65 (2H, s), 3.71 (1H, s), 4.59 (2H, s), 7.43 (1H, m), 7.63 (1H, t) 7.77 (11H, m), 8.05 (1H, d), 8.29 (1H, m), 8.50 (1H, m), 8.87 (1H, d).

EXAMPLE 10 i 1,2,3,4-Tetrahydro-N-methoxy-N,3-dimethyl-6-[2-(1-methylethyl)-1H-imidazo-1-1-ylmethyl]-1-(2-methylpropyl)-2,4-dioxo-thieno[2,3-d]pyrimidine-5-carboxamide a) 1,2,3,4-Tetrahydro-3-methyl-6-[[2-(]-methylethyl)-1H-imidazol-1-yl]methyl]-1-(2-methylpronyl)-2,4-dioxo-thieno[2,3-d]pyrimidine-5-carboxylic acid, methyl ester The subtitle compound was prepared by the method of Example 1 step c).

MS (APCI) 419 [M+H]$^+$ δ $^1H_{CDCl_3}$ 0.94 (6H,d); 1.31 (6H,d); 2.22 (1H,septet); 3.0 (1H,quintet); 3.39 (3H,s); 3.70 (2H,d); 4.0 (3H,s); 5.25 (2H,s); 6.86 (1H,m); 7.02 (1H,m).

b) 1,2,3,4-Tetrahydro-3-methyl-6-[2-(1-methylethyl)-1H-imidazol-1-ylmethyl-1-(2-methylpropyl)-2,4-dioxo-thieno[2,3-d]pyrimidine-5-carboxylic acid, sodium salt The sub-title compound was prepared by the method of example 2 step d).

MS (APCI) 405 [M+H]$^+$ δ $^1H_{DMSO}$ 0.93 (6H,d); 1.33 (6H,d); 2.17 (1H, septet); 3.26 (3H,s); 3.53 (1H,septet); 3.74 (2H,d); 3.80 4.0 (1H,br.s); 6.0 (2H,s); 7.50-7.58 (1H,m); 7.64-7.69 (1H,m); 14.83 (1H, br.s).

c) 1,2,3,4-Tetrahydro-N-methoxy-N,3-dimethyl-6-[2-(1-methylethyl)-1H-imidazol-1-yl]methyl]-1-(2-methylpropyl)-2,4-dioxo-thieno[2,3-d]pyrimidine-5-carboxamide The title compound was prepared by the method of Example 1, step e).

MS (APCI) 448 [M+H]$^+$ δ $^1H_{CDCl_3}$ 0.96 (6H,d); 1.23-1.42 (6H,m); 2.23 (1H,septet); 2.98-3.08 (1H,m); 3.39 (3H,s); 3.43+3.98 (6H, 2×s ratio 5:1); 3.62 (1H,dd); 3.83 (1H,dd): 5.09-5.24 (2H,m); 6.87-6.89 (1H,m); 6.99-7.01 (1H,m).

EXAMPLE 10 ii 1,2,3,4-Tetrahydro-N-methoxy-N,3-dimethyl-1-(2-methylpropyl)-6-[2-(methylthio)-1H-imidazol-1-ylmethyl]-2,4-dioxo-thieno[2,3-d]pyrimidine-5-carboxamide a) 2-Methylthio-imidazole

Iodomethane (0.55 ml) was added to a solution of 2-mercaptoimidazole (0.89 g) in potassium hydroxide solution (8.90 ml, 1M) and stirred at room temperature for 3 h. The solution was partitioned between water and ethyl acetate. The organic layer was washed with brine, dried over magnesium sulfate, filtered and concentrated in vacuo to give the sub-title compound as a cream solid (0.87 g).

δ $^1H_{CDCl_3}$ 2.60 (3H,s); 5.30(1H,s); 7.07(2H,s).

b) 1,2,3,4-Tetrahydro-3-methyl-1-(2-methylpropyl)-6-[2-(methylthio)-1H-imidazol-1-ylmethyl]-2,4-dioxo-thieno[2,3-d]pyrimidine-5-carboxylic acid methyl ester The sub title compound was prepared by the method of Example 1, step c).

MS (APCI) 423 [M+H]$^+$ δ $^1H_{CDCl_3}$ 0.96 (6H,dd); 2.24 (1H, septet); 2.62 (3H,s); 3.39 (3H,s); 3.72 (2H,d); 4.01 (3H,s); 5.26 (2H,s); 7.06 (1H,m); 7.10 (1H,m).

c) 1,2,3,4-Tetrahydro-3-methyl-1-(2-methylpropyl)-6-[2-(methylthio)-1H-imidazol-1-ylmethyl]-2,4-dioxo-thieno[2,3-d]pyrimidine-5-carboxylic acid sodium salt The sub-title compound was prepared by the method of example 2, part d).

MS (APCI) 409/410 [M+H]$^+$ δ $^1H_{DMSO}$ 0.87 (6H,d); 2.16 (1H,septet); 3.19 (3H,s); 3.29 (3H,s); 3.66 (2H,d); 5.14 (2H,s); 6.88 (1H,s); 7.47 (1H,s).

d) 1,2,3,4-Tetrahydro-N-methoxy-N,3-dimethyl-1-(2-methylpropyl)-6-[2-(methyl thio)-1H-imidazol-1-ylmethyl]-2,4-dioxo-thieno[2,3-d]pyrimidine-5-carboxamide The title compound was prepared by the method of Example 1, step e).

MS (APCI) 452 [M+H]$^+$ δ $^1H_{CDCl_3}$ 0.96-0.98 (6H,m); 2.27 (1H,septet); 2.63 (3H,s); 3.38 (3H,s); 3.44+3.99 (3H, 2×s, ratio 5:1); 3.44+3.08 (3H, 2×s ratio 5:1); 3.63 (1H,m); 3.84 (1H,m); 5.12 (1H,d); 5.28 (1H,d); 7.08 (1H,s); 7.10 (1H,s).

EXAMPLE 10 iii

6-[2-Chloro-1H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide a) 6-[2-Chloro-1H-imidazol-1-ylmethyl 1-1,2,3,4-tetrahydro-3-methyl-1-(2-methylpropyl)-2,4-dioxo-thieno[2,3-d]pyrimidine-5-carboxylic acid, methyl ester The sub-title compound was prepared by the method of Example 1 step c) using 2-chloro-imidazole.

MS (APCI) 411 [M+H]$^+$ δ $^1H_{CDCl_3}$ 0.96 (6H,d); 2.25 (1H, septet); 3.39 (3H,s); 3.73 (2H,d); 4.01 (3H,s); 5.25 (2H,s); 6.98 (1H,s); 7.06 (1H,s).

b) 6-[2-Chloro-1H-imidazol-1-ylmethyl]-1,2,3,4-tetrahydro-3-methyl-1-(2-methylpronyl)-2,4-dioxo-thieno[2,3-d]pyrimidine-5-carboxylic acid, sodium salt The sub-title compound was prepared by the method of Example 1, step d).

MS (APCI) 397 [M+H]$^+$ δ $^1H_{DMSO}$ 0.88 (6H,d); 2.17 (1H, septet); 3.20(3H,s); 3.67 (2H,d); 5.18 (2H,s); 6.83 (1H,d); 7.53 (1H,d).

c) 6-[2-Chloro-1H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide The subtitle compound was prepared by the method of Example 1, step e).

MS (APCI) 440 [M+H]$^+$ δ $^1H_{CDCl_3}$ 0.97 (6H,dd); 2.27 (1H,septet); 3.39 (3H,s); 3.44+3.08+3.99 (3×s,ratio1:4:1, 6H); 3.65 (1H,dd); 3.85 (1H,dd); 5.09 (1H,d); 5.29 (1H,d); 6.96 (1H,s); 7.10 (1H,s).

EXAMPLE 10 iv 1,2,3,4-Tetrahydro-N-methoxy-N,3-dimethyl-1-(2-methylpropyl)-6-[2-(methylthio)-1H-benzimidazol-1-ylmethyl]-2,4-dioxo-thieno[2,3-d]pyrimidine-5-carboxamide a) Methyl 1,2,3,4-tetrahydro-3-methyl-1-(2-methylpropyl)-6-[2-(methylthio)-1H-benzimidazol-1-ylmethyl]-2,4-dioxo-methyl ester thieno[2,3-d]pyrimidine-5-carboxylate Prepared using the procedure described in example 1, part c) from the product of example 1 step b) and 2-methylthiobenzimidazole, to give the subtitle compound.

MS(APCI) 474 [M+H]$^+$ b) 1,2,3,4-Tetrahydro-3-methyl-1-(2-methylpropyl)-6-[2-(methylthio)-1H-benzimidazol-1-ylmethyl]-2,4-dioxo-thieno[2,3-d]pyrimidine-5-carboxylic acid Prepared using the procedure described in example 1, part d) from the product of step a), to give the subtitle compound as a white solid.
MS(APCI) 459 [M+H]+ c) 1,2,3,4-Tetrahydro-N-methoxy-N,3-dimethyl-1-(2-methylpropyl)-6-[2-(methylthio)-1H-benzimidazol-1-ylmethyl]-2,4-dioxo-thieno[2,3-d]pyrimidine-5-carboxamide Prepared using the procedure described in example 1, part e), from the product of step b) to give the title compound.
MS(APCI) 502 [M+H]+ δ $^1H_{DMSO}$ 0.87(3H,s), 0.84(3H,s), 2.07-2.2(1H,m), 2.76(3H,s), 2.99(3H,s), 3.17(3H,s), 3.21 (3H,s), 3.62-3.7(2H,m), 5.43(2H,d), 7.13-7.2(2H,m), 7.5-7.6(2H,m).

EXAMPLE 10 v 1,2,3,4-Tetrahydro-N-(2-hydroxyethyl)-N-methoxy-3-methyl-1-(2-methylpropyl)-6-2-(methylthio)-1H-imidazol-1-ylmethyl]-2,4-dioxo-thieno[2,3-d]pyrimidine-5-carboxamide a) 1,2,3,4-Tetrahydro-N-methoxy-3-methyl-1-(2-methylpropyl)-6-[[2-(methylthio)-1H-imidazol-1-yl]methyl]-2,4-dioxo-thieno[2,3-d]pyrimidine-5-carboxamide The sub-title compound was prepared by the method of example 1, part e) using the product of example 10 ii), part b) and methoxylamine hydrochloride.
MS (APCI) 499 [M+H]+ δ $^1H_{CDCl3}$ 0.92(3H,s), 0.95(3H,s), 2.04-2.26(1H,m), 2.61(3H,s), 3.46 (3H,s), 3.74(2H,d), 3.9(3H,s), 5.8(2H,s), 7.12(2H,t) and 7.17(2H,t).

b) 1,2,3,4-Tetrahydro-N-methoxy-3-methyl-1-(2-methylpropyl)-6-[2-(methylthio)-1H-imidazol-1-ylmethyl]-2,4-dioxo-N-[2-[(tetrahydro-2H-pyran-2-yl)oxy]ethyl]-thieno[2,3-d]pyrimidine-5-carboxamide The product of part a) (180 mg), 2-(2-bromoethoxy) tetrahydro-2H-pyran (0.28 g), potassium carbonate (0.17 g), acetone (3 ml) and DMF (0.5 ml) were heated at 60° C. for 24 h. The reaction was quenched with water and then extracted with ethyl acetate (×2). The combined organic extracts were washed (brine), dried (MgSO$_4$) and concentrated in vacuo to afford the sub-title compound as an oil (130 mg).
MS (APCI) 566/494 [M+H]+ c) 1,2,3,4-Tetrahydro-N-(2-hydroxyethyl)-N-methoxy-3-methyl-1-(2-methylpropyl)-6-[2-(methylthio)-1H-imidazol-1-ylmethyl]-2,4-dioxo-thieno[2,3-d]pyrimidine-5-carboxamide The product of part b) was treated with p-toluenesulfonic acid and methanol for 24 h. Water was added to the reaction mixture and then extracted with dichloromethane (×3). The combined organic extracts were dried (MgSO$_4$) and concentrated in vacuo to give a viscous oil. The oil was triturated with diethyl ether to afford the title compound (15 mg).

MS (APCI) 482 [M+H]+ δ $^1H_{DMSO}$ 0.85(3H,s), 0.91(3H,s), 2.06-2.2 (1H,m), 3.2 (3H,s), 3.27-3.32(7H,m), 3.61-3.84 (4H,m), 3.84-3.95(1H,m),4.82-4.9(1H,m(br)), 5;2-5.3(2H,m), 6.97(1H, d) and 7.24(1H,d).

EXAMPLE 10 vi 1,2,3,4-Tetrahydro-6-[2-(methylamino)-1H-benzimidazol-1-ylmethyl]-N-methoxy-N,3-dimethyl-1-(2-methylpropyl)-2,4-dioxo-thieno [2,3-d]pyrimidine-5-carboxamide a) 1,2,3,4-Tetrahydro-3-methyl-6-[2-(methylamino)-1H-benzimidazol-1-ylmethyl]-1-(2-methylpropyl)-2,2-dioxo-thieno[2,3-d]pyrimidine-5-carboxylic acid, methyl ester Prepared by the method of example 1 part c) and 2-(methylamino)benzimidazole to give the title compound as a white solid (0.85 g).
MS (APCI) 456 [M+H]+ δ $^1H_{DMSO}$ 0.83-0.85(6H,d), 2.05(1H, m), 2.94-2.95(3H,d), 3.19(3H,s), 3.60-3.63(2H,d), 3.84(3H,s), 5.39(2H,s), 6.83-6.87(2H,m), 6.90-6.99 (1H, t), 7.08-7.1 1(1H, d), 7.20-7.22(1H, d).

b) 1,2,3,4-Tetrahydro-3-methyl-6-[2-(methylamino)-1H-benzimidazol-1-ylmethyl]-1-(2-methylpropyl)-2,4-dioxo-thieno[2,3-d]pyrimidine-5-carboxylic acid Prepared by the method of example 1 part d) to give the sub-title compound as a beige solid (0.54 g).
MS (APCI) 442 [M+H]+ c) 1,2,3,4-Tetrahydro-6-[2-(methylamino)-1H-benzimidazol-1-ylmethyl]-N-methoxy-N,3-dimethyl-1-(2-methylpropyl)-2,4-dioxo-thieno[2,3-d]pyrimidine-5-carboxamide N,O-Dimethylhydroxylamine hydrochloride (0.09 g) and triethylamine (0.12 ml) were added to a solution of the product of step c) (0.2 g) in dichloromethane (5 ml). 1-Hydroxybenzotriazole (0.12 g) was added as well as 1-ethyl-3-(3'-dimethylaminopropyl)-carbodiimide hydrochloride (0.17 g). The reaction mixture was stirred for 12 h at room temperature. The solution was concentrated in vacuo. The residue was purified by flash silica chromatography eluting with a gradient of 0-3% methanol in dichloromethane. The product obtained was recrystallised from dichloromethane/isohexane to give the title compound as a white solid (0.024 g).
MS(ES+) 485.1967 [M+H]+ δ $^1H_{DMSO}$ 0.82-0.86(6H,m), 2-2.1 (1H, m), 2.93(3H, d), 3 (1H,s), 3.2(3H, s), 3.34(2H, s), 3.43(2H,s), 3.61-3.64(2H,d), 3.82(1H,s), 5.12-5.53 (2H, ABq), 6.83-6.99(3H, m), 7.19-7.28(2H, m)

EXAMPLE 10 vii 1,2,3,4-Tetrahydro-N-methoxy-N,3-dimethyl-1-(2-methylpropyl)-2,4-dioxo-6-[2-propyl-1H-benzimidazol-1-ylmethyl]-thieno[2,3-1 pyrimidine-S-carboxamide a) 1,2,3,4-Tetrahydro-3-methyl-1-(2-methylpropyl)-2,4-dioxo-6-[2-propyl-1H-benzimidazol-1-ylmethyl]-thieno[2,3-d]pyrimidine-5-carboxylic acid, methyl ester Prepared using the procedure described in example 1 part c) from the product of example 1 part b) and 2-n-propylbenzimidazole to give the subtitle compound after purification by flash silica chromatography eluting with isohexane: ethyl acetate (1:1).

MS (APCI) 469 [M+H] δ $^1H_{DMSO}$ 0.81-0.83(6H,d), 0.94-0.99 (3H, t), 1.72-1.82(2H, sext), 2.01-2.08(1H, m), 2.80-2.85(2H,t), 3.19(3H, s), 3.59-3.61 (2H, d), 3.78(3H, s), 5.65(2H, s),7.15-7.23(2H, m), 7.53-7.59 (2H, m)

b) 1,2,3,4-Tetrahydro-3-methyl-1-(2-methylpropyl)-2,4-dioxo-6-[2-propyl-1H-benzimidazol-1-ylmethyl]-thieno[2,3-d]pyrimidine-5-carboxylic acid Prepared using the procedure described in example 1 part d) from the product of part a) to give the subtitle compound.

MS (APCI) 455 [M+H] δ $^1H_{DMSO}$ 0.78-0.85(6H,d), 0.94-1 (3H, t), 1.74-1.86(2H, sext), 2-2.07(1H, m), 2.87-2.92(2H,t), 3.25(3H, s), 3.58-3.6(2H, d), 5.82(2H, s), 7.21-7.27(2H, m), 7.58-7.65 (2H, m)

c) 1,2,3,4-Tetrahydro-N-methoxy-N,3-dimethyl-1-(2-methylpropyl)-2,4-dioxo-6-[2-propyl-1H-benzimidazol-1-ylmethyl]-thieno[2,3-d]pyrimidine-5-carboxamide 1-Hydroxybenzotriazole (0.14 g) was added to a solution of the product of step b) (0.25 g) in dichloromethane (5 ml). After stirring for 5 minutes, 1-ethyl-3-(3'-dimethylaminopropyl)-carbodiimide hydrochloride (0.21 g) was added. After stirring for 10 minutes, N,O-dimethylhydroxylamine hydrochloride (0.1 g) and triethylamine (0.15 ml) were added The reaction mixture was stirred for 12 h at room temperature. The solution was concentrated in vacuo. The residue was purified by flash silica chromatography eluting with a gradient of 0-3% methanol in dichloromethane to give the title compound as a yellow solid (0.118 g).

MS (APCI) 498.2 [M+H] δ $^1H_{DMSO}$ 0.80-0.84(6H,m), 0.95-1 (3H, t), 1.76-1.85(2H, sext), 2-2.1(1H, m), 2.84-2.93 (2H,t), 2.96 (1H,s), 3.2 (3H, s), 3.27(2H, s), 3.41(2H, s), 3.62-3.64(2H, d), 3.76 (1H, s), 5.41-5.68(2H, m), 7.14-7.21 (2H, m), 7.55-7.66 (2H, m)

EXAMPLE 10 viii 1,2,3,4-Tetrahydro-N-methoxy-N,3-dimethyl-1-(2-methylpropyl)-2,4-dioxo-6-[2,3-dihydro-3-methyl-2-oxo-1H-benzimidazol-1-ylmethyl]-thieno[2,3-d]pyrimidine-5-carboxamide a) Methyl 6-[2,3-dihydro-3-methyl-2-oxo-1H-benzimidazol-1-ylmethyl]-1,2,3,4-tetrahydro-3-methyl-1-(2-methylpropyl)-2,4-dioxo-thieno[2,3-d]pyrimidine-5-carboxylate The subtitle compound was prepared by the method of example 1 step c) using the product of example 1 step b) and N-methylbenzimidazolone.

MS (APCI) 457 [M+H]$^+$ δ $^1H_{DMSO}$ 0.88(6H,d), 2.13(1H, non), 3.19(3H,s), 3.27(3H,s), 3.36(3H,s), 3.67(2H,d), 3.85 (2H,s), 6.95-7.20(4H,m).

b) 6-[2,3-Dihydro-3-methyl-2-oxo-1H-benzimidazol-1-ylmethyl]-1,2,3,4-tetrahydro-3-methyl-1-(2-methylpropyl)-2,4-dioxo-thieno[2,3-d]pyrimidine-5-carboxylic acid The subtitle compound was prepared by the method of example 1 step d). using the product of step a).

MS (APCI) 443 [M+H]$^+$ δ $^1H_{DMSO}$ 0.85(6H,d), 2.10(1H, non), 3.25(3H,s), 3.35(3H,s), 3.67(2H,d), 5.34(2H,s), 6.95-7.21(4H,m), 10.80(1H, s).

c) 6-[2,3-Dihydro-3-methyl-2-oxo-1H-benzimidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide The title compound was prepared by the method of example 1 step e). using the product of step b).

MS(ES$^+$) 486[M+H]$^+$ δ $^1H_{DMSO}$ (90° C.) 0.88(6H,d), 2.16(]H, non), 3.00(3H,s), 3.22(3H,s), 3.35(3H,s), 3.41(3H, s), 3.67(2H,d), 4.97(1H,d), 5.18(1H,d), 7.01-7.23(4H,m).

EXAMPLE 10 ix

6-[2,3-Dihydro-2-oxo-benzothiazol-3-ylmethyl]-1,2,3,4-tetrahydro-N-methoxy-N,3-dimethyl-1-(2-methylpropyl)-2,4-dioxo-thieno[2,3-d]pyrimidine-5-carboxamide a) Methyl 1,2,3,4-tetrahydro-3-methyl-1-(2-methylpropyl)-2,4-dioxo-6-[2,3-dihydro-2-oxo-benzothiazol-3-ylmethyl]-thieno[2,3-d]pyrimidine-5-carboxylate The subtitle compound was prepared by the method of example 1 step c) using the product of example 1 step b) and benzothiazolone.

MS (APCI) 460 [M+H]$^+$ δ $^1H_{DMSO}$ 0.88(6H,d), 2.13(1H, non), 3.19(3H,s), 3.67(2H,d), 3.84(3H,s), 5.32(2H,s), 7.23-7.70(4H,m).

b) 6-[2,3-Dihydro-2-oxo-benzothiazol-3-ylmethyl]-1,2,3,4-tetrahydro-3-methyl-1-(2-methylpropyl)-2,4-dioxo-thieno[2,3-d]pyrimidine-5-carboxylic acid The subtitle compound was prepared by the method of example 1 step d).

Using the Product of Step a).

MS (APCI) 468 [M+H]$^+$ δ $^1H_{DMSO}$ 0.86(6H,d), 2.13(1H, non), 3.19(3H,s), 3.64(2H,d), 5.20(2H,s), 7.18(1H,dt), 7.28 (1H,dt), 7.63(1H,dt), 8.18(1H,d).

c) 6-[2,3-Dihydro-2-oxo-benzothiazol-3-ylmethyl]-1,2,3,4-tetrahydro-N-methoxy-N,3-dimethyl-1-(2-methylpropyl)-2,4-dioxo-thieno[2,3-d]pyrimidine-5-carboxamide The title compound was prepared by the method of example 1 step e).

Using the Product of Step b).

MS(ES$^+$) 489[M+H]$^+$ δ $^1H_{DMSO}$ (90° C.) 0.89(6H,d), 2.16(1H, non), 3.00(3H,s), 3.09(1H,d), 3.32(1H,d), 3.21(3H, s), 3.41(3H,s), 3.67-3.70(2H,m), 4.97(1H,d), 5.18(1H,d), 7.20(1H,t), 7.33-7.43(2H,m), 7.63(1H,d).

EXAMPLE 11 i

6-[(1-Acetyl-1H-indol-3-yl)methyl]-1,2,3,4-tetrahydro-N-methoxy-N,3-dimethyl-(2-methylpropyl)-2,4-dioxothieno[2,3-d]pyrimidine-5-carboxamide a) 6-[(1-Acetyl-1H-indol-3-yl)methyl]-1,2,3,4-tetrahydro-3-methyl-1-(2-methylpropyl)-2,4-dioxothieno[2,3-d]pyrimidine-5-carboxylic acid Acetic anhydride (134 μl) was added to a solution of example 5 part b), (0.45 g), 4-dimethylaminopyridine (catalytic amount), and triethylamine (183 μl), in dichloromethane (2 ml) at ambient temperature with stirring under nitrogen. After stirring for 48 h the mixture was concentrated in vacuo. The residue was purified by column chromatography, eluting with ethyl acetate/acetic acid (1%) to give the sub-title compound as a solid (0.18 g).

MS (ES$^+$) 454[M+H]$^+$ b) 6-[(1-Acetyl-1H-indol-3-yl)methyl]-1,2,3,4-tetrahydro-N-methoxy-N,3-dimethyl-1-(2-methylpropyl)-2,4-dioxothieno[2,3-d]pyrimidine-5-carboxamide Prepared by the method of example 1 part e) using the product of step a). The crude material was purified by reverse phase preparative HPLC (50-95% acetonitrile) to give the title compound (23 mg).

MS (APCI) 497[M+H]$^+$ δ $^1$H$_{DMSO}$ 0.90-0.92 (6H,m), 2.15-2.19 (1H,m), 2.70 (3H,s), 3.05 (1H,s), 3.27 (3H,s), 3.52 (2H,s), 3.62-3.69 (3H,m), 3.83 (1H,s), 4.17-4.19 (3H,m), 7.28-7.42 (2H,m), 7.68-7.75 (1H,m), 7.87-7.89 (1H,m), 8.36 (1H,d)

EXAMPLE 11 ii 1,2,3,4-Tetrahydro-N-methoxy-N,3-dimethyl-1-(2-methylpropyl)-6-[2-methyl-1H-pyrrolo[2,3-b]pyridin-3-ylmethyl]-2,4-dioxo-thieno[2,3-d]pyrimidine-5-carboxamide a) 1,2,3,4-Tetrahydro-3-methyl-1-(2-methylpropyl)-6-[2-methyl-1H-pyrrolo[2,3-b]pyridin-3-ylmethyl]-2,4-dioxothieno[2,3-d]pyrimidine-5-carboxylic acid methyl ester The sub-title compound (0.7 g) was prepared from the product of example 1 part b) and 2-methyl-7-azaindole (0.68 g) by the method of example 3, part a).

MS (ES$^+$) 441 [M+H]$^+$ b) 1,2,3,4-Tetrahydro-3-methyl-1-(2-methylpropyl)-6-[2-methyl-1H-pyrrolo[2,3b]pyridin-3-ylmethyl]-2,4-dioxothieno[2,3d]pyrimidine-5-carboxylic acid The sub-title compound (0.66 g) was prepared from the product of part a) (0.7 g) by the method of example 1, part b).

MS (ES$^+$) 427[M+H]$^+$ c) 1,2,3,4-Tetrahydro-N-methoxy-N,3-dimethyl-1-(2-methylpropyl)-6-[2-methyl-1H-pyrrolo[2,3-b]pyridin-3-ylmethyl]-2,4-dioxo-thieno[2,3-d]pyrimidine-5-carboxamide The title compound was prepared from the product of example step b), by the method of example 1, part d).

MS (APCI) 470[M+H]$^+$ δ $^1$H$_{DMSO}$ 0.81-0.83 (6H,m), 2.07 (1H,heptet), 2.39 (3H,s), 2.98 (1H,s),3.2-3.21 (3H,m), 3.43 (2H,s), 3.54-3.66 (3H,m), 3.78 (1H,m), 4.06-4.16 (2H, m), 6.95-6.98 (1H,m), 7.77-7.83 (1H,m), 8.08 (1H,d), 11.45 (1H,s)

EXAMPLE 12

1,2,3,4-Tetrahydro-N-methoxy-N,3-dimethyl-6-[2-methyl-1H-indol-3-ylmethyl]-1-(2-methylpropyl)-2,4-dioxothieno[2,3-d]pyrimidine-5-carboxamide

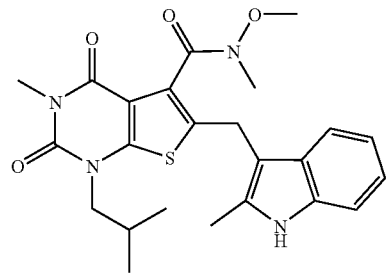

a) Methyl 1,2,3,4-tetrahydro-3-methyl-6-[2-methyl-1H-indol-3-ylmethyl]-1-(2-methylpropyl)-2,4-dioxothieno[2,3-d]pyrimidine-5-carboxylate A solution of methyl 1,2,3,4-tetrahydro-3,6-dimethyl-1-(2-methylpropyl)-2,4-dioxo-thieno[2,3-d]pyrimidine-5-carboxylate [example 1 step a), 7.00 g) and N-bromosuccinimide (4.42 g) in chloroform (140 ml) was refluxed under illumination from a tungsten lamp for 2 hours. The solution was cooled to room temperature, saturated aqueous sodium bicarbonate solution (140 ml) and 2-methylindole (5.92 g) were added and the mixture stirred rapidly for 48 hours. The phases were separated and the aqueous phase extracted with dichloromethane (100 ml). Combined organic extracts were dried over anhydrous magnesium sulfate, filtered and evaporated under reduced pressure. The residue was purified by column chromatography over silica, eluting with ethyl acetate/i-hexane (1:3) to give the sub-title compound as a pale brown solid (6.68 g).

MS (ES$^+$) 440 [M+H]$^+$ NMR δ $^1$H$_{CDCl3}$ 0.87 (6H, d), 2.11-2.21 (1H, m), 2.42 (3H, s), 3.38 (3H, s), 3.61 (2H, d), 3.99 (3H, s), 4.22 (2H, s), 7.08 (1H, t), 7.15 (1H, t), 7.31 (1H, d), 7.46 (1H, d), 7.91 (1H, s, br).

b) 1,2,3,4-Tetrahydro-3-methyl-6-[2-methyl-1H-indol-3-ylmethyl]-1-(2-methylpropyl)-2,4-dioxothieno[2,3-d]pyrimidine-5-carboxylic acid Sodium hydroxide solution (1M, 13.6 ml) and methanol (25 ml) were added to a stirred solution of the product from step a) (4.00 g) in tetrahydrofuran (100 ml). After 28 hours, the solution was concentrated under reduced pressure to 20 ml volume, diluted with water (200 ml) and extracted with ether (2×100 ml). The aqueous phase was acidified to pH 2 by addition of concentrated hydrochloric acid and extracted with ethyl acetate/methanol (19:1, 2×200 ml). Organic extracts were dried over anhydrous magnesium sulfate, filtered and evaporated under reduced pressure to give the sub-title compound as a white solid (4.00 g).

MS (ES$^+$) 426 [M+H]$^+$ NMR δ $^1$H$_{DMSO}$ 0.80 (6H, d), 1.99-2.09 (1H, m), 2.37 (3H, s), 3.18 (3H, s), 3.59 (2H, d), 4.32 (2H, s), 6.91 (1H, t), 7.00 (1H, t), 7.26 (1H, d), 10.96 (1H, s), 14.05 (1H, s, br).

c) 1,2,3,4-Tetrahydro-N-methoxy-N,3-dimethyl-6-[2-methyl-1H-indol-3-ylmethyl]-1-(2-methylpropyl)-2,4-dioxothieno[2,3-d]pyrimidine-5-carboxamide The title compound was prepared from the product of part b) by the method of example 1, part e).
MS (APCI) 469[M+H]$^+$ $^1$H NMR(DMSO) δ 0.81-0.83 (6H,m), 2.04-2.08 (1H,m), 2.37 (3H,s), 2.99 (1H,s), 3.20 (3H,s), 3.25-3.40 (2H,m), 3.53-3.66 (2H,m), 3.79 (1H,m), 4.03-4.13 (2H,m), 6.91 (1H,t), 7.00 (1H,t),7.24 (1H,d),7.37-7.44 (1H,m)

EXAMPLE 13

6-[3-Chloroquinolin-4-ylmethyl]-1,2,3,4-tetrahydro-N-methoxy-N,3-dimethyl-1-(2-methylpropyl)-2,4-dioxo-thieno[2,3-d]pyrimidine-5-carboxamide a) 3-Chloro-4-quinolinecarboxaldehyde A solution of selenium dioxide (1.90 g) in 1,4-dioxan (5 ml) and water (1.2 ml) was added dropwise over 15 min to a stirred solution of 3-chloro-4-methylquinoline (2.91 g) in 1,4-dioxan (10 ml) at 60-70° C. The mixture was heated at reflux for 6 h, allowed to warm to room temperature, then concentrated in vacuo. The residue was purified by column chromatography (SiO$_2$), eluting with dichloromethane to 5% methanol in dichloromethane by a stepwise gradient, to give the sub-title compound as a yellow solid (1.19 g).
MS (ES$^+$) 192/194[M+H]$^+$ δ $^1$H$_{CDCl3}$ 7.73 (1H,ddd), 7.79 (1H,ddd), 8.15 (1H,dd), 8.89 (H,dd), 8.98 (1H,s), 10.88 (1H,s).

b) Ethyl 6-[3-chloro-4-quinolinylhydroxymethyl]-12,3,4-tetrahydro-3-methyl-1-(2-methylpropyl)-2,4-dioxo-thieno[2,3-d]pyrimidine-5-carboxylate The subtitle compound was prepared by the method of example 2, part b) using the product of part a) and example 2, part a)
MS (ES$^+$) 502/504{M+H]$^+$ δ $^1$H$_{CDCl3}$ 0.91 (3H,d), 1.22 (3H,t), 2.19 (1H,sex), 3.36 (3H,s), 3.60-3.73 (2H,m), 3.89 (1H,d), 4.03-4.27 (2H,m), 7.04 (1H,s), 7.37 (1H,t), 7.57 (1H,t), 8.14 (1H,d), 8.52 (1H,d), 8.56 (1H,d).

c) Ethyl 1,2,3,4-tetrahydro-3-methyl-1-(2-methylpropyl)-2,4-dioxo-6-(4-quinolinylmethyl)-thieno[2,3-d]pyrimidine-5-carboxylate Methanesulfonyl chloride (0.07 ml) was added to a solution of the product of part b) (0.42 g) and triethylamine (0.23 ml) in anhydrous THF (10 ml) at room temperature under nitrogen and the mixture stirred for 30 min. 10% palladium on charcoal (30 mg) was added and the mixture hydrogenated at 5 bar for 2 h. It was filtered through celite washing with methanol (100 ml). The organic material was concentrated in vacuo and the residue purified by column chromatography (SiO$_2$), eluting with 1:1 ethyl acetate/i-hexane, to give the sub-title compound as a solid (0.31 g).
MS (ES$^+$) 486/488 {M+H]$^+$ δ $^1$H$_{CDCl3}$ 0.86 (6H,d), 1.47 (3H,t), 2.12 (1H,non), 3.38 (3H,s), 3.59 (2H,d), 4.53 (2H,q), 4.80 (2H,s), 7.63 (1H,ddd), 7.74 (1H,ddd), 8.12-8.17 (2H, m), 8.91 (1H,s)

d) Sodium 6-[3-chloro-4-quinolinylmethyl]-1,2,3,4-tetrahydro-3-methyl-1-(2-methylpropyl)-2,4-dioxo-thieno[2,3-d]pyrimidine-5-carboxylate The subtitle compound was prepared by the method of example 2, step d) using the product of step c).

MS (ES$^+$) 458/460{M+H]$^+$ δ $^1$H$_{DMSO}$ 0.77 (6H,d), 2.03 (1H,non), 3.18 (3H,s), 3.52 (2H,d), 4.70 (2H,s), 7.61 (1H, ddd), 7.76 (1H,ddd), 8.02 (1H,d), 8.85 (1H,d), 8.95 (1H,s)

e) 6-[3-Chloro-4-quinolinylmethyl]-1,2,3,4-tetrahydro-N-methoxy-N,3-dimethyl-1-(2-methylpronyl)-2,4-dioxo-thieno[2,3-d]pyrimidine-5-carboxamide The subtitle compound was prepared by the method of example 1 step e) using the product of step d).
MS (APCI) 501/503{M+H]$^+$ δ $^1$H$_{DMSO}$ (130° C.) 0.82 (6H,m), 2.09(1H,non), 3.17 (3H,s), 3.22 (3H,s), 3.57 (3H,s), 3.59 (2H,d), 4.70 (2H,s), 7.66 (1H,t), 7.77 (1H,t), 8.07 (1H,d), 8.23 (1H,d), 8.89 (1H,s)

EXAMPLE 14 i

N-Methoxy-N,3-dimethyl-2,4-dioxo-i-Propyl-6-(quinolin-4-ylmethyl)-1,2,3,4-tetrahydrothieno[2,3-d]pyrimidine-5-carboxamide a) 6-Chloro-3-methyl-1-propylpyrimidine-2,4(1H,3H)-dione The sub-title compound was prepared by the method of 9, part a) using 6-chloro-3-methyl uracil and propyl iodide.
δ $^1$H$_{CDCl3}$ 0.98 (3H, t), 1.74 (2H, sextet), 3.33 (3H, s), 4.02 (2H, t), 8.02 (1H, s).

b) 6-Mercapto-3-methyl-1-propyl-pyrimidine-2,4 (1H,3H)-dione

The sub-title compound was prepared by the method of example 9, part b) using the product of step a).
δ $^1$H$_{CDCl3}$ 0.97 (3H, t), 1.72 (2H, m), 3.31 (3H, s), 4.29 (2H, s).

c) Ethyl 3-methyl-2,4-dioxo-1-propyl-1,2,3,4-tetrahydrothieno[2,3-d]pyrimidine-5-carboxylate The sub-title compound was prepared by the method of example 9, part c) using the product of step b).
δ $^1$H$_{CDCl3}$ 1.02 (3H, t), 1.83 (2H, sextet), 3.42 (3H, s), 3.95 (2H, t), 4.41 (2H, q), 7.30 (1H, s). MS (APCI+ve) 297.1 (M$^+$+H)

d) Ethyl 6-[hydroxy(quinolin-4-yl)methyl]-3-methyl-2,4-dioxo-1-propel-1,2,3,4-tetrahydrothieno[2,3-d]pyrimidine-5-carboxylate The sub-title compound was prepared by the method of example 9, part d) using the product of step c).
δ $^1$H$_{CDCl3}$ 0.89 (3H, t), 1.41 (3H, t), 1.65 (2H, sextet), 3.38 (3H, s), 3.75 (1H, d), 3.64 (1H, m), 3.80 (1H, m), 4.48 (2H, q), 6.78 (1H, d), 7.52 (1H, m), 7.72 (1H, m) 7.84 (1H, m), 7.90 (1H, d), 8.16 (1H, m), 9.02 (1H, d).

e) Ethyl 3-methyl-2,4-dioxo-1-propyl-6-(quinolin-4-ylmethyl)-1,2,3,4-tetrahydrothieno[2,3-d]pyrimidine-5-carboxylate The sub-title compound was prepared by the method of example 9, part e) using the product of step d).
MS (ESI) 437.9 (M$^+$+H)

f) Sodium 3-methyl-2,4-dioxo-1-propyl-6-(quinolin-4-ylmethyl)-1,2,3,4-tetrahydrothieno[2,3-d]pyrimidine-5-carboxylate The sub-title compound was prepared by the method of example 9, part f) using the product of step e).
δ $^1H_{DMSO}$ 0.80 (3H, t), 1.57 (2H, sextet), 3.68 (2H, t), 4.55 (2H, s), 3.19 (3H, s), 7.53 (2H, d), 7.57 (1H, m) 7.74 (1H, m), 8.01 (1H, d), 8.61 (1H, d), 8.83 (1H, d).

g) N-Methoxy-N,3-dimethyl-2,4-dioxo-1-propyl-6-(quinolin-4-ylmethyl)-1,2,3,4-tetrahydrothieno[2,3-d]pyrimidine-5-carboxamide The sub-title compound was prepared by the method of example 9, part g) using the product of step f).
δ $^1H_{DMSO}$ 0.83 (3H, m), 1.61 (2H, q), 2.98 (1H, s), 3.21 (3H, d), 3.30 (2H, m), 3.43 (2H, s), 3.74 (3H, d), 4.60 (2H, s), 7.46 (1H, m), 7.63 (1H, m), 7.78 (1H, m) 8.05 (1H, d), 8.27 (1H, m), 8.88 (1H, d). MS (APCI) 453.1 (M$^+$+H)

EXAMPLE 14 ii

1-Ethyl-N-methoxy-N,3-dimethyl-2,4-dioxo-6-(quinolin-4-ylmethyl)-1,2,3,4-tetrahydrothieno[2,3-d]pyrimidine-5-carboxamide a) 6-Chloro-1-ethyl-3-methylpyrimidine-2,4(1H,3H)-dione The sub-title compound was prepared by the method of example 9, part a) using 6-chloro-3-methyl uracil and ethyl iodide.
δ $^1H_{CDCl3}$ 1.32 (3H, d), 3.33 (3H, s), 4.15 (2H, q), 5.92 (1H, s).

b) 1-Ethyl-6-mercapto-3-methyl-pyrimidine-2,4(1H,3H)-dione

The sub-title compound was prepared by the method of example 9, part b) using the product of step c).
δ $^1H_{CDCl3}$ 1.26 (3H, t), 3.31 (3H, s), 4.15 (0.5H, s), 4.49 (2H, q), 5.57 (0.5H, s).

c) Ethyl 1-ethyl-3-methyl-2,4-dioxo-1,2,3,4-tetrahydrothieno[2,3-d]pyrimidine-5-carboxylate The sub-title compound was prepared by the method of example 9, part c) using the product of step b).
MS (APCI) 283.1 (M$^+$+H)

d) Ethyl 1-ethyl-6-[hydroxy(quinolin-4-yl)methyl]-3-methyl-2,4-dioxo-1,2,3,4-tetrahydrothieno[2,3-d]pyrimidine-5-carboxylate The sub-title compound was prepared by the method of example 9, part d) using the product of step c).
δ $^1H_{CDCl3}$ 1.21 (3H, t), 1.43 (3H, t), 3.38 (3H, s), 3.53 (1H, d), 3.75 (2H, m), 4.50 (2H, q), 6.79 (1H, d), 7.53 (2H, m), 7.85 (2H, m), 7.89 (2H, d), 9.03 (1H, d).

e) Ethyl 1-ethyl-3-methyl-2,4-dioxo-6-(quinolin-4-ylmethyl)-1,2,3,4-tetrahydrothieno[2,3-d]pyrimidine-5-carboxylate The sub-title compound was prepared by the method of example 9, part e) using the product of step d).
MS (ESI) 424.0 (M$^+$+H)

f) Sodium 1-ethyl-3-methyl-2,4-dioxo-6-(quinolin-4-ylmethyl)-1,2,3,4-tetrahydrothieno[2,3-d]pyrimidine-5-carboxylate The sub-title compound was prepared by the method of example 9, part f) using the product of step e).
MS (ESI) 396.0 (M$^+$+H)

g) 1-Ethyl-N-methoxy-N,3-dimethyl-2,4-dioxo-6-(quinolin-4-ylmethyl)-1,2,3,4-tetrahydrothieno[2,3-d]pyrimidine-5-carboxamide The sub-title compound was prepared by the method of example 9, part g) using the product of step f).
δ $^1H_{DMSO}$ 1.15 (3H, t), 2.99 (1H, s), 3.21 (3H, d), 3.31 (2H, d), 3.44 (2H, s), 3.73 (1H, s), 3.81 (2H, q), 4.60 (2H, s), 7.47 (1H, m), 7.78 (1H, m), 8.05 (1H, d), 8.28 (1H, m), 8.88 (1H, d). MS (APCI) 453.1 (M$^+$+H)

EXAMPLE 14 iii 1-(Cyclopropylmethyl)-N-methoxy-N,3-dimethyl-2,4-dioxo-6-(quinolin-4-ylmethyl)-1,2,3,4-tetrahydrothieno[2,3-d]pyrimidine-5-carboxamide a) 6-Chloro-1-(cyclopropylmethyl)-3-methylpyrimidine-2,4(1H,3H)-dione The sub-title compound was prepared by the method of example 9, part a) using 6-chloro-3-methyl uracil and cyclopropylmethyl bromide.
δ $^1H_{CDCl3}$ 0.48 (4H, m), 1.24 (1H, m), 3.33 (3H, s), 3.85 (1H, s), 5.93 (1H, s).

b) 1-(Cyclopropylmethyl)-6-mercapto-3-methylpyrimidine-2,4(1H,3H)-dione

The sub-title compound was prepared by the method of example 9, part c) using the product of step a).
δ $^1H_{CDCl3}$ 0.47 (4H, m), 1.31 (1H, m), 3.33 (3H, s), 4.18 (0.5H, s), 4.36 (2H, d), 5.77 (1.5H, s).

c) Ethyl 1-(cyclopropylmethyl)-3-methyl-2,4-dioxo-1,2,3,4-tetrahydrothieno[2,3-d]pyrimidine-5-carboxylate The sub-title compound was prepared by the method of example 9, part c) using the product of step b).
MS (APCI) 309.1 (M$^+$+H)

d) Ethyl 1-(cyclopropylmethyl)-6-[hydroxy(quinolin-4-ylmethyl]-3-methyl-2,4-dioxo-1,2,3,4-tetrahydrothieno[2,3-d]pyrimidine-5-carboxylate The sub-title compound was prepared by the method of example 9, part d) using the product of step c).
δ $^1H_{CDCl3}$ 0.35 (2H, m), 0.49 (2H, m), 1.11 (1H, m), 1.41 (3H, t), 3.38 (3H, d), 3.60 (1H, m), 3.77 (1H, m), 3.80 (1H, d), 4.48 (2H, q), 6.79 (1H, d), 7.52 (1H, m), 7.71 (1H, m), 7.83 (1H, m), 7.91 (1H, m), 8.16 (1H, m), 9.01 (1H, d).

e) Ethyl 1-(cyclopropylmethyl)-3-methyl-2,4-dioxo-6-(quinolin-4-ylmethyl)-1,2,3,4-tetrahydrothieno[2,3-d]pyrimidine-5-carboxylate The sub-title compound was prepared by the method of example 9, part e) using the product of step d).
MS (ESI) 450.0 (M+H)

f) Sodium 1-(cyclopropylmethyl)-3-methyl-2,4-dioxo-6-(quinolin-4-ylmethyl)-1,2,3,4-tetrahydrothieno[2,3-d]pyrimidine-5-carboxylate The sub-title compound was prepared by the method of example 9, part f) using the product of step e).
MS (ESI) 422.1 (M⁺+H)

g) 1-Ethyl-N-methoxy-N,3-dimethyl-2,4-dioxo-6-(quinolin-4-yl methyl)-1,2,3,4-tetrahydrothieno[2,3-d]pyrimidine-5-carboxamide The sub-title compound was prepared by the method of example 9, part g) using the product of step f).
δ $^1H_{DMSO}$ 1.15 (1H, m), 2.99 (1H, s), 3.22 (3H, d), 3.30 (2H, m), 3.45 (2H, s), 3.70 (3H, m), 4.60 (2H, s), 7.47 (1H, m), 7.64 (1H, t), 7.78 (1H, m) 8.05 (1H, d), 8.28 (1H, m), 8.88 (1H, d).
MS (APCI) 465.1 (M⁺+H)

EXAMPLE 15

6-[4,5-Dichloro-2-(hydroxymethyl)-][H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide

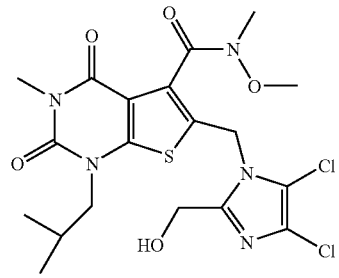

a) 4,5-Dichloro-1H-imidazole-2-methanol

Potassium hydroxide (0.12 g, 2.14 mmol) in water (4 ml) was added to 4,5-dichloroimidazole, and the suspension was stirred for 35 min. Paraformaldehyde (0.11 g, 3.66 mmol) was added portionwise and the reaction mixture was stirred over night, then acidified with dilute HCl to pH 1 and then concentrated in vacuo to give a white solid, 0.6 g (98%).
δ $^1H_{CDCl_3}$ 4.36 (2H, s)

b) 6-[4,5-Dichloro-2-(hydroxymethyl)-1H-imidazol-1-ylmethyl]-1,2,3,4-tetrahydro-3-methyl-1-(2-methylpropyl)-2,4-dioxo-thieno[2,3-d]pyrimidine-5-carboxylic acid methyl ester Potassium carbonate (0.14 g, 3.1 mmol) and the product of part a) (0.51 g, 3.09 mmol), were added to a solution of the product of example 1 part b) in DMF, and the reaction mixture was stirred for 16 h. The solid precipitate formed was filtered, and the filtrate was concentrated in vacuo to give an orange solid 0.6 g, contains DMF.
δ $^1H_{CDCl_3}$ 0.99 (6H, m), 2.19-2.31 (1H,m), 3.4 (3H,s), 3.72(2H,d), 4.0(3H,s), 4.68(2H,s), 5.45(2H,s).

c) 6-[4,5-Dichloro-2-(hydroxymethyl)-1H-imidazol-1-ylmethyl]-1,2,3,4-tetrahydro-3-methyl-1-(2-methylpropyl)-2,4-dioxo-thieno[2,3-d]pyrimidine-5-carboxylic acid Prepared from the product of step b) following the procedure of example 3, step d).
MS(ESI) 484 [M+H]⁺ d) 6-[4,5-Dichloro-2-(hydroxymethyl)-1H-imidazol-1-ylmethyl]-5-[[(4S)-4-hydroxyisoxazolidin-2-yl]carbonyl]-3-methyl-1-(2-methylpropyl)-thieno[2,3-d]pyrimidine-2,4(1H,3H)-dione Prepared form the product of step c) using the procedure of example 1 part e). The product was purified by reverse phase preparative HPLC eluting with ammonium acetate: acetonitrile (70:30) to give the title compound as a white solid.
δ $^1H_{DMSO}$ 0.91 (6H, m), 2.16-2.22 (1H,m), 3.2-3.6 (3H, br,s), 3.23 (3H,s), 3.68-3.73 (2H,m), 4.52(2H,s), 5.378-5.39 (3H,m).
MS(APCI) 505 [M+H]⁺

EXAMPLE 16

1,2,3,4-Tetrahydro-N-methoxy-N,3-dimethyl-6-[2-methyl-1H-pyrrolo[2,3-b]pyridin-3-ylmethyl]-2,4-dioxo-1-propyl-thieno[2,3-d]pyrimidine-5-carboxamide

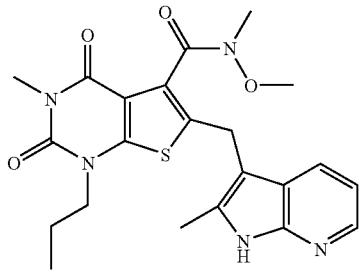

a) Methyl 3-methyl-6-[2-methyl-1H-pyrrolo[2,3-b]pyridin-3-ylmethyl]-2,3-dioxo-1-propyl-1,2,3,4-tetrahydrothieno[2,3-d]pyrimidine-5-carboxylate The subtitle compound was prepared from the product of example 7 part c) and 2-methyl-1H-pyrrolo[2,3-d]pyridine using the method of example 3 part a).
MS(ESI) 427 [M+H]⁺ δ $^1H_{D6\text{-}DMSO}$ 0.82 (6H, t), 1.59 (2H, sextet), 2.38 (3H, s), 3.19 (3H, s), 3.72 (2H, t), 3.83 (3H, s), 4.17 (2H, s); 6.98 (1H, dd), 7.75 (1H, d), 8.10 (1H, dd), 11.48 (1H, s).

b) Sodium 3-methyl-6-[2-methyl-1H-pyrrolo[2,3-d]pyridin-3-ylmethyl]-2,4-dioxo-1-propyl-1,2,3,4-tetrahydrothieno[2,3-d]pyrimidine-5-carboxylate The subtitle compound was prepared from the product of step a using the method of example 1 part d.
MS(ESI) 413 [M+H]⁺ δ $^1H_{D_2O}$ 0.77 (3H, t), 1.55 (1H, sextet), 2.43 (3H, s), 3.34 (3H, s), 3.63 (2H, t), 4.16 (2H, s), 7.08 (1H, dd), 7.89 (1H, d), 8.06 (1H, d).

c) 1,2,3,4-tetrahydro-N-methoxy-N,3-dimethyl-6-[2-methyl-1H-pyrrolo[2,3-b]pyridin-3-ylmethyl]-2,4-dioxo-1-propyl-thieno[2,3-d]pyrimidine-5-carboxamide The subtitle compound was prepared by the method of example 1 part e using the product of part b.

δ $^1H_{DMSO}$ 0.77 (3H, t), 1.55 (1H, sextet), 2.43 (3H, s), 3.34 (3H, s), 3.63 (2H, t), 4.16 (2H, s), 7.08 (1H, dd), 7.89 (1H, d), 8.06 (1H, d).

EXAMPLE 17

1,2,3,4-Tetrahydro-N-methoxy-N,3-dimethyl-1-(1-methylethyl)-6-[2-methyl-1H-pyrrolo[2,3-b]pyridin-3-ylmethyl]-2,4-dioxo-thieno[2,3-d]pryimidine-5-carboxamide

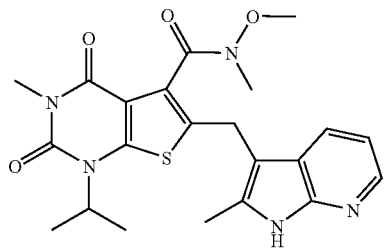

a) 1,2,3,4-Tetrahydro-3-methyl-1-(1-methylethyl)-6-[2-methyl-1H-pyrrolo[2,3-b]pyridin-3-ylmethyl]-2,4-dioxo-thieno[2,3-d]pyrimidine-5-carboxylic acid methyl ester Prepared from the product of example 6 part c) following the procedure of example 3 part a) to give the sub-title compound as a solid.

MS(ESI) 427 [M+H]$^+$ δ $^1H_{DMSO}$ 1.48 (6H, d), 2.49 (3H, s), 3.36 (3H, s), 3.99 (3H, s), 4.11 (2H, s), 4.20 (1H, s, br), 7.03-7.06 (1H, m), 7.79 (1H, d), 8.23 (1H, d), 9.10(1H, s)

b) 1,2,3,4-Tetrahydro-3-methyl-1-(1-methylethyl)-6-[2-methyl-1H-pyrrolo[2,3-b]pyridin-3-ylmethyl]-2,4-dioxo-thieno[2,3-d]pyrimidine-5-carboxylic acid Prepared from the product of part a) following the procedure of example 1 part d) to give the sub-title compound as a solid.

MS(ESI) 413 [M+H]$^+$ c) 1,2,3,4-Tetrahydro-N-methoxy-N,3-dimethyl-1-(1-methylethyl)-6-[2-methyl-1H-pyrrolo[2,3-b]pyridin-3-ylmethyl]-2,4-dioxo-thieno[2,3-d]pyrimidine-5-carboxamide The title compound was prepared from the product of part b) following the procedure of example 1 part e).

MS (APCI) 456 [M+H]$^+$ δ $^1H_{DMSO}$ 1.38-1.42 (6H, m), 2.40 (3H, s), 3.00 (3H, s), 3.17-3.18 (3H, m), 3.30 (2H, s), 3.45 (2H, s), 3.79 (1H, s), 4.004.15 (2H, m), 4.30 (1H, s, br), 6.96-6.99 (1H, s), 7.80-7.86 (1H, m), 8.09-8.10 (1H, m), 11.46 (1H, s)

EXAMPLE 18

1,2,3,4-Tetrahydro-N-methoxy-N,3-dimethyl-1-(2-methylpropyl)-2,4-dioxo-6-[2-(trifluoromethyl)phenylmethyl]thieno[2,3-d]pyrimidine-5-carboxamide

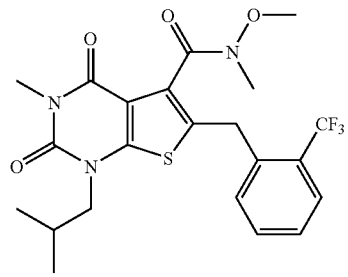

a) 1,2,3,4-Tetrahydro-3-methyl-1-(2-methylpropyl)-2,4-dioxo-6-[2-(trifluoromethyl)phenylmethyl]thieno[2,3-d]pyrimidine-5-carboxylic acid To a solution of 5-bromo-3-methyl-1-(2-methylpropyl)-6-[[2-(trifluoromethyl)phenyl]methyl]-thieno[2,3-d]pyrimidine-2,4(1H,3H)-dione (WO 0183489) in THF (60 ml) was added isopropylmagnesiumcholride (2M solution in THF, 3.35 ml) dropwise at 0° C. under nitrogen. After 5 min the mixture was treated with a stream of carbon dioxide for 10 min. The reaction mixture was quenched with water, acidified 2N HCl and extracted into ethyl acetate (×3). The combined organic extracts were washed with dilute HCl, brine, dried (MgSO$_4$) and concentrated in vacuo to give the subtitle compound as a yellow solid (2.48 g).

MS (ESI) 427 [M+H]$^+$ b) 1,2,3,4-Tetrahydro-N-methoxy-N,3-dimethyl-1-(2-methylpropyl)-2,4-dioxo-6-[2-(trifluoromethyl)phenylmethyl]thieno[2,3-d]pyrimidine-5-carboxamide The title compound was prepared from the product of part a) following the procedure of example 1 part e).

MS (APCI) 456 [M+H]$^+$ δ $^1H_{DMSO}$ 0.86-0.88 (6H, m), 2.12 (1H, heptet), 3.00 (1H, s), 3.21 (3H, s), 3.26 (2H, s), 3.43 (2H, s), 3.59-3.73 (3H, m), 4.22 (2H, s), 7.48-7.54 (2H, m), 7.64-7.70 (1H, m), 7.75 (1H, d)

EXAMPLE 19

1,2,3,4-Tetrahydro-N-methoxy-N,3-dimethyl-1-(2-methylpronyl)-2,4-dioxo-6-(benzyl)thieno[2,3-d]pyrimidine-5-carboxamide

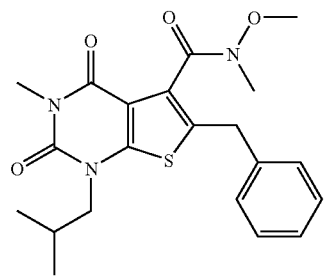

a) 1,2,3,4-Tetrahydro-N-methoxy-N,3-dimethyl-1-(2-methylpropyl)-2,4-dioxo-6-(benzyl)thieno[2,3-d]pyrimidine-5-carboxamide The title compound was prepared from 1,2,3,4-tetrahydro-3-methyl-1-(2-methylpropyl)-2,4-dioxo-6-(phenylmethyl)thieno[2,3-d]pyrimidine-5-carboxylic acid (WO 9854190) following the procedure of example 1 part e).

MS (APCI) 456 [M+H]$^+$ δ $^1H_{DMSO}$ 0.87-0.90 (6H, m), 2.10-2.17 (1H, m), 3.21 (1H, s), 3.21-3.22 (3H, m), 3.28-3.32 (2H, m), 3.39 (2H, m), 3.59-3.76 (3H, m), 4.02-4.05 (2H, m), 7.23-7.35 (5H, m).

EXAMPLE 20 i

Methyl 4-[1,2,3,4-tetrahydro-5-[(N-methoxy-N-methylamino)carbonyl]-3-methyl-1-(2-methylpropyl)-2,4-dioxothieno[2,3-d]pyrimidin-6-yl]hydroxy)methyl]-1-methyl-1H-pyrrole-2-carboxylate

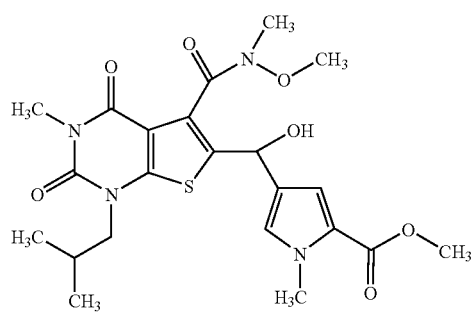

a) 1,2,3,4-Tetrahydro-N-methoxy-N,3-dimethyl-1-(2-methylpropyl)-2,4-dioxo-thieno[2,3-d]pyrimidine-5-carboxamide Trimethyl aluminium (7.55 ml of 2M solution in toluene) was added to N,O-dimethylhydroxylamine hydrochloride (1.415 g) in dry toluene (60 ml) at 0° C. under nitrogen. After stirring at 0° C. for 1 h the temperature was raised to ambient and the mixture was stirred for a further 1 h. The product of Example 2 part a) (1.5 g) was added in portions. After 2 h the reaction was poured onto ice-cold 2M HCl and stirred whilst it warmed to ambient temperature. The mixture was extracted into ethyl acetate, and the combined extracts were washed with brine, dried and evaporated to afford the subtitle compound (1.359 g).

MS (APCI) 326 [M+H]$^+$ δ $^1H_{DMSO}$ 0.93(6H,d), 2.22(1H, septet), 3.22(5H,s), 3.31(2H,s), 3.42(2H,br s), 4.03(2H,d), 7.35(1H,s).

b) Methyl 4-[1,2,3,4-tetrahydro-5-[N-methoxy-N-methylaminocarbonyl]-3-methyl-1-(2-methylpropyl)-2,4-dioxothieno[2,3-d]pyrimidin-6-yl](hydroxy)methyl-1-methyl-1H-pyrrole-2-carboxylate The product of part a) (240 mg) and methyl 4-formyl-1-methyl-1H-pyrrole-2-carboxylate (250 mg) in dry THF (40 ml) at −78° C. were treated with lithium diisopropylamide (0.74 ml of 2M) for 5 h. The reaction was poured into excess saturated aqueous ammonium chloride solution and extracted into ethyl acetate. The combined extracts were washed with brine, dried and evaporated to afford a solid residue which was purified by chromatography (SiO2/50-100% ethyl acetate in isohexane) to afford the title compound (56 mg).

MS (APCI) 475 [M−OH]$^+$ δ $^1H_{CDCl_3}$ 0.95-0.98(6H,d), 2.29(1H, septet), 2.88 and 3.32(1H, 2×d), 3.32-3.92(17H, m), 5.30-6.01(1H,m), 6.86-6.88(1H,m), 6.91-6.95(1H,m).

EXAMPLE 20 ii

Methyl 1-methyl-4-[1,2,3,4-tetrahydro-5-[(methoxymethylamino)carbonyl]-3-methyl-1-(2-methylpropyl)-2,4-dioxothieno[2,3-d]pyrimidin-6-ylmethyl]-1H-pyrrole-2-carboxylate

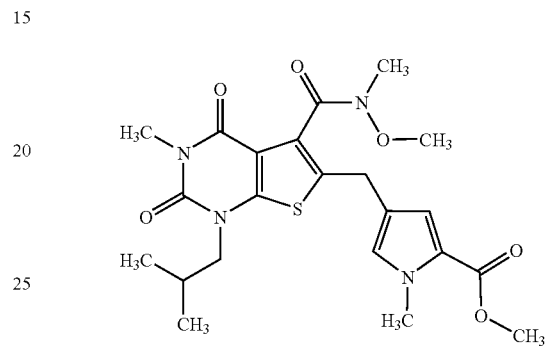

a) Methyl 1-methyl-4-[1,2,3,4-tetrahydro-5-[(N-methoxy-N-methylamino)carbonyl]-3-methyl-1-(2-methylpropyl)-2,4-dioxothieno[2,3-d]pyrimidin-6-ylmethyl]-1H-pyrrole-2-carboxylate acid The product of Example 20 (i) part b) (95 mg) was treated with trifluoroacetic acid (3 ml) and triethylsilane (1.5 ml) at room temperature for 5 h. Evaporation in vacuo gave a residue which was purified by Reverse Phase HPLC (25%-95% acetonitrile-1% aqueous ammonium acetate eluant) to afford the title compound (63 mg).

MS (APCI) 477 [M+H]$^+$ δ $^1H_{CDCl_3}$ 0.96(6H,d),2.27(1H, septet), 3.10 and 3.40(3H, 2×s),3.38(3H,s),3.49 and 3.97 (3H, 2×s), 3.55-3.60(1H,m), 3.79(3H,s), 3.88(3H,s), 3.97-4.01(3H,m), 6.72(1H,s), 6.82-6.89(1H,m).

EXAMPLE 21

Methyl 2,5-dimethyl-4-[1,2,3,4-tetrahydro-5-[(N-methoxy-N-methyl amino)carbonyl]-3-methyl-1-(2-methylpropyl)-2,4-dioxothieno[2,3-d]pyrimidin-6-ylmethyl]-1H-pyrrole-3-carboxylate

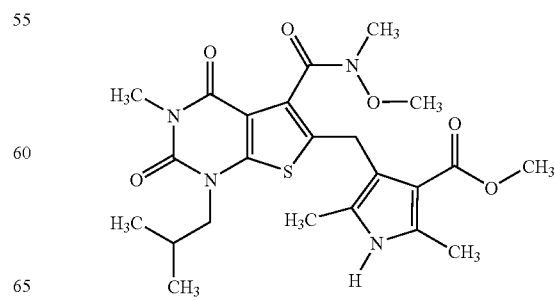

a) 3-Methyl 1-phenylmethyl 4-formyl-2,5-dimethyl-1H-pyrrole-1,3-dicarboxylate Methyl 2,5-dimethyl-4-formyl-pyrrole-3-carboxylate (500 mg) in THF (5 ml) under nitrogen was added to a suspension of sodium hydride (120 mg of 60% oil dispersion) in dry THF (10 ml). When effervescence had ceased the suspension was cooled to 10° C., and benzyl chloroformate (0.437 ml) was added. After stirring at room temperature for 4 h, ethanol (0.5 ml) was added and then the reaction was poured into water. Extraction into ethyl acetate, washing the extracts with brine, drying and evaporation gave the crude product. Purification by chromatography (SiO2/30%-50% ethyl acetate in isohexane) afforded the subtitle compound (0.6 g).

MS (APCI) 316 [M+H]$^+$ δ $^1$H$_{CDCl3}$ 2.60(3H,s), 2.62(3H, s), 3.86(3H, s), 5.43(2H,s), 7.26-7.45(5H,m), 10.31(1H, s).

b) 3-Methyl 1-(phenylmethyl)4-[1,2,3,4-tetrahydro-5-[N-methoxy-N-methylaminocarbonyl]-3-methyl-1-(2-methylpropyl)-2,4-dioxothieno[2,3-d]pyrimidin-6-yl](hydroxy)methyl]-2,5-dimethyl-1H-pyrrole-1,3-dicarboxylate The product of step a) (0.6 g) and the product of Example 20(i) step a) were reacted together using the method of Example 2 part b) to afford the subtitle compound after purification by chromatography (SiO2/50%-100% ethyl acetate in isohexane) (195 mg).

MS (APCI) 623 [M−OH]$^+$ c) 3-Methyl 1-(phenylmethyl) 2,5-dimethyl-4-[1,2,3,4-tetrahydro-5-[N-methoxy-N-methylamino)carbonyl]-3-methyl-1-(2-methylpropyl)-2,4-dioxothieno[2,3-d]pyrimidin-6-ylmethyl]-1H-pyrrole-1,3-dicarboxylate The product of step b) was converted to the subtitle compound by the method of Example 20(ii) part a), and purified by chromatography (SiO2/50%-100% ethyl acetate in isohexane) (125 mg).

MS (APCI) 625 [M+H]$^+$ δ $^1$H$_{CDCl3}$ 0.93(6H,d), 2.21(1H, septet), 2.29(3H,s), 2.67(3H, s), 3.19 and 3.36(3H,2×s), 3.41(3H,s), 3.47 and 3.95(3H, 2×s), 3.58(1H,dd), 3.79(H, dd), 3.79(3H,s), 4.09-4.19(2H,m), 5.38(2H,s), 7.38-7.42 (5H,m).

d) Methyl 2,5-dimethyl-4-[[1,2,3,4-tetrahydro-5-[N-methoxy-N-methylaminocarbonyl]-3-methyl-1-(2-methylpropyl)-2,4-dioxothieno[2,3-d]pyrimidin-6-yl]methyl]-1H-pyrrole-3-carboxylate The product of step c) (189 mg) in dry ethanol (18 ml) was treated with a slurry of 10% Pd/C (20 mg) in dry ethanol (2 ml) and hydrogenated at 4 bar for 75 min. Filtration from catalyst and evaporation gave a residue which was purified by chromatography in two stages: firstly (SiO2/3:1 ethyl acetate-isohexane) and secondly (SiO2/2:1 isohexane-acetone) to afford the title compound (85 mg).

MS (APCI) 491 [M+H]$^+$ δ $^1$H$_{CDCl3}$ 0.94(6H,d), 2.15 and 2.17(3H, 2×s), 2.24(1H, septet), 2.48(3H,s), 3.10 and 3.41 (3H,2×s), 3.37(3H,s), 3.51 and 3.96(3H, 2×s), 3.58-3.63(1H, m), 3.75-3.8(1H,m), 3.77(3H,s), 4.01-4.07(1H,m), 4.18-4.29(1H,m).

EXAMPLE 22

1,2,3,4-Tetrahydro-N-methoxy-N,3-dimethyl-1-(2-methylpropyl)-2,4-dioxo-6-[2-oxo-3(2H)-benzoxazolylmethyl]-thieno[2,3-d]pyrimidine-5-carboxamide

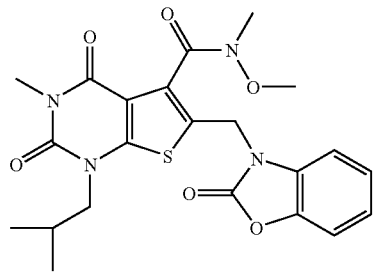

a) 1,2,3,4-tetrahydro-3-methyl-1-(2-methylpropyl)-2,4-dioxo-6-[2-oxo-3(2H)-benzoxazolyl)methyl]-thieno[2,3-d]pyrimidine-5-carboxylic acid, methyl ester The subtitle compound was synthesised by the method of example 1 c) using the product of example 1 part b) and benzoxazolone. The product was isolated by SiO2 chromatography eluting with ethyl acetate/i-hexane (3:2), followed by recrystallisation with diethyl ether to so give the sub-title compound.

MS(ESI) 444 [M+H]$^+$ δ $^1$H$_{CDCl3}$ 0.95 (6H, d), 2.25(1H, septet), 3.39(3H,d), 3.73(2H,d), 4.04(3H,s), 5.18(2H,s), 7.18 (4H,m).

b) 1,2,3,4-tetrahydro-3-methyl-1-(2-methylpronyl)-2,4-dioxo-6-[2-oxo-3(2H)-benzoxazolylmethyl]-thieno[2,3-d]pyrimidine-5-carboxylic acid Prepared by the method of example 1 part d) using the product of part a)

MS(ESI) 430 [M+H]$^+$ c) 1,2,3,4-tetrahydro-N-methoxy-N,3-dimethyl-1-(2-methylpropyl)-2,4-dioxo-6-[2-oxo-3(2H)-benzoxazolylmethyl]-thieno[2,3-d]pyrimidine-5-carboxamide Prepared by the method of example 1 part e) using the product of part b).

MS(ESI) 473 [M+H]$^+$ δ $^1$H$_{DMSO}$ 0.91 (6H, d), 2.20(1H, septet), 3.16(3H,s), 3.23(3H,s), 3.49(3H,s), 3.71(2H,d), 5.1 (2H,s), 7.15(2H, m) and 7.27(2H, d).

EXAMPLE 23

1,2,3,4-Tetra hydra-N-methoxy-N,3-dimethyl-1-(2-methylpropyl)-2,4-dioxo-6-[(2,4,5-trichloro-1H-imidazol-1-yl)methyl]-thieno[2,3-d]pyrimidine-5-carboxamide

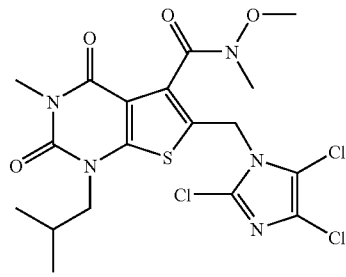

a) Methyl 1,2,3,4-tetrahydro-3-methyl-1-(2-methyl-propyl)-2,4-dioxo-6-[(2,4,5-trichloro-1H-imidazol-1-yl)methyl]-thieno[2,3-d]pyrimidine-5-carboxylate The subtitle compound was made by the method of Example 1, part c), using 2,4,5-trichloro-imidazole, and the product of Example 1, part b). and purified by chromatography (SiO$_2$/20%-50% ethyl acetate-isohexane)

MS (APCI) 479/481/483 [M+H]$^+$ δ $^1$H$_{CDCl3}$ 0.97(6H,d), 2.25(1H, septet), 3.39(3H,s), 3.74(2H,d), 3.99(3H,s), 5.37 (2H,s).

b) 1,2,3,4-Tetrahydro-3-methyl-1-(2-methylpropyl)-2,4-dioxo-6-[2,4,5-trichloro-1H-imidazol-1-ylmethyl]thieno[2,3-d]pyrimidine-5-carboxylic acid The product of part a) (170 mg) was treated with lithium hydroxide monohydrate (31 mg) in water (0.75 ml), methanol (0.75 ml) and THF (2.25 ml) for 4 h at room temperature. The reaction was acidified with glacial acetic acid and evaporated to dryness. The residue was dissolved in water and extracted into dichloromethane. Drying and evaporation gave the subtitle compound (110 mg).

MS (APCI) 465/467/469 [M+H]$^+$ c) 1,2,3,4-Tetrahydro-N-methoxy-N,3-dimethyl-]-(2-methylpropyl)-2,4-dioxo-6-[(2,4,5-trichloro-1H-imidazol-1-yl)methyl]-thieno[2,3-d]pyrimidine-5-carboxamide The title compound was prepared by the method of Example 1, part e, using the product of step b) above and purified by chromatography (SiO$_2$/50%-66% ethyl acetate-isohexane).

MS (APCI) 508/510/512 [M+H]$^+$ δ $^1$H$_{CDCl3}$ 0.98(6H,d), 2.28(1H, septet), 3.39(3H,s), 3.43(3H,s), 3.46(3H,s), 3.64 (1H,dd), 3.86(1H,dd), 5.18(1H,d), 5.37(1H,d).

EXAMPLE 24 i

6-[4,5-Dichloro-2-methyl-1H-imidazol-1-ylmethyl]-N-(2-hydroxyethyl)-1-isobutyl-N-methoxy-3-methyl-2,4-dioxo-1,2,3,4-tetrahydrothieno[2,3-4-pyrimidine-5-carboxamide

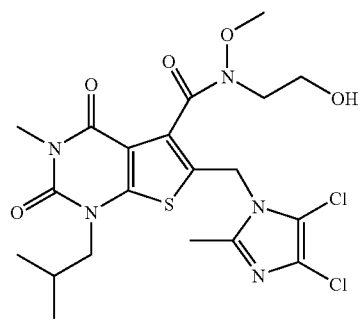

a) 6-[4,5-Dichloro-2-methyl-1H-imidazol-1-ylmethyl]-1-isobutyl-N-methoxy-3-methyl-2,4-dioxo-1,2,3,4-tetrahydrothieno[2,3-d]pyrimidine-5-carboxamide Prepared from the product of example 1 part d) and methoxylamine hydrochloride following the procedure of example 1 part e).

δ $^1$H$_{CDCl3}$ 0.87 (6H, d), 2.21 (1H, n), 2.37 (3H, s), 3.47 (3H, s), 3.75 (2H, d), 3.91 (3H, s), 5.80 (2H, s), 13.45 (1H, s).

b) 6-[4,5-Dichloro-2-methyl-1H-imidazol-1-ylmethyl]-N-(2-hydroxyethyl)-1-isobutyl-N-methoxy-3-methyl-2,4-dioxo-1,2,3,4-tetrahydrothieno[2,3-d]pyrimidine-5-carboxamide Potassium carbonate (72 mg) and 2-iodoethanol (0.072 ml) were added to a solution of the product of part a) (72 mg) in acetone (3 ml). The mixture was stirred at reflux for 10 h, cooled to room temperature then diluted with water (10 ml) and extracted with ethyl acetate (2×10 ml). Organic extracts were dried over anhydrous magnesium sulfate, filtered and evaporated under reduced pressure. The residue was purified by normal-phase HPLC with gradient dichloromethane/ethanol elution to give the title compound (43 mg) as a foam.

MS (APCI) 516/518/520 [M−H]$^-$ δ $^1$H$_{CDCl3}$ 0.87 0.98 (6H, d), 2.27 (1H, n), 2.43 (3H, s), 3.40 (3H, s), 3.41 (3H, s), 3.58 (1H, dt), 3.67 (1H, dd), 3.83 (1H, dd), 3.94-3.99 (2H, m), 4.03-4.07 (1H, m), 4.36 (1H, dt), 5.25 (2H, ABq).

EXAMPLE 24 ii

6-[4,5-Dichloro-2-methyl-1-H-imidazol-1-ylmethyl]-N-(2-hydroxyethoxy)-1-isobutyl-N,3-dimethyl-2,4-dioxo-1,2,3,4-tetrahydrothieno[2,3-4-pyrimidine-5-carboxamide

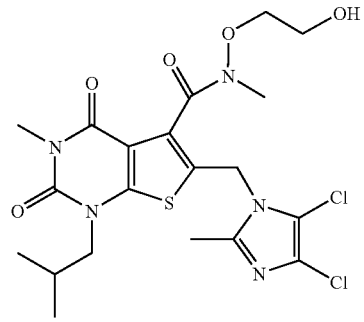

a) 6-[4,5-dichloro-2-methyl-1H-imidazol-1-ylmethyl]-N-hydroxy-1-isobutyl-N,3-dimethyl-2,4-dioxo-1,2,3,4-tetrahydrothieno[2,3-d]pyrimidine-5-carboxamide Oxalyl chloride (0.1 62 ml) was added to a stirred solution of the product of example 1 part d) (415 mg) and dimethylformamide (0.01 ml) in dichloromethane (4 ml). After 1 h the solution was evaporated under reduced pressure. The residue was dissolved in anhydrous tetrahydrofuran (3 ml) and 1 ml of the solution was added to a stirred solution of N-methylhydroxylamine hydrochloride (129 mg) in saturated aqueous sodium bicarbonate solution (2 ml). After 1 h, the mixture was diluted with water (10 ml) and extracted with ethyl acetate (3×10 ml). Organic extracts were dried over anhydrous magnesium sulfate, filtered and evaporated under reduced pressure to give the sub-title compound (129 mg).

MS(ESI) 474/476/478 [M+H]$^+$ δ $^1$H$_{DMSO}$ 0.88-0.93 (6H, m), 2.10-2.20 (1H, m), 2.32 (2.25H, s), 2.36 (0.75H, s), 2.98

(0.75H, s), 3.22 (3H, s), 3.26 (0.75H, s), 3.63-3.78 (1H, m), 5.22 (1.5H, s), 5.26 (0.5H, s), 9.80 (0.75H, s), 10.00 (0.25H, s).

b) 6-[4,5-Dichloro-2-methyl-1H-imidazol-1-ylmethyl]-N-(2-hydroxyethoxy)-1-isobutyl-N,3-dimethyl-2,4-dioxo-1,2,3,4-tetrahydrothieno[2,3-d]pyrimidine-5-carboxamide Potassium carbonate (125 mg) and 2-iodoethanol (0.125 ml) were added to a solution of the product of part a) (125 mg) in acetone (5 ml). The mixture was stirred for 16 h, diluted with water (10 ml) and extracted with ethyl acetate (3×10 ml). Organic extracts were dried over anhydrous magnesium sulfate, filtered and evaporated under reduced pressure. The residue was purified by reverse-phase HPLC with gradient 0.1% aqueous ammonium acetate/acetonitrile elution and the resulting oil triturated with ether to give the title compound (75 mg) as a solid.

MS (APCI) 517/519/521 [M+H]$^+$ δ $^1$H$_{DMSO}$ 0.89-0.91 (6H, m), 2.10-2.21 (1H, m), 2.33 (2H, s), 2.36 (1H, s), 3.02 (1H, s), 3.21 (2H, s), 3.22 (1H, s), 3.27 (1H, s), 3.20-3.34 (1.33H, m), 3.57-3.78 (4H, m), 4.03-4.13 (0.67H, m), 4.50 (0.67H, t), 4.79 (0.33H, t), 5.20-5.32 (2H, m),

EXAMPLE 24 iii

6-[4,5-Dichloro-2-methyl-1H-imidazol-1-ylmethyl]-N-ethyl]-1,2,3,4-tetrahydro-N-methoxy-3-methyl-1-(2-methylpropyl)-2,4-dioxo-thieno[2,3-d]pyrimidine-5-carboxamide

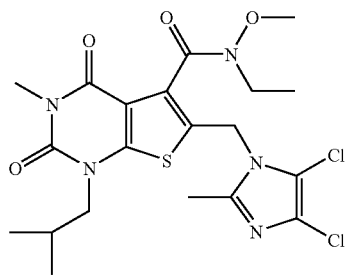

a) 6-[4,5-dichloro-2-methyl-1H-imidazol-1]-ylmethyl]-1,2,3,4-tetrahydro-N-methoxy-3-methyl-1-(2-methyl]propyl)-2,4-dioxo-thieno[2,3-d]pyrimidine-5-carboxamide Prepared by the method of example 1 part e) using methoxylaminehydrochloride and the product of example 1 part d. The subtitle compound was obtained as a white solid after SiO$_2$ chromatography eluting with (1-5% methanol in DCM).

δ $^1$H$_{CDCl3}$ 0.5(6H,d), 2.21(1H,m), 2.37(3H,s), 3.47(3H,s), 3.75(2H,d), 3.91(3H,s), 5.8(2H,s) and 13.45(1H,s).

b) 6-[4,5-dichloro-2-methyl-1H-imidazol-1-ylmethyl]-N-ethyl-1,2,3,4-tetrahydro-N-methoxy-3-methyl-1-(2-methylpropyl)-2,4-dioxo-thieno[2,3-d]pyrimidine-5-carboxamide The product of part a) (100 mg) was added to a stirred solution of NaH (60% dispersion in mineral oil, 8.4 mg) in THF (5 ml) and the reaction mixture was stirred under nitrogen for 30 min. Ethyl iodide (0.2 ml) was added and the reaction mixture was heated at reflux for 16 h. The reaction mixture was quenched with ethanol and concentrated in vacuo. The reaction mixture was dissolved in water and extracted with ethyl acetate. The organics were washed with brine and concentrated in vacuo. The title compound was obtained as a white solid after SiO$_2$ chromatography eluting With (20% ethanol in DCM).

MS(ESI) 503 [M+H]$^+$ δ $^1$H$_{CDCl3}$ 0.98(6H,d), 1.39(3H,t), 2.26(1H,m), 2.4(3H,s), 3.39(3H,s), 3.49(3H,s), 3.63(1H,m), 3.82(2H,m), 3.99(1H,m) and 5.17(2H,m).

The invention claimed is:

1. A compound of formula (1)

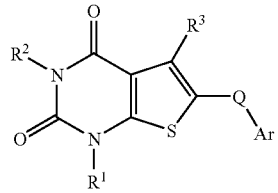

wherein:
$R^1$ and $R^2$ each independently represent a $C_{1-6}$alkyl, $C_{3-6}$alkenyl, $C_{3-6}$cycloalkyl$C_{1-3}$alkyl or $C_{3-6}$cycloalkyl; each of which may be optionally substituted by 1 to 3 halogen atoms;

$R^3$ a group —CON($R^{10}$)Y$R^{11}$ or —SO$_2$N($R^{10}$)Y$R^{11}$;

wherein Y is O, S or NR$_{12}$ wherein $R^{12}$ is hydrogen or $C_{1-6}$alkyl;

and $R^{10}$ and $R^{11}$ are independently $C_{1-6}$alkyl optionally substituted by halo, hydroxy, amino, $C_{1-6}$alkylamino or di-($C_{1-6}$alkyl)amino;

Q is —CO— or —C($R^4$)($R^5$)— wherein $R^4$ is a hydrogen atom or $C_{1-4}$alkyl and $R^5$ is a hydrogen atom or hydroxy group;

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl optionally substituted by 1, 2 or 3 hydroxy groups, $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or a 5 or 6 membered aromatic ring containing up to 4 heteroatoms independently selected from the group consisting of nitrogen, oxygen and sulphur;

p is 1 to 4;

$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring;

$R^8$ and $R^9$ each independently represent a hydrogen atom, $C_{1-4}$alkanoyl or $C_{1-4}$ alkyl, or together with the nitrogen atom to which they are attached form a 5- to 7-membered saturated heterocyclic ring;

or a pharmaceutically acceptable salt thereof.

2. A compound according to claim 1 wherein $R^2$ is methyl or ethyl.

3. A compound according to claim 1 wherein $R^1$ is ethyl, n-propyl, 1-methylethyl, 2-methylpropyl, 2,2-dimethylpropyl, cyclopropylmethyl, trifluoromethyl 2,2,2-trifluoroethyl, 2-chloroethyl, 2-chloropropyl or 3,3,3-trifluoropropyl.

4. A compound according to claim 1 wherein Q is —CO— or —CH$_2$—.

5. A compound according to claim 1 wherein $R^{10}$ is C$_{1-4}$alkyl optionally substituted by hydroxy.

6. A compound according to claim 1 wherein $R^{11}$ is C$_{1-4}$alkyl optionally substituted by hydroxy.

7. A compound according to claim 1 wherein Y is O.

8. A compound according to claim 1 wherein $R^3$ is —CON(Me)OMe, —CON(Et)OMe, —CON(OEt)Me, —CON(Et)OEt, —CON(CH$_2$CH$_2$OH)OEt, —CON(CH$_2$CH$_2$OH)Me, —CON(OCH$_2$CH$_2$OH)Me or —CON(OCH$_2$CH$_2$OH)Et.

9. A compound according to claim 1 wherein Ar contains at least 1 ring nitrogen.

10. A compound according to claim 1 wherein Ar contains at least 2 ring nitrogen.

11. A compound according to claim 1 wherein Ar is selected from the group consisting of imidazolyl, pyrazolyl, pyrrolyl, isoxazolyl, phenyl, quinolyl, indolyl, benzimidazolyl, indazolyl, benztriazolyl, 2,3-dihydrothiazolyl, 2,3-dihydrobenzoxazolyl, pyrrolo [2,3-b]pyridyl, imidazo [1,2-a]pyridyl, imidazo [4,5-b]pyridyl, 2,3-dihydrothiazolo[5,4-b]pyridyl, 2,3-dihydropyrazinyl, 2,3-dihydrobenzothiazolyl and 2,3-dihydrobenzimidazolyl, each ring system being optionally substituted according to claim 1.

12. A compound according to claim 1 wherein Ar is substituted by 1, 2 or 3 substituents independently selected from C$_{1-4}$alkyl optionally substituted by 1 or 2 hydroxy groups, C$_{1-4}$alkoxy, halogen, trihaloalkyl, C$_{1-4}$alkylthio, C$_{1-4}$alkoxycarbonyl, C$_{2-4}$alkanoyl, oxo, thioxo, cyano, —NHR$^7$ and —(CH$_2$)pN(R$^8$)R$^9$ wherein p is 1 or 2, hydroxy, C$_{1-4}$alkylsulphonyl, carbamoyl, C$_{1-4}$alkylcarbamoyl, di-(C$_{1-4}$alkyl)carbamoyl, carboxy, and a 5 or 6 membered aromatic ring containing up to 4 heteroatoms independently selected from the group consisting of nitrogen, oxygen and sulphur.

13. A compound according to claim 1 which is:

6-[(4,5-dichloro-2-methyl-1H-imidazol-1-yl)methyl]-1,2,3,4-tetrahydro-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-2,4-dioxo-6-(4-quinolinylmethyl)thieno[2,3-d]pyrimidine-5-carboxamide;

1,2,3,4-tetrahydro-N-methoxy-N,3-dimethyl-1-(2-methylpropyl)-2,4-dioxo-6-(1H-pyrrolo[2,3-b]pyridin-3-ylmethyl)-thieno[2,3-d]pyrimidine-5-carboxamide;

1,2,3,4-tetrahydro-6-(1H-indol-3-ylmethyl)-N-methoxy-N,3-dimethyl-1-(2-methylpropyl)-2,4-dioxo-thieno[2,3-d]pyrimidine-5-carboxamide;

1,2,3,4-tetrahydro-6-(1H-indol-3-ylcarbonyl)-N-methoxy-N,3-dimethyl-1-(2-methylpropyl)-2,4-dioxo-thieno[2,3-d]pyrimidine-5-carboxamide;

6-[(4,5-dichloro-2-methyl-1H-imidazol-1-yl)methyl]-1,2,3,4-tetrahydro-N-methoxy-N,3-dimethyl-1-(1-methylethyl)-2,4-dioxo-thieno[2,3-d]pyrimidine-5-carboxamide;

1,2,3,4-tetrahydro-6-(1H-indazol-3-ylmethyl)-N-methoxy-N,3-dimethyl-1-(2-methylpropyl)-2,4-dioxo-thieno[2,3-d]pyrimidine-5-carboxamide;

6-[(4,5-dichloro-2-methyl-1H-imidazol-1-yl)methyl]-1,2,3,4-tetrahydro-N-methoxy-N,3-dimethyl-2,4-dioxo-1-propyl-thieno[2,3-d]pyrimidine-5-carboxamide;

1-(2,2-dimethylpropyl)-1,2,3,4-tetrahydro-N-methoxy-N,3-dimethyl-2,4-dioxo-6-(quinolin-4-ylmethyl)-thieno[2,3-d]pyrimidine-5-carboxamide;

1,2,3,4-tetrahydro-N-methoxy-N,3-dimethyl-6-[[2-(1-methylethyl)-1H-imidazol-1-yl]methyl]-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-6-[[2-(methylthio)-1H-imidazol-1-yl]methyl]-2,4-dioxo-thieno[2,3-d]pyrimidine-5-carboxamide;

6-[(2-chloro-1H-imidazol-1-yl)methyl]-1,2,3,4-tetrahydro-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-6-[2-(methylthio)-1H-benzimidazol-1-yl]-2,4-dioxo-thieno[2,3-d]pyrimidine-5-carboxamide;

1,2,3,4-tetrahydro-N-(2-hydroxyethyl)-N-methoxy-3-methyl-1-(2-methylpropyl)-6-[[2-(methylthio)-1H-imidazol-1-yl]methyl]-2,4-dioxo-thieno[2,3-d]pyrimidine-5-carboxamide;

1,2,3,4-tetrahydro-6-[[2-(methylamino)-1H-benzimidazol-1-yl]methyl]-N-methoxy-N,3-dimethyl-1-(2-methylpropyl)-2,4-dioxo-thieno[2,3-d]pyrimidine-5-carboxamide;

1,2,3,4-tetrahydro-N-methoxy-N,3-dimethyl-1-(2-methylpropyl)-2,4-dioxo-6-[(2-propyl-1H-benzimidazol-1-yl)methyl]-thieno[2,3-d]pyrimidine-5-carboxamide;

1,2,3,4-tetrahydro-N-methoxy-N,3-dimethyl-1-(2-methylpropyl)-2,4-dioxo-6-[(2,3-dihydro-3-methyl-2-oxo-1H-benzimidazol-1-yl)methyl]-thieno[2,3-d]pyrimidine-5-carboxamide;

6-[(2,3-dihydro-2-oxo-benzothiazol-3-yl)methyl]-1,2,3,4-tetrahydro-N-methoxy-N,3-dimethyl-1-(2-methylpropyl)-2,4-dioxo-thieno[2,3-d]pyrimidine-5-carboxamide;

6-[(1-acetyl-1H-indol-3-yl)methyl]-1,2,3,4-tetrahydro-N-methoxy-N,3-dimethyl-1-(2-methylpropyl)-2,4-dioxothieno[2,3-d]pyrimidine-5-carboxamide;

1,2,3,4-tetrahydro-N-methoxy-N,3-dimethyl-1-(2-methylpropyl)-6-[(2-methyl-1H-pyrrolo[2,3-b]pyridin-3-yl)methyl]-2,4-dioxo-thieno[2,3-d]pyrimidine-5-carboxamide;

6-[(3-chloroquinolin-4-yl)methyl]-1,2,3,4-tetrahydro-N-methoxy-N,3-dimethyl-1-(2-methylpropyl)-2,4-dioxothieno[2,3-d]pyrimidine-5-carboxamide;

N-methoxy-N,3-dimethyl-2,4-dioxo-1-propyl-6-(quinolin-4-ylmethyl)-1,2,3,4-tetrahydrothieno[2,3-d]pyrimidine-5-carboxamide;

1-ethyl-N-methoxy-N,3-dimethyl-2,4-dioxo-6-(quinolin-4-ylmethyl)-1,2,3,4-tetrahydrothieno[2,3-d]pyrimidine-5-carboxamide;

1-(cyclopropylmethyl)-N-methoxy-N,3-dimethyl-2,4-dioxo-6-(quinolin-4-ylmethyl)-1,2,3,4-tetrahydrothieno[2,3-d]pyrimidine-5-carboxamide;

1,2,3,4-tetrahydro-N-methoxy-N,3-dimethyl-6-[(2-methyl-1H-indol-3-yl)methyl]-1-(2-methylpropyl)-2,4-dioxothieno[2,3-d]pyrimidine-5-carboxamide;

1,2,3,4-tetrahydro-N-methoxy-N,3-dimethyl-6-[2-methyl-1H-indol-3-ylmethyl]-1-(2-methylpropyl)-2,4-dioxothieno[2,3-d]pyrimidine-5-carboxamide;

N-methoxy-N,3-dimethyl-2,4-dioxo-1-propyl-6-(quinolin-4-ylmethyl)-1,2,3,4-tetrahydrothieno[2,3-d]pyrimidine-5-carboxamide;

1-ethyl-N-methoxy-N,3-dimethyl-2,4-dioxo-6-(quinolin-4-ylmethyl)-1,2,3,4-tetrahydrothieno[2,3-d]pyrimidine-5-carboxamide;

1-(cyclopropylmethyl)-N-methoxy-N,3-dimethyl-2,4-di-oxo-6-(quinolin-4-ylmethyl)-1,2,3,4-tetrahydrothieno[2,3-d]pyrimidine-5-carboxamide;
6-[4,5-dichloro-2-(hydroxymethyl)-1H-imidazol-1-ylmethyl]-1,2,3,4-tetrahydro-N-methoxy-N,3-dimethyl-1-(2-methylpropyl)-2,4-dioxo-thieno[2,3-d]pyrimidine-5-carboxamide;
1,2,3,4-tetrahydro-N-methoxy-N,3-dimethyl-6-[2-methyl-1H-pyrrolo[2,3-b]pyridin-3-ylmethyl]-2,4-dioxo-1-propyl-thieno[2,3-d]pyrimidine-5-carboxamide;
1,2,3,4-tetrahydro-N-methoxy-N,3-dimethyl-1-(1-methylethyl)-6-[2-methyl-1H-pyrrolo[2,3-b]pyridin-3-ylmethyl]-2,4-dioxo-thieno[2,3-d]pryimidine-5-carboxamide;
1,2,3,4-tetrahydro-N-methoxy-N,3-dimethyl-1-(2-methylpropyl)-2,4-dioxo-6-[2-(trifluoromethyl)phenylmethyl]thieno[2,3-d]pyrimidine-5-carboxamide;
1,2,3,4-tetrahydro-N-methoxy-N,3-dimethyl-1-(2-methylpropyl)-2,4-dioxo-6-(benzyl)thieno[2,3-d]pyrimidine-5-carboxamide;
methyl 4-[1,2,3,4-tetrahydro-5-[(N-methoxy-N-methylamino)carbonyl]-3-methyl-1-(2-methylpropyl)-2,4-dioxothieno[2,3-d]pyrimidin-6-yl](hydroxy)methyl]-1-methyl-1H-pyrrole-2-carboxylate;
methyl 1-methyl-4-[1,2,3,4-tetrahydro-5-[(methoxymethylamino)carbonyl]-3-methyl-1-(2-methylpropyl)-2,4-dioxothieno[2,3-d]pyrimidin-6-ylmethyl]-1H-pyrrole-2-carboxylate;
methyl 2,5-dimethyl-4-[1,2,3,4-tetrahydro-5-[(N-methoxy-N-methyl amino)carbonyl]-3-methyl-1-(2-methylpropyl)-2,4-dioxothieno[2,3-d]pyrimidin-6-ylmethyl]-1H-pyrrole-3-carboxylate;
1,2,3,4-tetrahydro-N-methoxy-N,3-dimethyl-1-(2-methylpropyl)-2,4-dioxo-6-[2-oxo-3(2H-benzoxazolylmethyl]-thieno[2,3-d]pyrimidine-5-carboxamide;
1,2,3,4-tetrahydro-N-methoxy-N,3-dimethyl-1-(2-methylpropyl)-2,4-dioxo-6-[(2,4,5-trichloro-1H-imidazol-1-yl)methyl]-thieno[2,3-d]pyrimidine-5-carboxamide;
6-[4,5-dichloro-2-methyl-1H-imidazol-1-ylmethyl]-N-(2-hydroxyethyl)-1-isobutyl-N-methoxy-3-methyl-2,4-dioxo-1,2,3,4-tetrahydrothieno[2,3-d]pyrimidine-5-carboxamide;
6-[4,5-dichloro-2-methyl-1H-imidazol-1-ylmethyl]-N-(2-hydroxyethoxy)-1-isobutyl-N,3-dimethyl-2,4-dioxo-1,2,3,4-tetrahydrothieno[2,3-d]pyrimidine-5-carboxamide; and
6-[4,5-dichloro-2-methyl-1H-imidazol-1-ylmethyl]-N-ethyl-1,2,3,4-tetrahydro-N-methoxy-3-methyl-1-(2-methylpropyl)-2,4-dioxo-thieno[2,3-d]pyrimidine-5-carboxamide;
or a pharmaceutically-acceptable salt thereof.

14. A process for the preparation of a compound of the formula (1) as defined in claim 1, or a compound of the formula (1) as defined in claim 1 wherein at least 1 functional group is protected, using one of the following processes:

a) when $R^3$ is of the formula —CON($R^{10}$)Y($R^{11}$), reacting a compound of the formula (10):

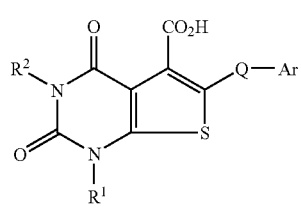

(10)

with a compound of the formula HN($R^{10}$)Y($R^{11}$);

b) when $R^1$ is of the formula —SO$_2$N($R^{10}$)Y($R^{11}$), reacting a compound of the formula (11):

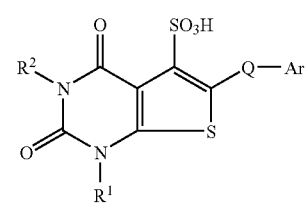

(11)

with a compound of the formula HN($R^{10}$)Y($R^{11}$);

c) when Q is methylene, reacting a compound of the formula (12):

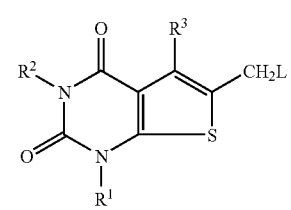

(12)

with a compound of the formula Ar;

d) when Q is methylene, reducing a compound of the formula (13):

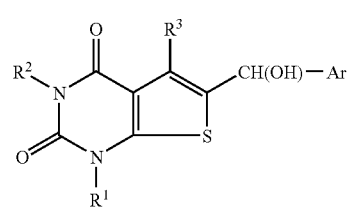

(13)

e) reacting a compound of the formula (14):

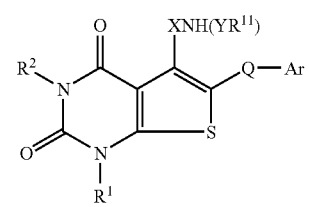

(14)

with a compound of the formula L'-$R^{10}$; or f) converting one compound of the formula (1) into another compound of the formula (1);

wherein L and L' are leaving groups, X is —CO— or —SO$_2$— and $R^1$, $R^2$, $R^3$, $R^{10}$, Q and Ar are as hereinabove defined and any functional groups are optionally protected;

and optionally after a), b), c), d), e) or f), converting the compound of the formula (1) into a further compound of formula (1) and/or forming a pharmaceutically-acceptable salt thereof.

15. A pharmaceutical composition comprising a compound according to claim 1 and a pharmaceutically acceptable adjuvant, diluent or carrier.

* * * * *

UNITED STATES PATENT AND TRADEMARK OFFICE
CERTIFICATE OF CORRECTION

PATENT NO. : 7,361,660 B2
APPLICATION NO. : 10/483161
DATED : April 22, 2008
INVENTOR(S) : Rachel Heulwen Reynolds and Anthony Howard Ingall It is certified that error appears in the above-identified patent and that said Letters Patent is hereby corrected as shown below:

Column 60
Line 32, after "$R^3$" insert -- is --.

Column 63
Line 13, delete "pryimidine" and insert -- pyrimidine --.

Column 64
Line 1, delete "$R^1$" and insert -- $R^3$ --.

Signed and Sealed this

Fifteenth Day of July, 2008

JON W. DUDAS
*Director of the United States Patent and Trademark Office*